US008936793B2

(12) United States Patent
Sprott et al.

(10) Patent No.: US 8,936,793 B2
(45) Date of Patent: Jan. 20, 2015

(54) SYNTHETIC ARCHAEAL GLYCOLIPID ADJUVANTS

(75) Inventors: Dennis Sprott, Ottawa (CA); Dennis M. Whitfield, Ottawa (CA); Lakshmi Krishnan, Ottawa (CA)

(73) Assignee: National Research Council of Canada, Ottawa (CA)

( * ) Notice: Subject to any disclaimer, the term of this patent is extended or adjusted under 35 U.S.C. 154(b) by 591 days.

(21) Appl. No.: 12/225,381

(22) PCT Filed: Mar. 30, 2007

(86) PCT No.: PCT/CA2007/000530
§ 371 (c)(1),
(2), (4) Date: Feb. 25, 2009

(87) PCT Pub. No.: WO2007/112567
PCT Pub. Date: Oct. 11, 2007

(65) Prior Publication Data
US 2010/0316657 A1   Dec. 16, 2010

Related U.S. Application Data

(60) Provisional application No. 60/787,170, filed on Mar. 30, 2006, provisional application No. 60/791,225, filed on Apr. 12, 2006.

(51) Int. Cl.
| A61K 39/395 | (2006.01) |
| A61K 9/127 | (2006.01) |
| A61K 39/39 | (2006.01) |
| C07H 15/06 | (2006.01) |
| A61K 39/00 | (2006.01) |

(52) U.S. Cl.
CPC .............. *A61K 9/1272* (2013.01); *A61K 39/39* (2013.01); *C07H 15/06* (2013.01); *A61K 2039/55583* (2013.01); *A61K 2039/55594* (2013.01)
USPC .................................... 424/278.1; 424/279.1

(58) Field of Classification Search
None
See application file for complete search history.

(56) References Cited

U.S. PATENT DOCUMENTS 6,403,117 B1 * 6/2002 Sprott et al. ............... 424/450

FOREIGN PATENT DOCUMENTS

| WO | WO97223333 | 6/1997 |
| WO | WO0126683 | 4/2001 |

OTHER PUBLICATIONS

Eguchi T. et al, "Total Synthesis of archaeal 36-membered macrocyclic diether lipid", J. Org. Chem. 1997, 62(7), 1924-1933. p. 1928, compounds 35 and 36.
Eguchi T. et al, "Total Synthesis of archaeal 72-membered macrocyclic tetraether lipids", J. Org. Chem. 1998, 63(8), 2689-2698. Compounds 3a and 3b.
Dannenmuller O. et al, "Membrane properties of archaeal diether phospholipids", Chemistry—A European Journal 2000, 6(4), 645-654. Lipids A, B, C and D.
Hancock A.J. et al, "Synthesis of sulfate esters of phosphatidylglycerol (diphytanyl ether analog)", J. Lipid Res. 1973, 14, 430-437. Compound 2, scheme 1, tables 1 and 3.
Van Boekel C.A.A. et al, "Synthesis of two purple-membrane glycolipids and the glycolipid sulfate O-(β-D-glucopyranosyl-3-sulfate)-(1→6)-O-α-D-mannopyranosyl-(1→2)-O-60
-D-glucopyranosyl-(1-1)-2,3-di-O-phytanyl-sn-glycerol",
Carbohydr Res. 1984, 133, 219-234. p. 220, compounds 1, 2 and 3.
Kamikawa T. et al, "Synthesis of 2,3-di-O-phytanyl-1-O-(α-D-glucopyranosyl)-sn-glycerol derivatives, analogues of polar lipids isolated from a halophilic bacterial strain", Glycoconj. J. 1993, 10(3), 235-239.
Velty R. et al, "n-Pentenyl furanosides and related glycosyl donors for the synthesis of archaeol glycolipid analogues", Synlett 1996, 817-819.
Kates M. "Archaebacterial lipids: structure, biosynthesis and function", Biochem. Soc. Symp. 1992, 58, 51-72.
Koga Y. et al, "Recent advances in structural research on ether lipids for archaea including comparative and physiological aspects", Biosci. Biotechnol. Biochem. 2005, 69(11), 2019-2034.
Sprott D. et al, "A structural comparison of the total polar lipids from the human archaea *Methanobrevibacter smithii* and *Methanosphaera stadtmanae* and its relevance to the adjuvant activities of their liposomes", Biochem. Biophys. Acta 1999, 1440(2-3), 275-88.
Krishnan et al, "Archaeosome vaccine adjuvants induce strong humoral, cell-mediated and memory responses: comparison to conventional liposomes and alum", Infect. Immun. 2000, 68(1), 54-63. p. 27, col. 1, para. 3, table 3.
Patel G.B. et al, "Archaeosome immunostimulatory vaccine delivery system", Curr. Drug Del. 2005, 2, 407-421.
Agnihotri G. et al., "One-pot synthesis of per-O-acetylated thioglycosides from unprotected reducing sugars", 2005, Carbohydr. Res. 340:1393-1396.
Benvegnu T. et al., "Archaeosomes based on novel synthetic tetraether-type lipids for the development of oral delivery systems", 2005, Chem. Commun. (Camb.) 5536-5538.
Berkowitz W.F. et al., "Synthesis of archaebacterial lipid C20 chirons", 1997, Tetrahedron Letters 38: 8141-8144.
Blocher D. et al., "Physicochemical characterization of tetraether lipids from *Thermoplasma acidophilum*. V. Evidence for the existence of a metastable state in lipids with acrylic hydrocarbon chains", 1990, Biochim. Biophys. Acta 1024:54-60.
Cross G.G. et al., "Simplifying oligosaccharide synthesis: boronate diesters as cleavable protecting groups", 1998, Synlett. 487-488.
Douglas S.P. et al., "Polymer-supported solution synthesis of oligosaccharides using a novel versatile linker for the synthesis of D-mannopentaose, a structural unit of D-mannans of pathogenic yeasts", 1995, J. Am. Chem. Soc. 117:2116-2117.

(Continued)

*Primary Examiner* — Yunsoo Kim
(74) *Attorney, Agent, or Firm* — Cassan Maclean

(57) ABSTRACT

Archaeal lipid adjuvants are synthesized by chemically coupling various carbohydrates or anionic polar groups to the free hydroxyl(s) of archaeal lipid cores. Chemically stable lipid cores such as saturated archaeol and caldarchaeol are obtained from appropriate Archaea. Archaeosome lipid vesicles are formulated from the synthetic lipids selected to serve as antigen carriers that target antigen-presenting cells and promote an appropriate immune response to the antigen.

16 Claims, 14 Drawing Sheets

(56) References Cited

OTHER PUBLICATIONS

Eichler E. et al., "1-Methyl-1'-cyclopropylmethyl- an acid labile O-protecting group for polymer-supported oligosaccharide synthesis", 2001, Tetrahedron 57:6679-6693.

Gophna U., "Have archaeal genes contributed to bacterial virulence?", 2004, Trends Microbiol. 12:213-219.

Gurnani K. et al., "Phosphatidylserine receptor-mediated recognition of archaeosome adjuvant promotes endocytosis and MHC class I cross-presentation of the entrapped antigen by phagosome-to-cytosol transport and classical processing", 2004, J. Immunol. 173:556-578.

Huang X. et al., "Iterative one-pot oligosaccharide synthesis", 2004, Agnew Chem. Int. Ed. 43:5221-5224.

Krishnan L. et al., "Archaeosomes induce long-term CD8+ cytotoxic T cell response to entrapped soluble protein by the exogenous cytosolic pathway, in the absence of CD4+ T cell help", 2000, J. Immunol. 165:5177-5185.

Krishnan L. et al., "Archaeosomes induce enhanced cytotoxic T lymphocyte responses to entrapped soluble protein in the absence of interleukin 12 and protect against tumor challenge", 2003, Cancer Res. 63:2526-2534.

Krishnan L. et al., "Archaeosomes as self-adjuvanting delivery systems for cancer vaccines", 2003, Journal of Drug Targeting 11:515-524.

Minamikawa H. et al., "Synthesis of 1,3-di-O-alkyl-2-O-(β-glycosyl) glycerols bearing oligosaccharides as hydrophilic groups", 1994, Chem. Phys. Lipids 72: 111-118.

Minamikawa H. et al., "Phase behavior of synthetic phytanyl-chained glycolipid/water systems", 1997, Langmuir 13:2564-2571.

Palma A.S. et al., "Ligands for the beta-glucan receptor, dectin-1, assigned using "designer" microarrays of oligosaccharide probes (neoglycolipids) generated from glucan polysaccharides", 2006, J. Biol. Chem. 281:5771-5779.

Prakash G.K. et al., "BF32CF3CH2OH(BF32TFE), an efficient superacidic catalyst for some organic synthetic transformations", 2006, J. Org. Chem. 71: 3952-3958.

Raguse B. et al., "The synthesis of archaebacterial lipid analogues", 2000, Tetrahedron Letters 41:2971-2974.

Sprott G.D. et al., "Adjuvant potential of archaeal synthetic glycolipid mimetics critically depends on the glyco head group structure", 2008, Glycobiology vol. 18 No. 7 pp. 559-565.

Sprott, G.D. et al., "Novel, acid-labile, hydroxydiether lipid cores in methanogenic bacteria", 1990, J. Biol. Chem. 265:13735-13740.

Sprott, G.D. et al., "Novel polar lipids of halophilic eubacterium Planococcus H8 and archaeon *Haloferax volcanii*", 2003, Biochim. Biophys. Acta 1633:179-188.

Sprott, G.D. et al., "Archaeobacterial ether lipid liposomes as vaccine adjuvants", 2003, Methods Enzymol 373:155-172.

Sprott, G.D. et al., "Archaeosomes varying in lipid composition differ in receptor-mediated endocytosis and differentially adjuvant immune responses to entrapped protein", 2003, Archaea 1:151-164.

Sprott, G.D. et al., "Identification of sulfoquinovosyl diacylglycerol as a major polar lipid in Marinococcus halophilus and Salinicoccus hispanicus and substitution with phosphatidylglycerol", 2006, Can. J. Microbiol. 52:209-219.

Sprott, G.D. et al., "Glycosidase-induced fusion of isoprenoid gentiobiosyl lipid membranes at acidic pH", 2009, Glycobiol. vol. 19, No. 3, pp. 267-276.

Swain M. et al., "Identification of beta-L-glucose as the sugar moiety of the main polar lipid *Thermoplasma acidophilum*", 1997, Biochem. Biophys. Acta 1345:56-64.

Tropper F.D. et al., "Stereospecific synthesis of 1,2-trans-phenylthio-β-D-disaccharides under phase transfer catalysis", 1991, Synthesis 734-736.

Whitfield D.M. et al., "Synthesis of archael glycolipid adjuvants—what is the optimum number of sugars?", 2008, Carbohydrate Research 343:2349-2360.

Yan H. et al., "Synthesis of mono- and di-sialophospholipids via the H-phosphonate approach", 2006, Can. J. Chem. 84:540-545.

Office Action relating to Canadian Application Serial No. 2,647,060 dated Mar. 25, 2013.

Office Action relating to European Application Serial No. 07719462. 9—1452 / 1999137 dated Mar. 5, 2013.

Tomoaia-Cotisel, et al, "Acid dissociation constants of diphytanylglycerolphosphorylglycerol-methylphosphate, and diphytanylglycerolphosphorylglycerophosphate and its deoxy analog" Chemistry and Physics of Lipids 100 (1999) 41-54.

\* cited by examiner

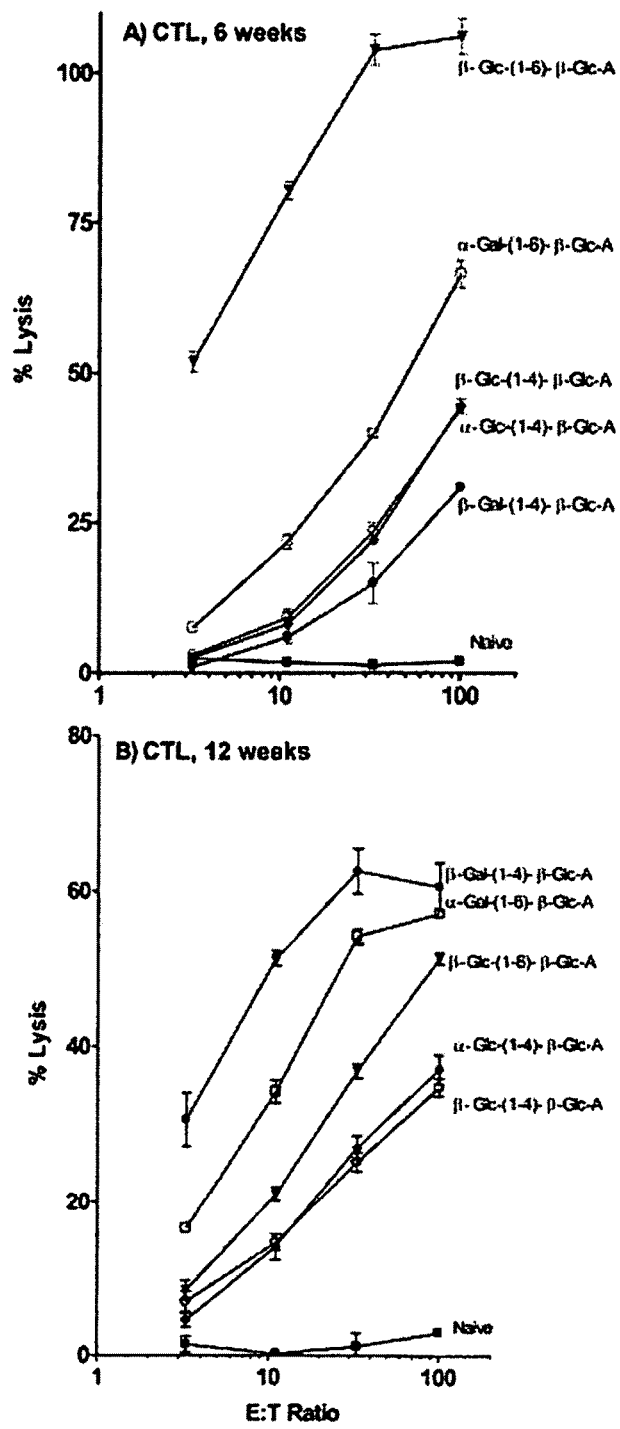
Fig. 7 A,B

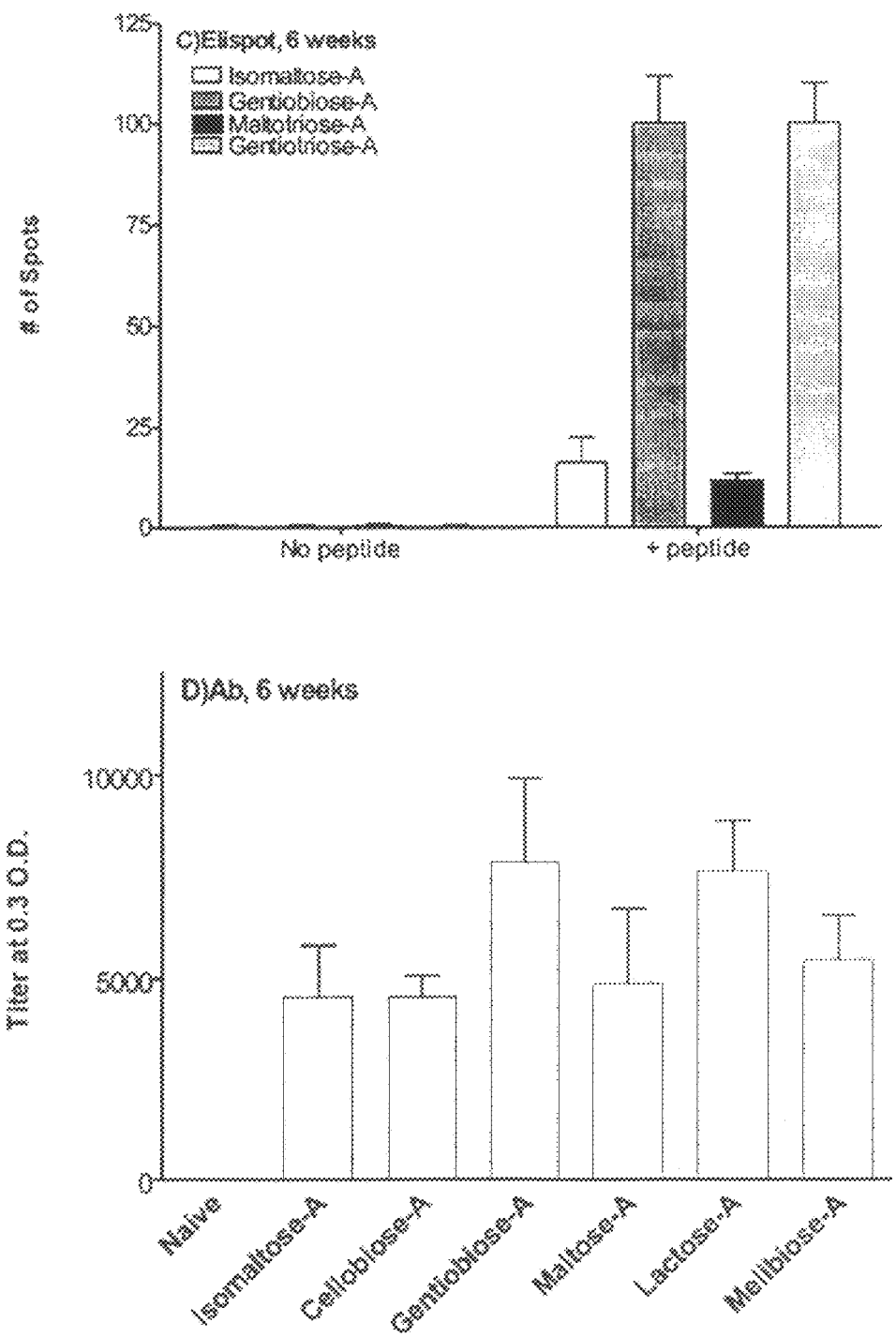
Fig. 7 C,D

US 8,936,793 B2

SYNTHETIC ARCHAEAL GLYCOLIPID ADJUVANTS

RELATED APPLICATIONS

This is a national entry application claiming the benefit of PCT Application No. PCT/CA2007/000530 which claims priority to U.S. Provisional Application Nos. 60/787,170 filed Mar. 30, 2006 and 60/791,225 filed Apr. 12, 2006.

FIELD OF THE INVENTION

This invention relates to the preparation of synthetic archaeal polar lipids whose structures are selected to achieve a desired immune system activating activity.

BACKGROUND OF THE INVENTION

Archaeal polar lipids are novel to the domain of life Archaea and are characterized as isoprenoid ether lipids of opposite sn-2,3 stereochemistry (12). Archaeosome vaccine adjuvants comprising natural lipid mixtures extracted from an archaeon have previously been disclosed. Such adjuvants alleviate the need for effective induction of humoral (Th2), cell-mediated (Th1), and particularly CD8+ cytotoxic T cell responses (CTL) to an antigen (25, 28). The disclosed lipids are restricted to the polar lipids extracted from archaeal biomass.

Best long-term adjuvant activity and memory responses occurred with archaeosomes prepared from the total polar lipids (TPL) of *Methatzobrevibacter snzithii* and *Thermoplasma acidophilum* (16), both of which have challenges in their preparation. *M. smithii* is an obligate anaerobe, requiring specialized medium for growth, including toxic sulfides and potentially flammable, explosive levels (80%) of hydrogen gas. Methanogens such as *M. smithii* must be protected from the lethal effects of oxygen in air. *Thermoplasma* and *Sulfolobus* TPLs consist of about 90% caldarchaeol membrane-spanning lipids that hydrate to form archaeosomes at low recoveries, in our experience of about 10-20%. Purification of lipids from lipid extracts is uncertain, tedious and costly. A more efficient, cost-effective method to produce archaeal polar lipids would be a great advantage.

Further, use of archaeal TPL natural mixtures limits the adjuvant composition to only those lipids, and in the proportions, that are extracted from archaeal species. This approach is likely to achieve stable archaeosomes but may not be optimal for a selected application. The lipid composition of the vaccine may theoretically determine whether protection occurs or not, based on the type of immune response (MHC class I or II presentation—FIG. 1A, or systemic versus mucosal) that is generated to the antigen.

For human applications the lipid mixture used for archaeosome formation needs to be defined and reproducibly produced from each batch of biomass grown and extracted. Recovery of mixtures of often 10 or more different polar lipids in each TPL extract is typical. Production benefits, including more control of head group in/out orientation on the archaeosome surface, as well as ease of obtaining regulatory approval for human use of defined and simplified compositions, may be anticipated.

Natural archaeal core lipids are predominantly of two types; namely, archaeol and its dimer called caldarchaeol (FIG. 1B). Both of these core lipids or their analogues may be synthesized chemically (3, 21). However, chemical synthesis of archaeal core lipids is complex and must consider the problems of producing mixed stereoisomers (methyl groups of archaeal isoprenoid chains are R) and of generating unwanted chemical by-products. In addition, the archaeal sn-2,3 stereochemistry must be adhered to.

DESCRIPTION OF THE PRIOR ART

Friesleben et al (8) have grown *Thermoplasma acidophilum* and obtained a caldarchaeol lipid core. The 2 free hydroxyl groups on the caldarchaeol were reacted to form carboxylic acid groups, then dicarboxylic acid chloride, then reacted with dimethylaminopropylamine and finally with dimethylsulfate. The result was a positively charged caldarchaeol capable of binding DNA by charge-charge interactions, for the purpose of transfecting cells.

Benvegnu et al (2) prepared a synthetic tetraether lipid by linking 2 glycerols by C15 saturated polymethylene chains through a cyclopentane group and attaching lactose or phosphatidylcholine groups to the 2 free hydroxyls. This synthetic tetraether lipid differs considerably in structure from archaeal caldarchaeols with unpredictable changes in biological responses. These authors report the relative ability of these synthetic tetraether lipids to form liposomes, and suggest their stability properties may be useful for oral drug delivery.

Three archaeal lipids found in *Halobacterium salinarum* have been synthesized for studies on the light driven proton pump of purple membrane (32). These were O-(β-D-glucopyranosyl 3-sulfate)-(1-6)-O-α-D-mannopyranosyl-(1-2)-O-α-D-glucopyranosyl-(1-1)-2,3-di-O-phytanyl-sn-glycerol, and O-β-D-glucopyranosyl-(1-6)-O-α-D-mannopyranosyl-(1-2)-O-α-D-glucopyranosyl-(1-1)-2,3-di-O-phytanyl-sn-glycerol, and O-β-D-glucopyranosyl-(1-6)-O-α-D-mannopyranosyl-(1-2)-O-α-D-glucopyranosyl-(1-1)-2,3-di-O-phytanyl-sn-glycerol. The complexity of these lipids makes them unattractive for synthesis as vaccine adjuvants, and additionally the TPL from *H. salinarum* which contains these lipids is unsatisfactory in generating only short-term CTL responses (16).

In another study on the physical chemistry of membranes a 1,2-diphytanyl-3-O-β-D-glucosyl-sn-glycerol was made (4).

Finally, synthesis has been reported for a series of 1,3-di-O-alkyl-2-O-(β-glycosyl)glycerols (18). These glycolipids differ from archaeal lipids and from the synthetic glycolipids reported herein by linkage of the head group specifically to the sn-2 of the glycerol with phytanyl chains at sn-1,3.

In none of the cited literature above is there speculation or suggestion of antigen delivery for vaccine applications. Indeed, in the Benvegnu et al report (2) it may be expected that too much stability would teach away from adjuvant properties by preventing antigen release in vivo. Further, adjuvant activity has never been demonstrated previously for any synthetic archaeal lipid.

In Sprott et al (23) it is stated 'a striking decline in adjuvant activity was observed upon incorporation of 36 mol % of the uncharged lipid DGAs,' where DGAs is biologically purified β-D-Glc-(1,6)-β-D-Glc-archaeol. This finding teaches away from expectation that glyco-archaeols and specifically β-D-Glc-(1,6)-β-D-Glc-archaeol or β-D-Glc-(1,6)-β-D-Glc-caldarchaeols would promote adjuvant activity.

SUMMARY OF THE INVENTION

Archaeal lipid cores including archaeol and caldarchaeol are obtained by methanolic-HCl hydrolysis of the polar lipids extracted from archaea such as *Halobacterium salinarum* or *Thermoplasma acidophilum*, respectively. The source of archaeal core lipids is preferred to be those archaea that have predominantly or wholly saturated, core lipids to avoid instability. Carbohydrate polar head groups or anionic polar head groups of desired type, number, linkage and configuration are then chemically coupled to the archaeal lipid cores, preferably at the free sn-1 hydroxyls of the lipid cores. Such synthetic polar lipids may then be used in the preparation of vaccines formulated as archaeosomes designed to serve as stable antigen carriers that target delivery to antigen-presenting cells, resulting in the appropriate balance of systemic versus mucosal immunity, and $CD8^+$ T cell and $CD4^+$ T cell responses.

A first object of the invention is to provide for a polar synthetic lipid. The polar synthetic lipid may be derived from archaeal lipid cores isolated from archaeal cells and then modified to add carbohydrate polar head groups and/or anionic polar head groups.

A second object of the invention is to provide for an archaeosome lipid vesicle composed of polar synthetic lipids. Preferably the archaeosome should include synthetic lipids that comprise lipids with carbohydrate groups and lipids with anionic groups, or lipids with both carbohydrate and anionic groups. The polar synthetic lipid may act as a stabilizer, or an additional lipid, such as a conventional synthetic lipid, may be added.

A third object of the invention is to provide for a vaccine comprising an archaeosome adjuvant as described above, with an antigen. The vaccine may be designed, for example, to elicit an immune response such as a protective $CD8^+$ or $CD4^+$ T cell response or a mucosal response.

A first aspect of the invention provides for a polar synthetic lipid comprising at least one carbohydrate or anionic group linked by covalent bonding to at least one free hydroxyl group of an archaeal lipid core.

A second aspect of the invention provides for an archaeosome comprising at least one polar synthetic lipid comprising at least one carbohydrate or anionic group linked by covalent bonding to at least one free hydroxyl group of an archaeal lipid core.

A third aspect of the invention provides for a vaccine comprising an adjuvant and an antigen, the adjuvant comprising an archaeosome comprising at least one polar synthetic lipid comprising at least one carbohydrate or anionic group linked by covalent bonding to at least one free hydroxyl group of an archaeal lipid core.

A further aspect of the invention provides for the use of a vaccine for the promotion of an immune response, the vaccine comprising an adjuvant and an antigen, the adjuvant comprising an archaeosome comprising at least one polar synthetic lipid comprising at least one carbohydrate or anionic group linked by covalent bonding to at least one free hydroxyl group of an archaeal lipid core.

A further aspect of the invention provides for a method for producing a polar synthetic lipid comprising at least one carbohydrate or anionic group linked by covalent bonding to at least one free hydroxyl group of an archaeal lipid core, the method comprising the steps of isolating an archaeal lipid core from archaeal cells, and processing the archaeal lipid core to add the at least one carbohydrate or anionic group.

A further aspect of the invention provides for a method for producing an archaeosome as described above, comprising the steps of isolating archaeal lipid core molecules from archaeal cells, processing the archaeal lipid core molecules to add the at least one carbohydrate or anionic group, adding at least one stabilizing lipid, and allowing an archaeosome to form.

BRIEF DESCRIPTION OF THE DRAWINGS

FIG. 7 shows the adjuvant activity induced in mice immunized with an antigen (15 μg OVA) entrapped in synthetic archaeosomes consisting of various synthetic di- and trisaccharide-archaeols (see FIG. 6)/DPPG/cholesterol (25/55/20, mol %). Immunizations were subcutaneous injections given at 0 and 3 weeks. Splenocytes were taken for CD8$^+$ T CTL assays 6 weeks and 12 weeks post first injection. A, CTL 6 weeks; B, CTL 12 weeks; C, Elispot assay at 6 weeks comparing isomaltose-A to gentiobiose-A, and maltotriose-A to gentiotriose-A; D, Anti-OVA antibody titres in blood, taken 6 weeks post first injection, n=4 mice. Elispot assay in C panel measures the numbers of IFN-γ secreting antigen-specific CD8$^+$ T cells. Production of IFN-γ is another functional readout of CD8$^+$ T cell activation.

DETAILED DESCRIPTION OF THE INVENTION

Figure 1A:
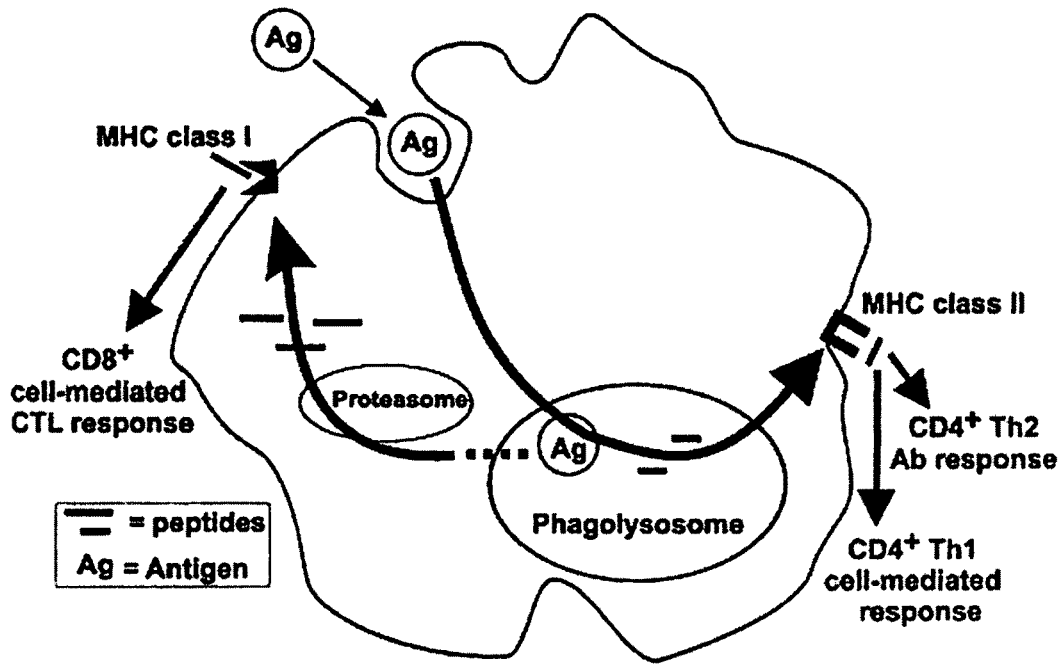
FIG. 1A illustrates two immune response pathways in an antigen-presenting cell, both beginning by phagocytosis of an antigen carried in an archaeosome vesicle. $CD4^+$ T cell responses require that antigen (Ag) be released in the phagolysosome for proteolysis and MHC class II presentation of peptides. Cross presentation (dashed line) of exogenous antigens is unexpected, and requires that antigen (Ag) be translocated to the cytosol for MHC class I presentation of peptides to $CD8^+$ T cells.
Figure 1B:
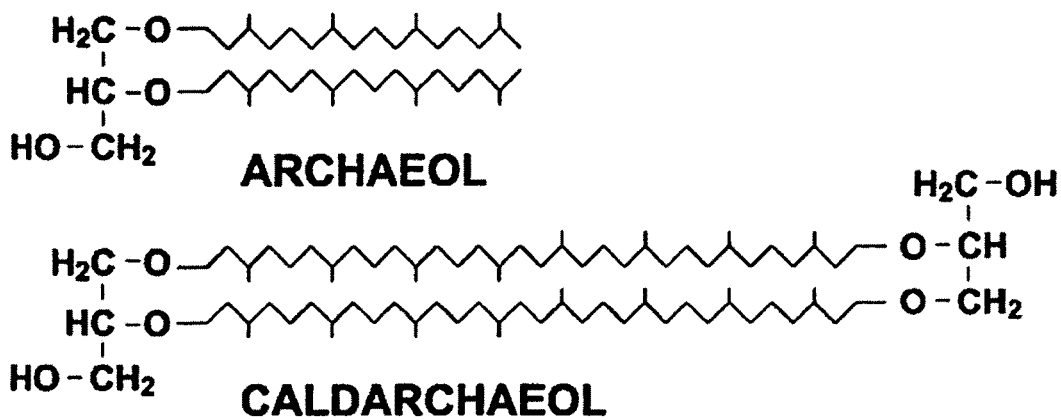
FIG. 1B illustrates the molecular structures of archaeol and caldarchaeol core lipids. Notable features of the structures include ether linkages to isopranoid fully saturated chains of constant C-20 or C-40 length and opposite sn-2,3 stereochemistry of chain attachment to the glycerol backbone(s).

Archaeal core lipids are isolated from archaeal cells, following which polar synthetic lipids are synthesized by attaching various groups, including carbohydrate or anionic groups, to the archaeal core lipids. Stable archaeosomes are prepared from these polar synthetic lipids by including anionic and stabilizing features. Incorporating a protein antigen into these archaeosome compositions and injecting them into mice resulted in an unexpected, strong adjuvant activity for select compositions in immunized mice. The choice of the carbohydrate group in terms of type, number of residues, linkages and configurations were important in determining adjuvant activity. This approach avoids the possibility of encountering the presence of immune system depressing lipids, or immune inactive lipids that occur in TPL extracts, and allows synthesis of potent archaeal lipids that are not found naturally in archaea.

DEFINITIONS

An archaeal lipid refers to a polar lipid common to the Domain Archaea typified by isoprenoid chains in ether linkage to the sn-2,3 carbons of the glycerol backbone.

Archaeal core lipids are most commonly 2,3-di-O-phytanyl-sn-glycerol (archaeol), and 2,2',3,3'-tetra-O-dibiphytanyl-sn-diglycerol (caldarchaeol).

Synthetic archaeal lipids or polar synthetic lipids refer to core lipid precursors either derived from Archaeal lipids by hydrolysis or made by chemical synthesis, conjugated to at least one new head group.

Archaeol phospholipids are referred to using archaetidyl, for example, AG, archaetidylglycerol; AS, archaetidylserine.

Conventional lipids refer to the lipids common to the Domains Bacteria and Eukarya. This includes polar lipids typified by fatty acyl chains in ester linkage to the sn-1,2 carbons of the glycerol backbone, and neutral lipids such as cholesterol. Conventional phospholipids are referred to in the usual way, for example, DPPG, dipalmitoylphosphatidylglycerol; DPPS, dipalmitoylphosphatidylserine.

Archaeosomes refer to closed lipid vesicles that contain any amount of synthetic archaeal lipid(s).

Liposomes are lipid vesicles composed entirely of conventional lipids.

APCs, antigen presenting cells
CTL, cytotoxic T lymphocyte
TPL, total polar lipids obtained by extraction from a specific archaeon
OVA, ovalbumin
AgOTf, silver trifluoromethansulfonate (triflate)
NIS, N-iodosuccinimide
animal, as referred to herein humans are included
glyco, sugar and carbohydrate are used interchangeably In contrast to expectation, the archaeal core lipid chemically coupled with carbohydrate head groups such as β-D-Glc-(1,6)-β-D-Glc-, and certain other carbohydrate head groups not known to exist naturally in archaea, can be induced to form lipid vesicles that promote a strong CTL response in animals to an entrapped antigen. Further, it is shown that the archaeol portion of an archaeal lipid is insufficient in itself to promote adjuvant activity. Thus, archaeal lipids can be categorized as either poor adjuvants or strong adjuvants based on the head groups they possess.

According to one aspect of the invention synthetic chemistry is used to prepare polar synthetic lipids by linking defined carbohydrate head groups (or anionic groups such as phosphoglycerol) to the free sn-1 hydroxyl group of stable archaeal core lipids. Archaeal biomass is the preferred source of the archaeal core lipid, where the archaeal source is chosen to give ease of growth and also a high yield of the desired core lipid product. *Halobacterium salinarum* is chosen as a good source of archaeol because it is an aerobe easily grown using inexpensive media, and produces only saturated polar lipids for increased stability. Further, it has only one core lipid structure (archaeol), and requires high concentrations of NaCl for growth simplifying the maintenance of pure cultures. Further, the cells lyse in water, making lipid extraction from the cell debris very efficient. As is the case for all archaea, there is no pathogenicity associated with this environmental bacterium that lacks endotoxin and other virulence factors (9). Presence of only one core lipid results in high yields, requiring only simple purification steps.

In another aspect of the invention caldarchaeol, or any other core lipid, is prepared based on selecting the appropriate archaeon in which the desired core lipid is abundant. For caldarchaeol isolation an archaeon such as *Thermoplasma* may be preferred compared to *Sulfolobus*, to avoid mixtures of caldarchaeols and nonitol-caldarchaeols found in *Sulfolobus*. Core lipids may be synthesized chemically to achieve the same structures, providing the same stereochemistry of archaeal core lipids is preserved.

In another aspect of the invention novel archaeal lipids not known to exist in nature are synthesized. Further, mixtures of synthetic archaeal lipids are used in the proportions necessary to optimise the desired adjuvant activity, namely $CD4^+$ T cell, $CD8^+$ T cell, or mucosal immunity, of the archaeosomes so formed.

In a further aspect of this invention saturated archaeal lipids with isopranoid chains and ether linkages to the glycerol backbone are used for the synthesis of polar synthetic lipids to give the distinct advantage of chemical stability and allow the chemical coupling and de-blocking steps used in the synthesis to proceed without generating undesired products. In comparison, lipids from sources other than archaea are characterized by unsaturation in their fatty acids that are linked by relatively unstable ester bonds to the glycerol backbone. Archaeal species that have unsaturation in their polar lipids, such as *Haloferax volcanii*, or acid-sensitive 3-hydroxylated isoprenoid chains (24) are generally avoided (26). A further reason for use of archaeal core lipids is that the stereochemistry of archaeal lipids is sn-2,3 versus sn-1,2 for glycerolipids of Bacteria and Eukarya. Although it is not proven, this stereochemistry may be critical for adjuvant activity, as the adjuvant activity of polar glycerolipids of Bacteria and Eukarya is low compared to the glycerolipids of Archaea.

In another aspect of the invention an antigen that may be a surface molecule or epitope (such as an immunodominant amino acid sequence of a protein) expressed by a pathogen or cancer cell, is entrapped in archaeosomes comprised of polar head groups linked synthetically to archaeol/caldarchaeol to form a protective vaccine.

According to another aspect of the invention the issue of difficulty in hydrating and forming archaeosomes from caldarchaeol polar lipid mixtures, as well as from other lipids where the problem occurs, may be solved by constructing an archaeosome of, for example, (1) only archaeol synthetic lipids as the vaccine adjuvant, (2) a mixture of synthetic archaeol/caldarchaeol glycolipids with synthetic anionic archaeol/caldarchaeol lipids or commercially available lipids including DPPG and/or stabilizing cholesterol, or (3) a single synthetic polar caldarchaeol structure with targeting glyco group on one end and anionic group on the other and that is synthesized to be conducive to stable archaeosome formation. These are intended as representative examples only, and it is understood that other possible combinations of archaeal lipids may be possible.

Yet another aspect of the invention provides for a method to elicit an antigen specific, protective MHC class I restricted cytotoxic T cell response ($CD8^+$ T cell response) and an antigen specific MHC class II response ($CD4^+$ T cell response) in an animal, and/or a mucosal response, wherein the synthetic archaeosome vaccine composition formulated with antigen is administered to the animal.

Synthetic Archaeols—Synthesis and Adjuvant Activity

Figure 2:
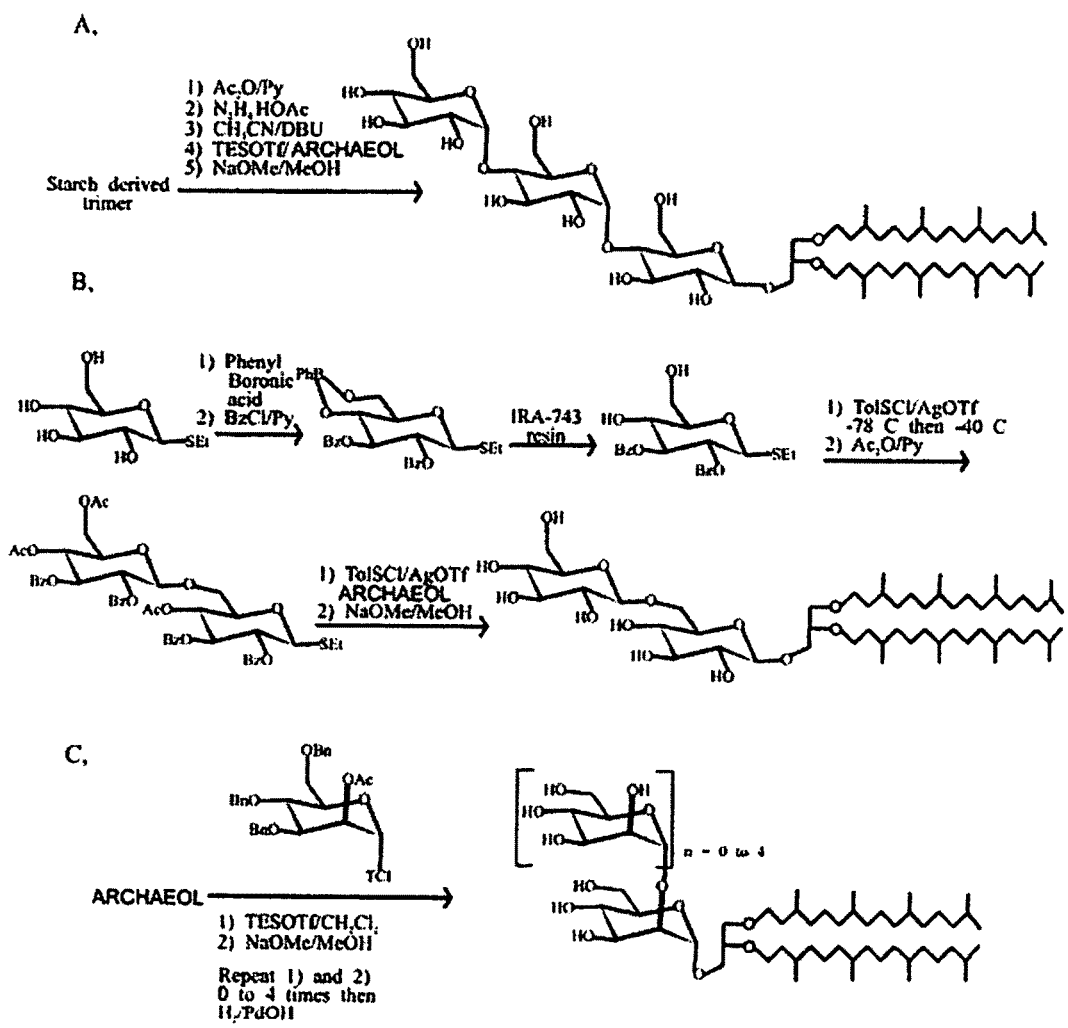
FIG. 2 illustrates synthesis strategies for (A) α-D-Glc-(1,4)-α-D-Glc-(1,4)-β-D-Glc-(1,1)-archaeol, (B) β-D-Glc-(1,6)-β-D-Glc-archaeol, and (C) α-mannose$_{(1-5)}$-archaeols.
Figure 3:
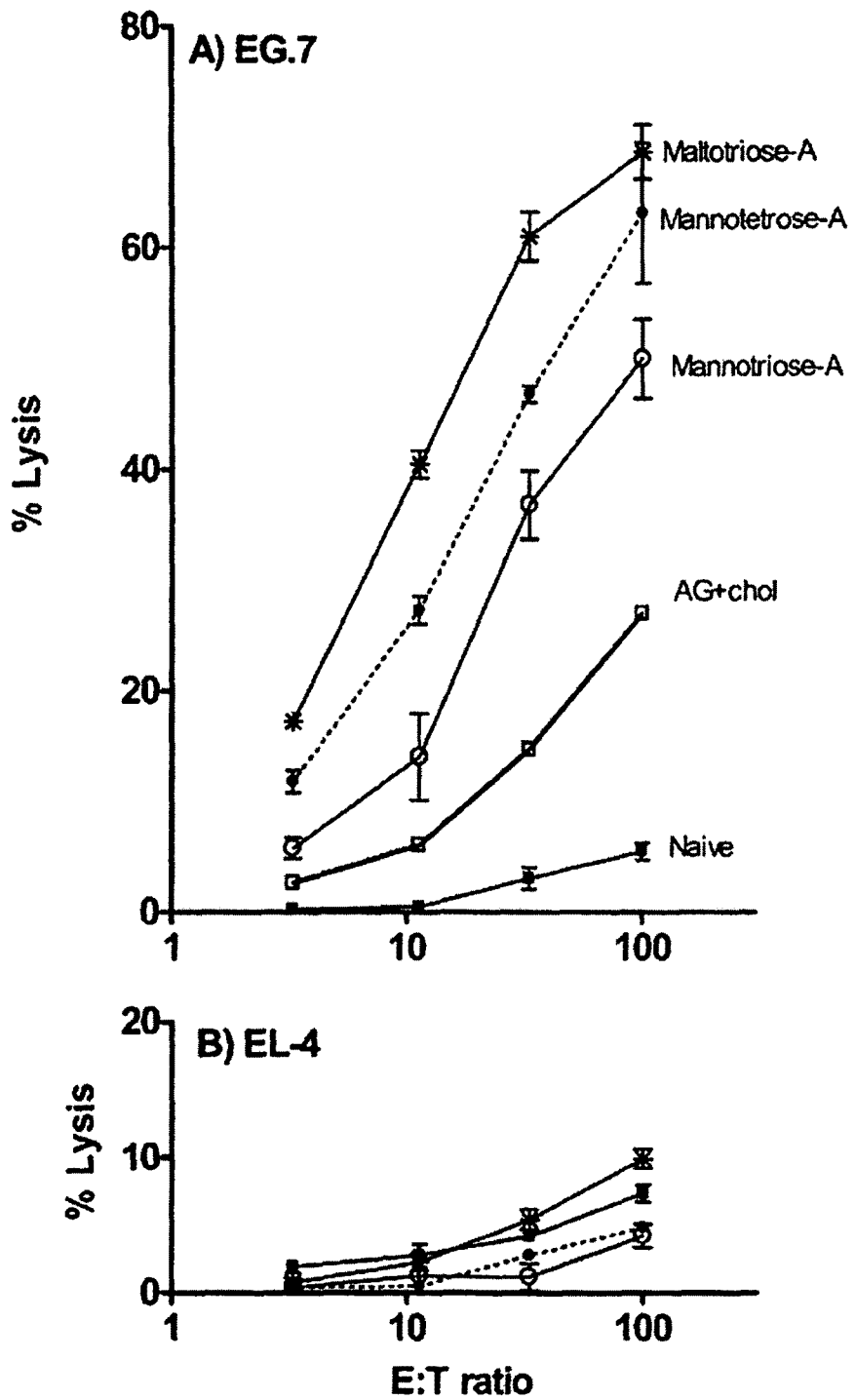
FIG. 3 shows CTL responses in splenocytes of mice immunized subcutaneously at 0 and 3 weeks with archaeosomes consisting of 15 μg OVA entrapped in either maltotriose-archaeol (maltotriose-A), mannotriose-A (α-D-Man-(1,2)-α-D-Man-(1,2)-α-D-Man-(1,1)-archaeol), mannotetraose-archaeol (α-D-Man-(1,2)-α-D-Man-(1,2)-α-D-Man-(1,2)-α-D-Man-(1,1)-archaeol), or archaetidylglycerol (AG). Spleens were taken 7 weeks following the first immunization. Comparatively low adjuvant activity is seen for archaeosomes composed of AG/chol (80/20, mol %). Chol is cholesterol. Splenic CTL responses are shown for antigen specific EG.7 targets (panel A) and non-specific EL-4 targets (panel B) (2 mice/group). EL-4 is the negative control target cells that do not express the MHC class I specific peptide (SIINFEKL) of OVA. Naive mice were non-immunized controls.

Strong CTL adjuvant activity is found for OVA-archaeosomes comprising a synthetic glyco-archaeol lipid and antigen. The first synthetic lipids synthesized (FIG. 2) and tested were:

α-D-Man-(1,2)-α-D-Man-(1,2)-α-D-Man-(1,1)-archaeol;

α-D-Man-(1,2)-α-D-Man-(1,2)-α-D-Man-(1,2)-α-D-Man-(1,1)-archaeol; and

α-D-Glc-(1,4)-α-D-Glc-(1,4)-β-D-Glc-(1,1)-archaeol (FIG. 3). To adjuvant the CTL response, four mannose residues were preferred to three. However, three glucose residues gave best adjuvant activity. This higher activity for α-glucose residues was surprising as macrophages have a well-known mannose receptor to better promote phagocytosis. However, phagocytosis of glyco-archaeal lipids via a mannose receptor, or any other receptor, has not been shown to date. Dectin-1, the recently discovered β-glucan receptor of APCs, is excluded as a mechanism to explain the adjuvant properties of synthetic glyco-archaeols, as that receptor is specific to polysaccharides of at least 10 to 11 glucose residues and has specificity 'exclusively' for β-1,3-linkages (19). Thus, synthetic glyco-archaeols interact with APCs and adjuvant by a new and unexpected mechanism.

Archaeosomes composed of archaetidylglycerol (AG, the archaeal form of phosphatidylglycerol) and cholesterol (80/20, mol %) with antigen (OVA) entrapped, were tested as adjuvants (FIG. 3). These had little ability to serve as adjuvants in animals, showing that the archaeol lipid moiety was insufficient to function as a strong adjuvant per se, without an appropriate head group.

Figure 4:
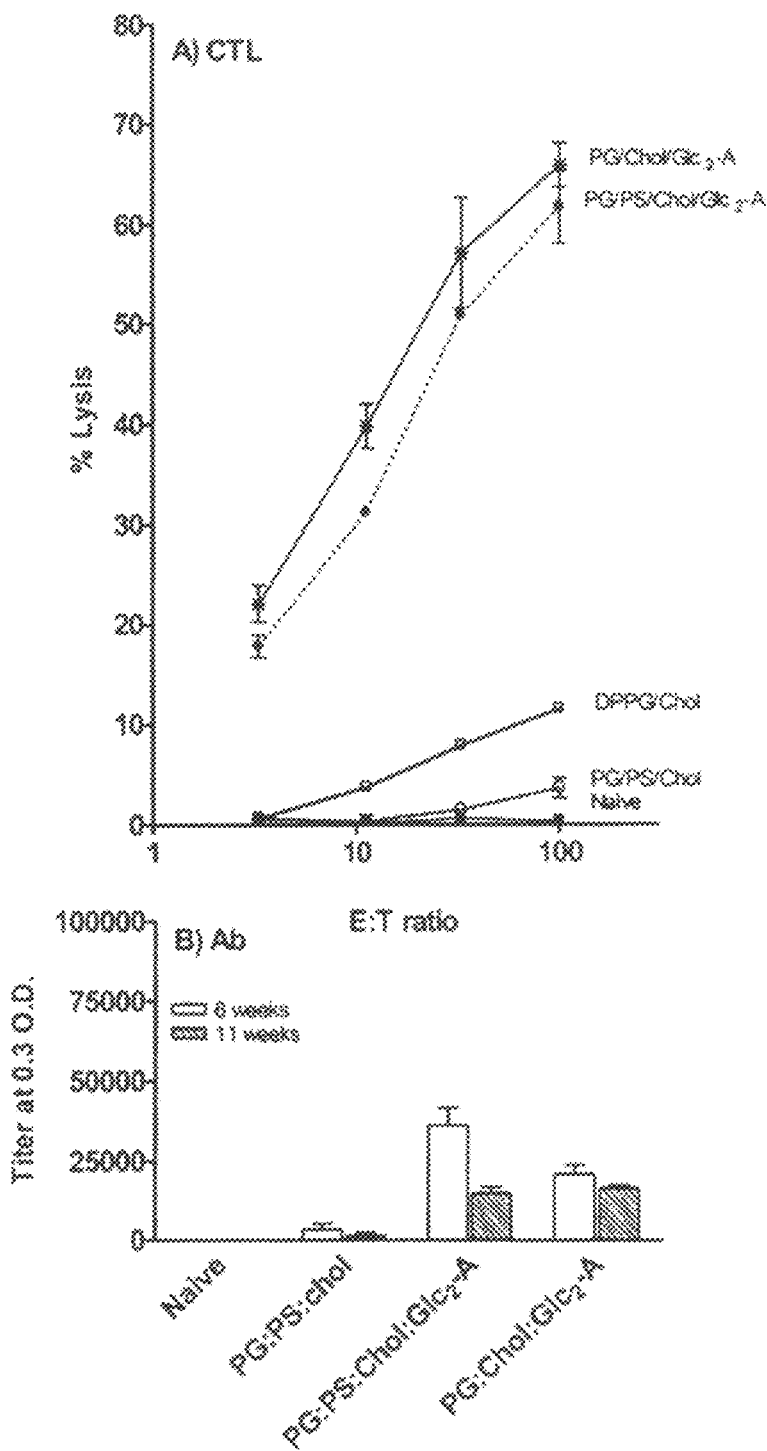
FIG. 4 shows CTL responses in splenocytes of mice (A), and anti-OVA antibody responses in sera of mice (B) immunized subcutaneously at 0 and 3 weeks with 15 μg OVA entrapped in liposomes composed of DPPG/chol (80/20, mol %), DPPG/DPPS/chol (60/20/20, mol %), and archaeosomes consisting of Glc$_2$-A/DPPG/chol (15/65/20, mol %) or Glc$_2$-A/DPPS/DPPG/chol (15/20/45/20, mol %). Glc$_2$-A is synthetic β-D-Glc-(1,6)-β-D-Glc-archaeol. Liposomes induced comparatively very low CTL responses compared to archaeosomes showing that the active ingredient is synthetic Glc$_2$-A. Responses for non-specific EL-4 targets (data not shown) were below 5%. CTL assays were conducted 6 weeks from first injection, and antibody assays at 6 weeks (open bars) and 11 weeks (hatched bars) post first injection.

Archaeosomes did not form readily upon attempts to hydrate shorter chain synthetic α-D-Man-archaeol; α-D-Man-(1,2)-α-D-Man-archaeol; or β-D-Glc-(1,6)-β-D-Glc-archaeol. This difficulty in forming lipid vesicles, and a problem of aggregation noted for the archaeosomes in FIG. 3, was overcome by inclusion of an anionic lipid (DPPG) and cholesterol or DPPG/DPPS/cholesterol lipids. This solution also provided a means of testing various synthetic glyco-archaeols for adjuvant activity. DPPG/cholesterol (80/20, mol %) or DPPG/DPPS/cholesterol (60/20/20, mol %) liposomes had little ability to induce a CTL response or an antibody response in animals to the entrapped antigen (FIG. 4). Instability to prolonged storage with the possible loss of entrapped antigen (and therefore loss of adjuvant activity) was ruled out as the mechanism for poor adjuvant activity in the DPPG, DPPS and Cholesterol liposomes (Table 10). Incorporation of only 15 mol % of synthetic β-D-Glc-(1,6)-β-D-Glc-(1,1)-archaeol to either of these liposome formulations resulted in a dramatic increase in CTL and antibody responses in mice (FIG. 4A,B). This is unanticipated based on previous data (13) showing that the adjuvant activity of archaeal lipids dramatically diminished when mixed with non-archaeal lipids (DMPC/DMPG), and data (23) showing a diminished adjuvant activity with incorporation of biologically purified β-D-Glc-(1,6)-β-D-Glc-archaeol into archaeosomes.

Figure 5:
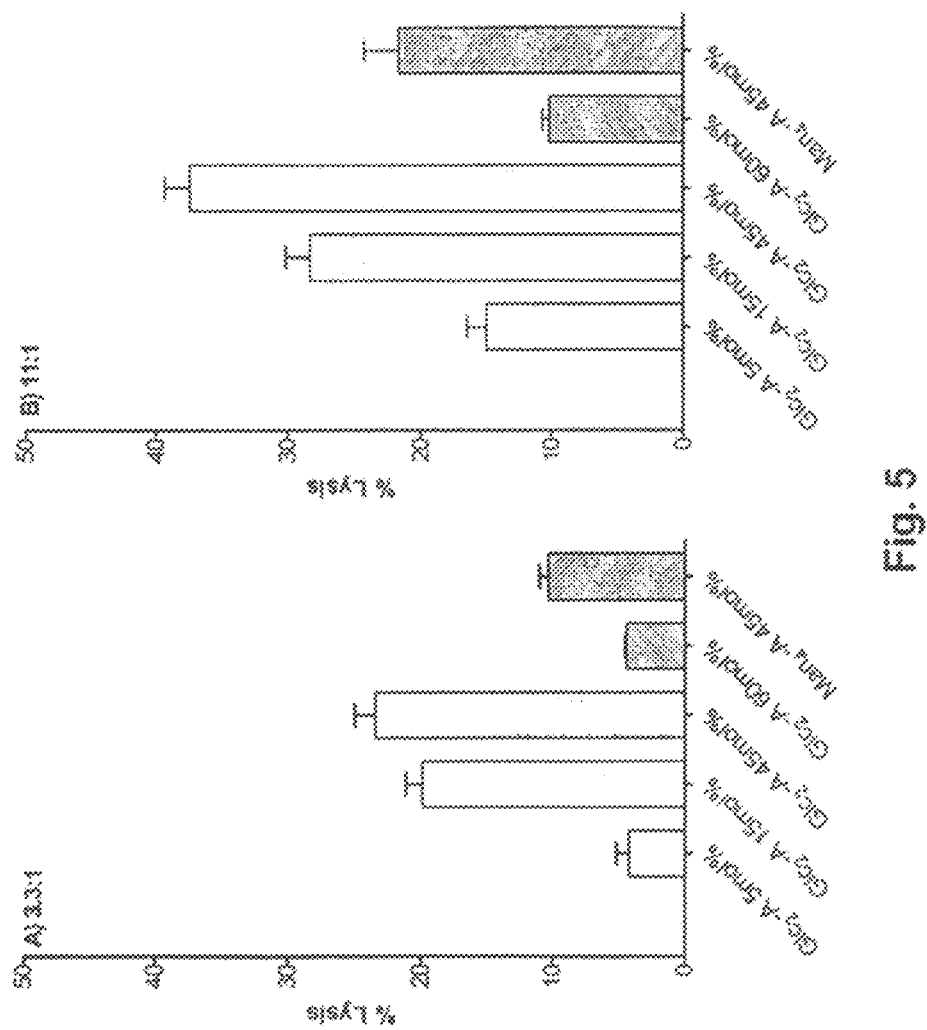
FIG. 5 illustrates that adjuvant activity of synthetic OVA-archaeosomes depends on the mol % composition of synthetic Glc$_2$-archaeol (β-D-Glc-(1,6)-β-D-Glc-archaeol). Cholesterol was held constant in all archaeosomes at 20 mol %, and Glc$_2$-archaeol varied from 5 to 60 mol %. DPPG comprised the remaining mol % of each archaeosome type. Also shown is comparatively lower adjuvant activity of mice immunized with Man$_4$-A/DPPG/chol (45/35/20, mol %), where Man$_4$-A is synthetic α-D-Man-(1,2)-α-D-Man-(1,2)-α-D-Man-(1,2)-α-D-Man-(1,1)-archaeol. Each subcutaneous injection given on 0 and 3 weeks consisted of synthetic archaeosomes with 15 μg OVA entrapped. Data represent CTL ($CD8^+$ T cell) responses measured in spleen cells taken 7 weeks post first injection where effector to target ratios (E:T) are 3.3:1 (panel A) and 11:1 (panel B). All EL-4 non-specific targets were lysed at below 1.9% (data not shown).

Presence of a relationship was explored between adjuvant activity and the mol % of the active ingredient, β-D-Glc-(1,6)-β-D-Glc-archaeol, mixed with DPPG/cholesterol. Cholesterol was maintained constant at 20 mol % with DPPG added as required to balance increasing amounts of β-D-Glc-(1,6)-β-D-Glc-archaeol. Surprisingly, liposome formation upon hydration of DPPG/cholesterol (80/20, mol %) was improved by including β-D-Glc-(1,6)-β-D-Glc-archaeol up to 35 mol %. Hydration became more difficult at 60 mol % D-Glc-(1,6)-β-D-Glc-archaeol, and archaeosomes with 60 mol % of the synthetic glyco-archaeol increased in size during the removal of unentrapped antigen indicating instability (Table 11). Microscopic examination revealed that in contrast to the other preparations shown in Table 11 with exception of DPPG/Glc$_2$-A (65/35, mol %), archaeosomes containing 60 mol % D-Glc-(1,6)-β-D-Glc-archaeol began to convert from vesicles to non-vesicular structures within several days at 4° C. The loading of an antigen that was achieved in these archaeosome types is also shown in Table 11. Immunized mice developed CD8$^+$ T cell immune responses that were best at 15-45 mol % Glc$_2$-archaeol content (FIG. 5).

The need for cholesterol, and the optimal mol % cholesterol needed to achieve stability of archaeosomes containing 35 mol % D-Glc-(1,6)-β-D-Glc-archaeol was explored. Cholesterol was varied in each preparation from 0, 10, 20, 30 and 45 mol %. DPPG made up the balance of each preparation. Lipids were mixed in solvent and archaeosomes were loaded with the antigen OVA as described in methods. Archaeosomes formed in all cases upon hydrating at 35° C. However, when stored at refrigeration temperatures (4-6° C.) these synthetic archaeosomes with no cholesterol were unstable, converting to amorphous lipid debris and needle shaped crystals. This instability was avoided by inclusion of 10 mol % or more cholesterol. As cholesterol was increased to 45 mol % some instability became evident, as seen from the increase in size of this preparation (Table 11). The optimal cholesterol was therefore in the range of >10 to <45 mol %.

Figure 6:
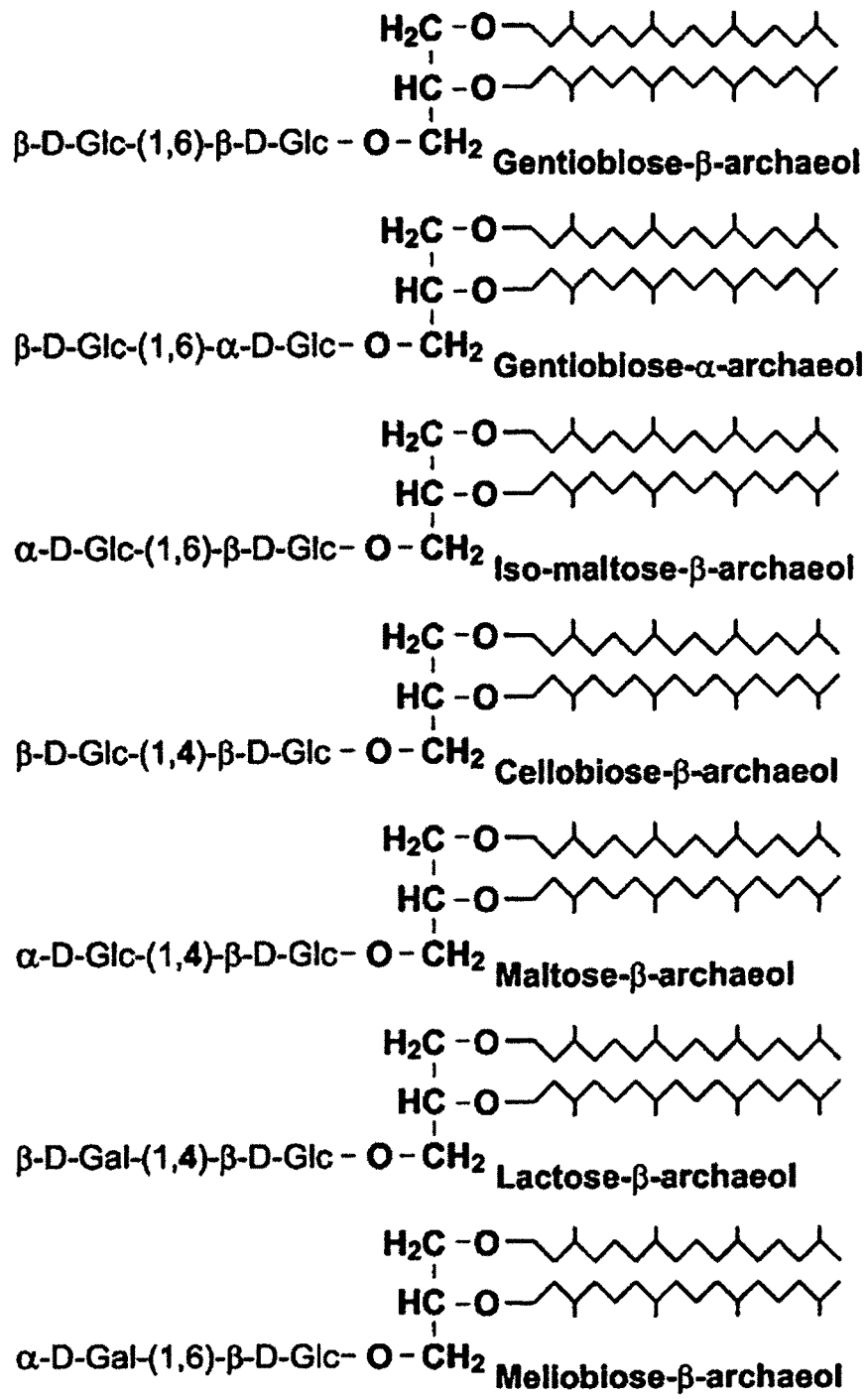
FIG. 6 illustrates the molecular structures of a series of synthetic disaccharide-archaeols.

Various disaccharide head groups were coupled to archaeol to form a series of new synthetic archaeal glycolipids (FIG. 6). These were formulated with antigen for animal trials, with lipids comprised of the various disaccharide-archaeols/DPPG/cholesterol (25/55/20, mol %). Average diameters and antigen loading properties are shown in Table 11. CTL activities in animals show importance for both carbohydrates to be glucose with 1-6 linkage preferred to 1-4 in the shorter term (FIG. 7A, 6 weeks). In the longer term (FIG. 7B, 12 weeks) CTL adjuvant activity was strong also for lactose-archaeol and melibiose-archaeol where sugars are linked gal-glc-archaeol. The preferred linkage configuration between the two glucose units was compared in FIG. 7C using synthetic isomaltose-archaeol (α-(1,6)) and gentiobiose-archaeol (β-(1,6)). CD8$^+$ T cell adjuvant activity was best in archaeosomes containing the synthetic diglucose-archaeol with β-(1,6) linkage, and this preference for a β-glc-glc linkage is seen also by comparison of gentiotriose-A and maltotriose-A (FIG. 7C). In contrast, antibody responses in mice were quite strong for isomaltose-A (α-(1,6)) archaeosomes, although preference was still for the β-(1,6) linkage (FIG. 7D).

Archaeosomes composed of synthetic β-D-Glc-(1,6)-β-D-Glc-(1,6)-β-D-Glc-(1,1)-archaeol/DPPG/cholesterol (35:45:20, mol %) were also stable and entrapped the antigen OVA similarly to the gentiobiose-archaeol archaeosomes (Table 11). Generally, three sugar moieties coupled to archaeol were preferred to two in terms of hydration ease and immune responses achieved. In one example, the Elispot assay revealed an antigen specific CD8$^+$ T cell response 6 weeks from first injection in mice immunized with antigen-containing gentiotriose-A/DPPG/cholesterol (25/55/20, mol %) to be 2 to 5 times higher than with gentiobiose-A/DPPG/cholesterol (25/55/20, mol %).

It is recognized that multiple receptor engagement on APCs may be achieved by including more than one type of glyco head group in an archaeosome adjuvant; for example, mannotriose- or mannotetraose archaeal lipid may target the macrophage mannose receptor (FIG. 3) combined with another glyco synthetic lipid with different targeting specificity, or archaetidylserine to target the phosphatidylserine receptor on dendritic cells.

Linkage α or β to the Lipid

Figure 8:
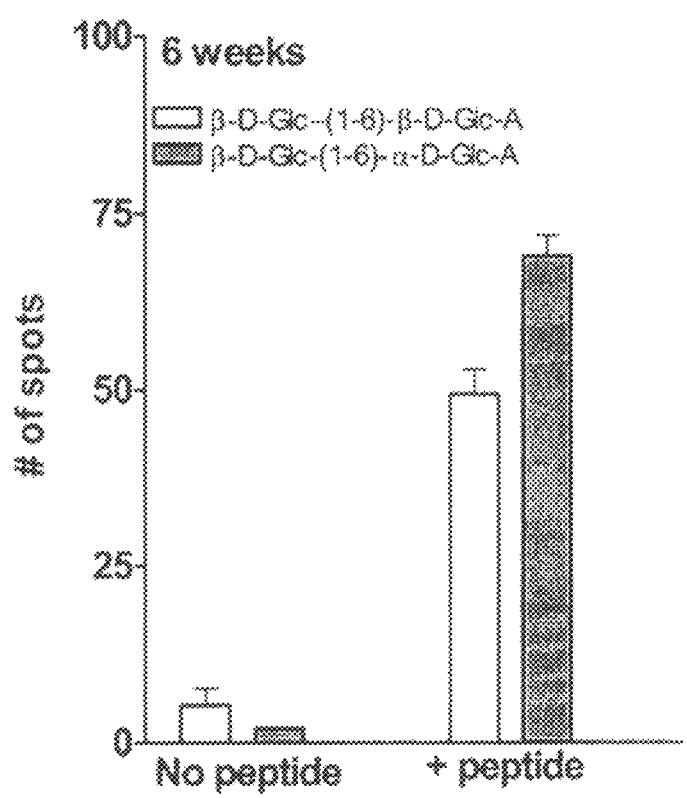
FIG. 8 compares the CD8$^+$ T cell adjuvant activity in mice similarly immunized with OVA-archaeosomes consisting of β-D-Glc-(1,6)-β-D-Glc-archaeol/DPPG/chol (35/35/30, mol %) and β-D-Glc-(1,6)-α-D-Glc-archaeol/DPPG/chol (35/35/30, mol %). Spleens were removed for the Elispot assays on week 6, post first injection.

Gentiobiose was linked in α and β configurations to the archaeol moiety (FIG. 6) to determine the influence of this aspect on adjuvant activity. Elispot assays revealed that both linkage configurations were active to adjuvant a CD8$^+$ T cell response (FIG. 8). Anti-OVA antibody titers in sera of mice (4/group) at 6 weeks post first injection were also comparable (12,216±8078 for β-linked and 10,126±4310 for α-linked).

Nature of the Anionic Lipid

Figure 9:
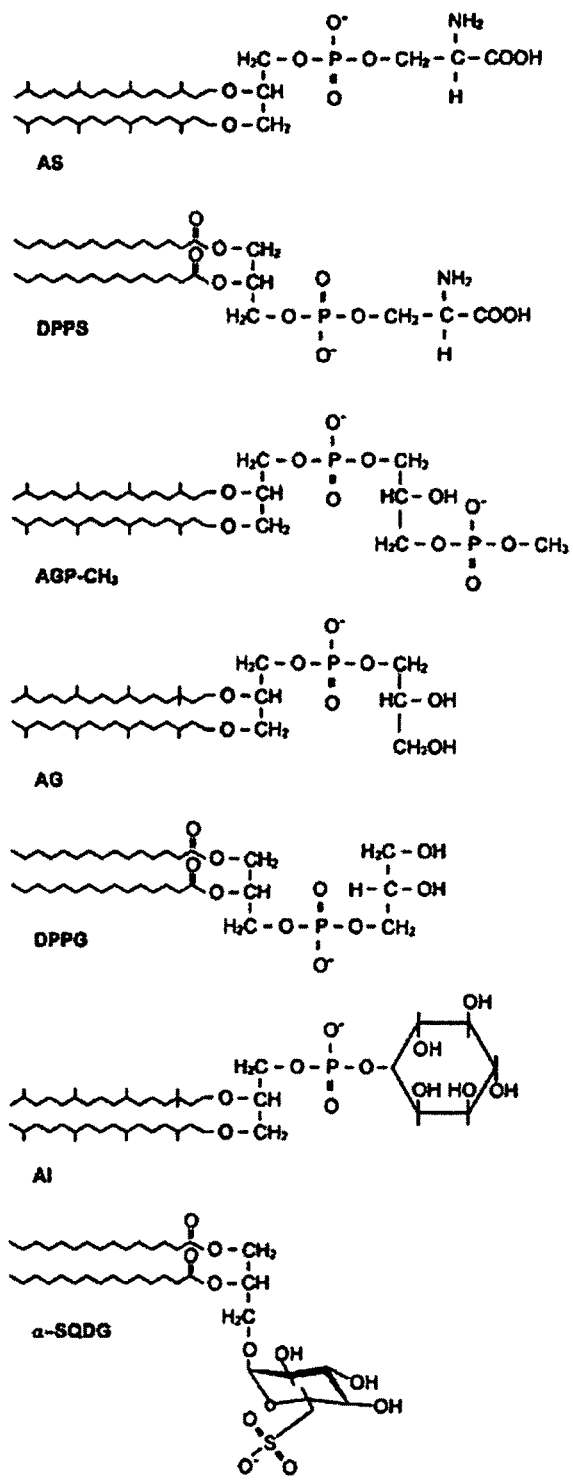
FIG. 9 shows the structures for several anionic archaeols as well as DPPS and DPPG used in synthetic glyco-archaeosome formulations.
Figure 10:
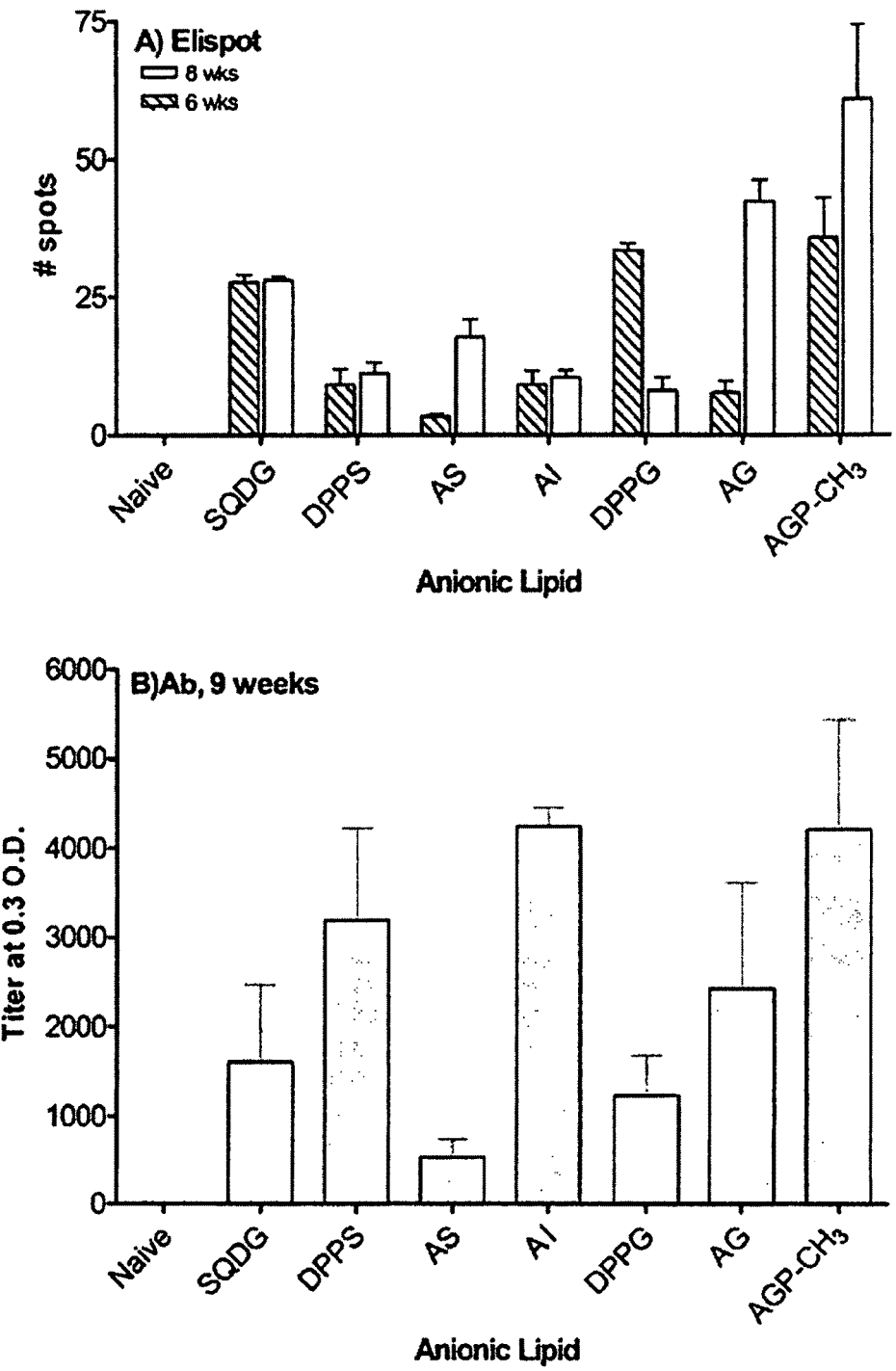
FIG. 10A shows the antigen specific CD8$^+$ T cell responses based on IFN-γ production (Elispot) in animals injected with the protein antigen entrapped in various synthetic archaeosomes comprised of antigen and gentiotriose archaeol (β-D-Glc-(1,6)-β-D-Glc-(1,6)-β-D-Glc-archaeol)/anionic lipid/cholesterol (35/35/30, mol %). Structures for the anionic lipids listed on the x-axis are shown in FIG. 9. Mice were injected subcutaneously on 0 and 3 weeks with 15 μg OVA entrapped in the various synthetic archaeosome compositions. Elispot assays were done using spleen cells taken on weeks 6 and 8, post first injection. Non-specific controls (no SIINFEKL peptide added) were below detection, except at 6 weeks with AG and AGP-CH$_3$ where small blank values were subtracted.
FIG. 10B shows anti-OVA antibody responses (IgG+IgM) in blood taken 9 weeks post first injection for mice in FIG. 10A.

An anionic lipid moiety improved the formulation and stability of synthetic-archaeol archaeosomes, so this aspect of the invention was explored in relation to adjuvant activity. Various anionic lipids (FIG. 9) formed stable archaeosomes that retained entrapped antigen when combined with synthetic gentiotriose-archaeol and cholesterol (Table 11). The degree of adjuvant activity of the various synthetic archaeosomes was influenced considerably by the nature of the anionic lipid (FIG. 10A). Best activity was noted for SQDG and archaetidylglycerols (AG and AGP-CH$_3$). The antigen-specific CD8$^+$ T cell response of synthetic gentiotriose-archaeol archaeosomes containing DPPG was transient, in contrast to that with archaeal anionic lipids wherein activity tended to increase from 6 to 8 weeks. Incorporating DPPE as the anionic lipid resulted in an Elispot showing 27% of the activity found for DPPG at 6 weeks (data not shown). These results show the importance and advantage to generate longer-term responses by use of synthetic archaeal lipids (to provide the anionic charge) versus other conventional lipids, with the exception of SQDG.

The nature of the anionic lipid that was incorporated into the synthetic archaeosomes also impacted on the antigen-specific antibody responses (FIG. 10B). FIGS. 10A and B show that the composition of the synthetic lipids used to make the synthetic archaeosomes can be used to direct the immune response towards either MHC class I or MHC class II immune responses, or to achieve high responses for both. For example, an archaetidylinositol favoured the antibody CD4$^+$ T cell response over the CD8$^+$ T cell response, and archaetidylglycerols as the anionic lipid resulted in high responses for both. DPPE at 35 mol % resulted in relatively low CD8$^+$ T cell activity, but was equivalent in antibody response to archaeosomes containing archaetidylglycerol (data not shown).

Replacement of Cholesterol by Synthetic Polar Caldarchaeols

Figure 11:
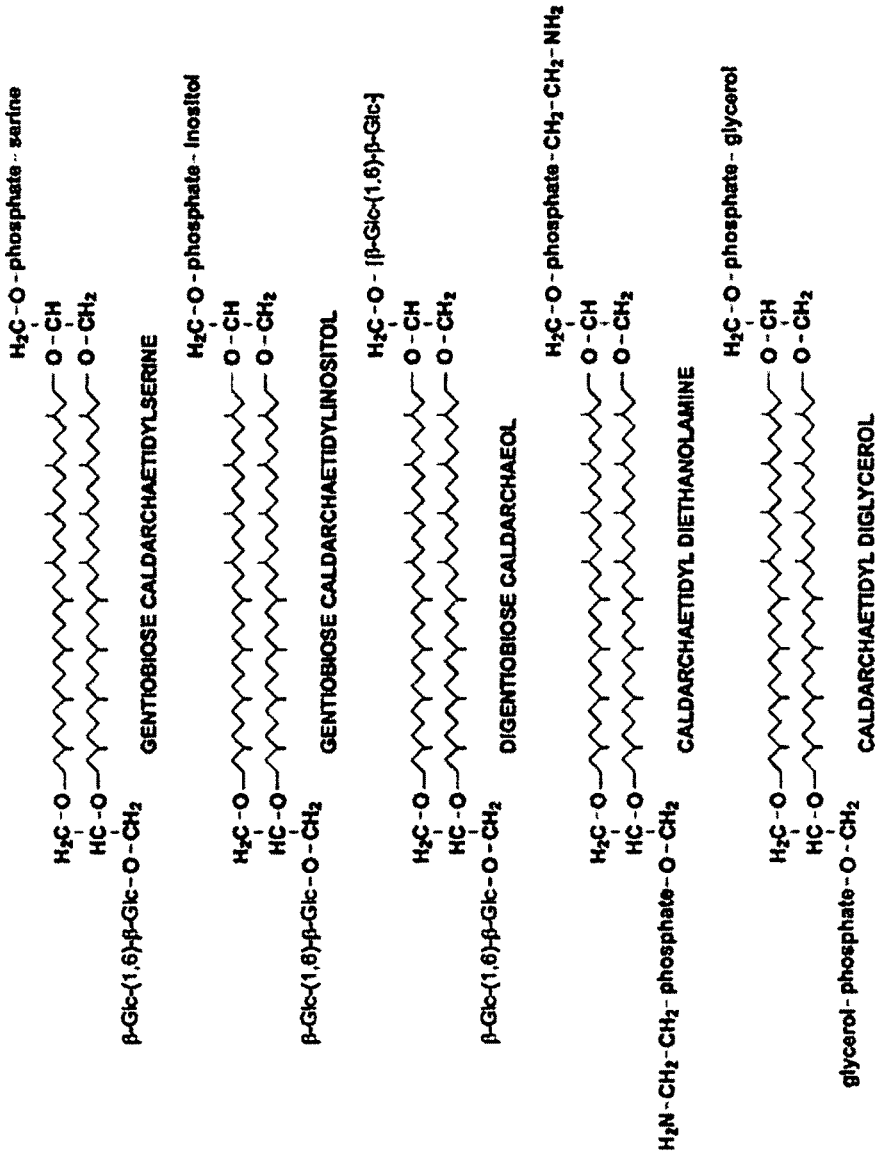
FIG. 11 illustrates the molecular structures of a selection of polar caldarchaeol lipids.

For stability and adjuvant activity synthetic archaeosomes preferably include at least three elements; namely, an appropriate synthetic glyco-moiety, an anionic moiety, and a stabilizer. One or more of these elements may be embodied in a single molecule. Stability of the synthetic glyco-archaeols may be achieved, for example, using cholesterol. Because cholesterol may itself oxidize and be undesirable in a product for human use, the possibility was explored to bypass the need for cholesterol by use of membrane stabilizing bipolar caldarchaeols. As a caldarchaeol bipolar lipid may be synthesized with all three elements; namely, one glyco head group, one anionic head group, and stability feature due to the caldarchaeol core lipid structure, archaeosomes were made using two such lipids (gentiobiose-caldarchaetidylinositol, and gentiobiose-caldarchaetidylserine) (FIG. 11). These archaeosomes comprised a single lipid combined with antigen and formed in good yield from each lipid, contrary to expectation based on inefficient archaeosome formation from the caldarchaeol-rich TPLs of *Thermoplasma* and *Sufolobus*. The average diameters and antigen loadings are shown in Table 11. It may be appreciated that combination of synthetic polar archaeol with synthetic polar caldarchaeol lipids may be used in the synthetic archaeosome formulation with antigen. Further, it may be appreciated that the 3 criteria listed above may be achieved to form stable archaeosomes with adjuvant activity by mixing two novel synthetic lipids, the first synthesized from caldarchaeol with 2 immuno-active head groups (gentiobiose example in FIG. 11), and the second with two head groups bearing an anionic charge (FIG. 11). The advantage to coupling the same head group to both free hydroxyl moieties of a caldarchaeol is to simplify synthesis. Similarly, it can be recognized that an archaeol may be chemically coupled to either a glyco group or anionic group and combined with a caldarchaeol synthesized to provide glyco or anionic groups to form an archaeosome adjuvant.

Figure 12:
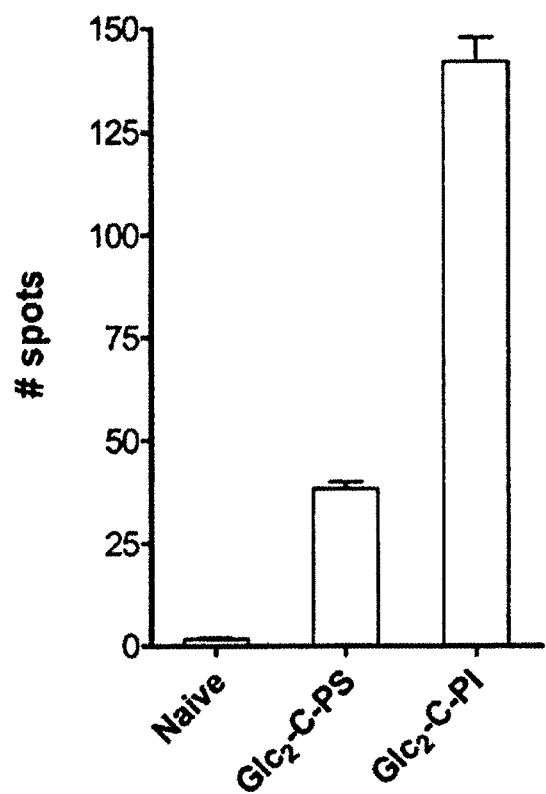
FIG. 12 illustrates antigen-specific CD8$^+$ T cell responses generated in animals immunized with archaeosomes comprised of a single caldarchaeol bipolar lipid and antigen. Strong adjuvant activity is shown for the gentiobiose caldarchaetidylinositol archaeosome that contrary to expectation (10) exceeds that of the gentiobiose caldarchaetidylserine archaeosome. The assay was performed on splenic cells taken 6 weeks post first injection.

Archaeosomes composed of a single bipolar caldarchaeol served as strong $CD8^+$ T cell adjuvants (FIG. 12). The data indicate that the anionic head group should preferably be phosphoinositol compared to phosphoserine and data in FIG. 10 further show a preference for phosphoglycerol versus either phosphoinositol or phosphoserine. The anti OVA antibody response in blood titre was from 16,151-17,960 for the $Glc_2$-C-PI archaeosome compared to only 2,592-2,600 for the $Glc_2$-C-PS archaeosome, again indicating importance for the proper selection of anionic head group and supporting the observation of higher antibody responses with archaeal lipids containing a phosphoinositol group.

Mucosal Responses

Secretory sIgA was found in faecal extracts of mice immunized with both caldarchaeol archaeosomes, although best responses occurred for phosphoinositol over phosphoserine as the anionic head group (Table 12). Anionic lipids giving activity in the gentiotriose-A compositions were DPPE, AG and AS. These results revealed that a sIgA mucosal response in mice to an antigen depended on the lipid composition of the synthetic archaeosome adjuvant.

Up-Regulation of Co-Stimulatory Molecules

Macrophages J774A.1 were incubated for 48 h with 25 µg of archaeosomes prior to staining and analysis by flow cytometry (Table 13). Compared to control cultures receiving either no stimulation or treatment with DPPG/chol (80/20, mol %) liposomes, expression of co-stimulatory molecules (CD80) on APCs were only up-regulated after exposure to $Glc_2$-archaeol/DPPG/Chol (45/35/20, mol %) and $Man_4$-archaeol/DPPG/Chol (45/35/20, mol %) archaeosomes. Immuno-activity was clearly ascribed to the synthetic glyco-archaeal lipid.

Protective Vaccines Against Cancer

Table 14 shows that the vaccine protective effect achieved against a B16 melanoma correlates with the magnitude of the immune response generated to the antigen OVA entrapped in various synthetic archaeosome adjuvants. Immune response to these synthetic archaeosome adjuvants was documented earlier in FIG. 7.

Protective Vaccines Against an Infectious Agent

Figure 13:
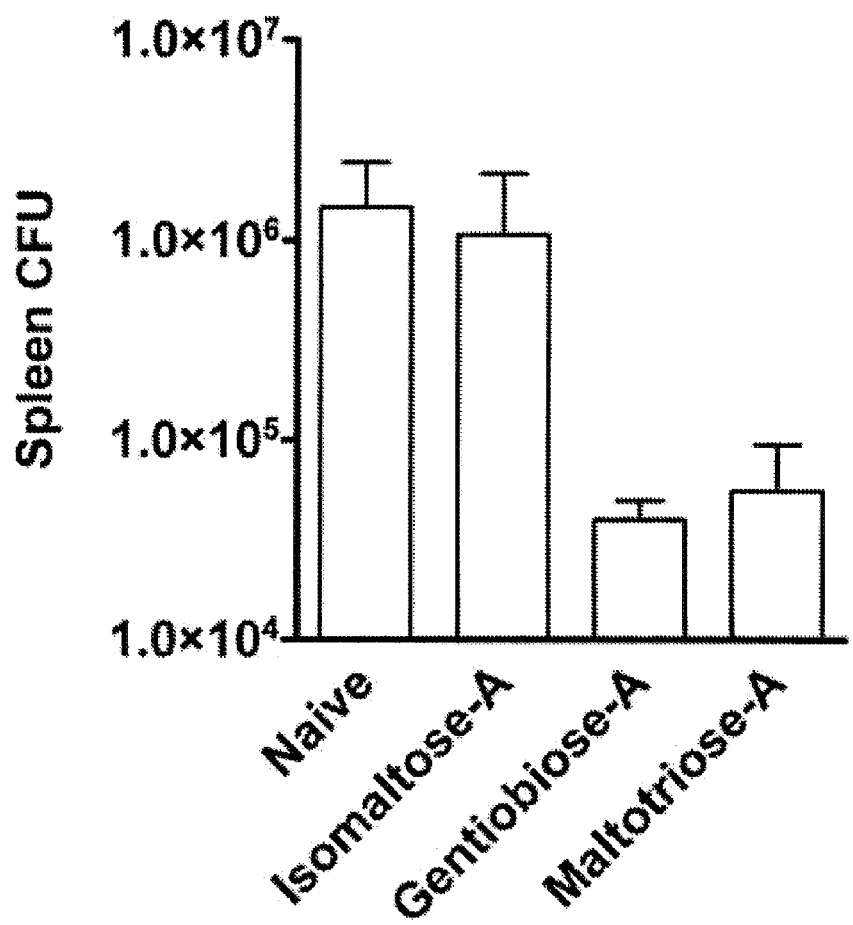
FIG. 13 illustrates protection against LM-OVA challenge after vaccination with OVA-adjuvant combinations. C57BL/6J mice were immunized on day 0 and 21 with 15 ug OVA entrapped in various synthetic archaeosomes composed of the respective synthetic glyco-archaeol/DPPG/chol (25/55/20, mol %). At 8 weeks, mice were challenged with $10^4$ intravenous dose of *Listeria monocytogenes* (LM)-OVA construct. Mice were euthanized 3 days later. Mean±SEM of splenic colony forming units (CFU) is shown for each group. Mice previously vaccinated with OVA in synthetic archaeosomes showed ~2 $\log_{10}$ protection compared to non-vaccinated naïve mice.

Mice vaccinated with synthetic archaeosomes containing an appropriate antigen were protected from infection (FIG. 13). Best protection occurred with gentiotriose-A archaeosomes, but maltotriose-A also caused striking protection. The lower $CD8^+$ T cell response observed for this latter archaeosome previously appears to be in part due to the shorter period from first injection to assay in FIG. 7C. In this example (FIG. 13), the antigen-specific $CD8^+$ T cell activity was measured in blood by tetramer assay and found to be about 30% as high in the maltotriose-A group compared to the gentiotriose-A group (data not shown). Isomaltose-A archaeosomes were less protective and produced lower $CD8^+$ T cell responses (FIG. 7C).

MATERIALS AND METHODS

Archaeal Core Lipids

*Halobacterium salinarum* ATCC 33170 was grown aerobically and the biomass extracted with chloroform/methanol/water to obtain the total lipids. TPL was obtained as the acetone insoluble lipids (29). This source was chosen to provide saturated archaeol as the sole lipid product following hydrolysis. In one instance 3 g of TPL was added to a 500-ml round bottom flask and the solvent removed. To the dried lipids 150 ml of 2.5% methanolic-HCL was added and reflux continued at 64-65° C. for 4 h while stirring magnetically. In another instance, equally good results were obtained by reflux for 1 h followed by a second 1 h reflux of the residue with fresh methanolic-HCl. Archaeol in the methanolic-HCl was partitioned into petroleum ether by mixing methanolic HCl/water/petroleum ether (30-65° C. fraction) in the ratio 93 ml/9.3 ml/93 ml. The ether was evaporated to yield the archaeol as light yellow oil. In some cases a further purification step was conducted. Silica gel G (Merck) was poured into a column (bed 20 cm×1.8 cm) in hexane. The archaeol fraction was loaded in hexane. Any neutral lipids present were eluted with hexane prior to recovering pure archaeol by elution with hexane/ethyl acetate=9:1 (v/v). The yield was 41-58% (wt basis) of starting TPL.

*Thermoplasma acidophilum* (ATTC culture 27658) was grown and lipids extracted as previously described (30). Methanolic-HCl hydrolysis and ether partitioning to recover caldarchaeol was done as described for archaeol, with yields of about 56% of the starting TPL (wt basis).

Synthetic Glyco-Archaeol Synthesis

Glyco-archaeols were synthesized as illustrated (FIG. 2) for α-D-Glc-(1,4)-α-D-Glc-(1,4)-β-D-Glc-(1,1)-archaeol and β-D-Glc-(1,6)-β-D-Glc-archaeol. Sequential addition of mannose residues to archaeol is shown also. A series of disaccharides attached to archaeol were made.

The oligomeric mannose structures were synthesized starting from known 2-O-acetyl protected monosaccharide donor which was prepared following Douglas et al. (6). Thus, archaeol was sequentially glycosylated to provide Man α-linked to archaeol, deacetylated and then either re-glycosylated or hydrogenated to produce 1 to 4 additional α1,2-linked mannoses. To prepare glucose linked structures the commercially available maltotriose [α-Glc-(1,4)-α-Glc-(1,4)-β-Glc-OH] was first peracetylated. The resulting peracetate was selectively deacetylated at the anomeric position and converted into its known trichloroacetimidate derivative (17, 18) and the archaeol glycosylated followed by deacetylation. To make a β-Glc-(1,6)-Glc building block the known 4,6-phenylboronated thioglycoside (5) was deboronated to the 4,6-diol. The diol was coupled with itself following the procedure developed by Huang et al. (11) and after acetylation and purification to give a disaccharide donor. This donor was used to directly glycosylate archaeol or to glycosylate the 4,6-diol of β-Glc-archaeol prepared by glycosylation followed by deboronation with the original Glc phenylboronate donor. Removal of the acetyl and benzoyl protecting groups yielded $Glc_2$- and $Glc_3$-oligomers of β-Glc-(1,6)-Glc attached β to archaeol. The disaccharide archaeol derivatives derived from maltose, iso-maltose, lactose, cellobiose and meliobiose were made by preparing the known 1-phenylthio derivatives (1, 20, 31) and glycosylating the archaeol using NIS/AgOTf or $NIS/BF_3/TFE_2$ conditions followed by removal of the acetyl protecting groups. The α-linked isomer of gentiobiose α-D-Glc-(1,6)-β-D-Glc-archaeol was made by coupling a glucose donor with a cleavable silyl protecting group at O-6 under conditions optimized to form the α-anomer. The resulting monomer was desilylated and glycosylated under standard conditions to give the protected disaccharide that was deprotected under standard conditions. Gentiobiose β-linked to both hydroxyls of caldarchaeol was made using the Glc$_2$ donor. All compounds were characterized by $^1$H and $^{13}$C NMR including $^1$H—$^1$H COSY and $^{13}$C—$^1$H COSY correlation experiments. As well 1D and 2D TOCSY experiments and 1D or 2D NOESY or ROESY experiments were used to confirm connectivities and make assignments as necessary. Also, positive ion MALDI MS of lipid containing species gave the expected ions typically (M+Na)$^+$ and often (M+K)$^+$ as well.

Procedure A

2R)-2,3-Bis[(3R,7R,11R)-3,7,11,15-tetramethyl-hexadecyloxy]propan-1-yl 2-O-acetyl-3,4,6-tri-O-benzyl-α-D-mannopyranoside (Man$_1$-A To a mixture of (2R)-2,3-Bis[(3R,7R,11R)-3,7,11,15-tetramethylhexadecyloxy]propan-1-ol (archaeol) (720 mg; 1.1 mmol), 2-O-acetyl-3,4,6-tri-O-benzyl-α-D-mannopyranosyl trichloroacetimidate (1.4 g; 2.2 mmol) and molecular sieves 4A° (3 g) was added CH$_2$Cl$_2$ (15 ml). After stirring at R.T. under an argon atmosphere for 1 h, triethylsilyltrifluoromethanesulfonate (25 μL; 0.11 mmol) was added and the stirring continued for 40 min. The reaction was quenched with diisopropylethylamine (100 μL). The whole reaction was adsorbed on silica gel and then purified by silica gel chromatography eluting with hexanes:ethyl acetate 9:1 to yield pure product as a viscous oil (0.58 g; 47%) plus some mixed fractions.

Procedure B

2R)-2,3-Bis[(3R,7R,11R)-3,7,11,15-tetramethyl-hexadecyloxy]propan-1-yl 3,4,6-tri-O-benzyl-α-D-mannopyranoside (Man$_1$-B Man$_1$-A (0.58 g; 0.51 mmol) was dissolved in a mixture of dry methanol (10 mL) and CH$_2$Cl$_2$ (2 mL). Then 1M NaOCH$_3$ (0.5 mL) was added and the stirring continued for 4 h. The reaction mixture was diluted with CH$_2$Cl$_2$ (150 mL) and washed 2× with NH$_4$Cl$_{aq}$ followed by saturated NaCl$_{aq}$. After drying with Na$_2$SO$_4$, filtration and evaporation the residue was purified by column chromatography on silica gel eluting with hexanes:ethyl acetate 5:1 to yield pure compound as a viscous oil (520 mg; 93%).

(2R)-2,3-Bis[(3R,7R,11R)-3,7,11,15-tetramethyl-hexadecyloxy]propan-1-yl 2-O-(2-O-acetyl-3,4,6-tri-O-benzyl-α-D-mannopyranosyl)-3,4,6-tri-O-benzyl-α-D-mannopyranoside (Man$_2$-A)

Man$_2$-A was prepared from Man$_1$-B using procedure A and purified by silica gel eluting with hexanes:ethyl acetate 9:1 followed by hexanes:ethyl acetate 85:15.

(2R)-2,3-Bis[(3R,7R,11R)-3,7,11,15-tetramethyl-hexadecyloxy]propan-1-yl 2-O-(3,4,6-tri-O-benzyl-α-D-mannopyranosyl)-3,4,6-tri-O-benzyl-α-D-mannopyranoside (Man$_2$-B)

Man$_2$-B was prepared from Man$_2$-A using procedure B and purified by silica gel eluting with hexanes:ethyl acetate 85:15.

(2R)-2,3-Bis[(3R,7R,11R)-3,7,11,15-tetramethyl-hexadecyloxy]propan-1-yl 2-O-(2-O-acetyl-3,4,6-tri-O-benzyl-α-D-mannopyranosyl)-2-O-(3,4,6-tri-O-benzyl-α-D-mannopyranosyl)-3,4,6-tri-O-benzyl α-D-mannopyranoside (Man$_3$-A)

Man$_3$-A was prepared from Man$_2$-B using procedure A and purified by silica gel eluting with hexanes:ethyl acetate 85:15.

(2R)-2,3-Bis[(3R,7R,11R)-3,7,11,15-tetramethyl-hexadecyloxy]propan-1-yl 2-O-(3,4,6-tri-O-benzyl-α-D-mannopyranosyl)-2-O-(3,4,6-tri-O-benzyl-α-D-mannopyranosyl)-3,4,6-tri-O-benzyl-α-D-mannopyranoside (Man$_3$-B)

Man$_3$-B was prepared from Man$_3$-A using procedure B and purified by silica gel eluting with hexanes:ethyl acetate 85:15.

(2R)-2,3-Bis[(3R,7R,11R)-3,7,11,15-tetramethyl-hexadecyloxy]propan-1-yl 2-O-(2-O-acetyl-3,4,6-tri-O-benzyl-α-D-mannopyranosyl)-2-O-(3,4,6-tri-O-benzyl-α-D-mannopyranosyl)-2-O-(3,4,6-tri-O-benzyl-α-D-mannopyranosyl)-3,4,6-tri-O-benzyl α-D-mannopyranoside (Man$_4$-A)

Man$_4$-A was prepared from Man$_3$-B using procedure A and purified by silica gel eluting with hexanes:ethyl acetate 85:15.

(2R)-2,3-Bis[(3R,7R,11R)-3,7,11,15-tetramethyl-hexadecyloxy]propan-1-yl-2-O-3,4,6-tri-O-benzyl-α-D-mannopyranosyl-2-O-(3,4,6-tri-O-benzyl-α-D-mannopyranosyl)-2-O-(3,4,6-tri-O-benzyl-α-D-mannopyranosyl)-3,4,6-tri-O-benzyl-α-D-mannopyranoside (Man$_4$-B)

Man$_4$-B was prepared from Man$_4$-A using procedure B and purified by silica gel eluting with hexanes:ethyl acetate 85:15.

(2R)-2,3-Bis[(3R,7R,11R)-3,7,11,15-tetramethyl-hexadecyloxy]propan-1-yl 2-O-(2-O-acetyl-3,4,6-tri-O-benzyl-α-D-mannopyranosyl)-2-O-(3,4,6-tri-O-benzyl-α-D-mannopyranosyl)-2-O-(3,4,6-tri-O-benzyl-α-D-mannopyranosyl)-3,4,6-tri-O-benzyl α-D-mannopyranoside (Man$_4$-A)

Man$_4$-A was prepared from Man$_3$-B using procedure A and purified by silica gel eluting with hexanes:ethyl acetate 85:15.

(2R)-2,3-Bis[(3R,7R,11R)-3,7,11,15-tetramethyl-hexadecyloxy]propan-1-yl-2-O-3,4,6-tri-O-benzyl-α-D-mannopyranosyl-2-O-(3,4,6-tri-O-benzyl-α-D-mannopyranosyl)-2-O-(3,4,6-tri-O-benzyl-α-D-mannopyranosyl)-3,4,6-tri-O-benzyl-α-D-mannopyranoside (Man$_4$-B)

Man$_4$-B was prepared from Man$_4$-A using procedure B and purified by silica gel eluting with hexanes:ethyl acetate 85:15.

(2R)-2,3-Bis[(3R,7R,11R)-3,7,11,15-tetramethyl-hexadecyloxy]propan-1-yl 2-O-(2-O-acetyl-3,4,6-tri-O-benzyl-α-D-mannopyranosyl)-2-O-(3,4,6-tri-O-benzyl-α-D-mannopyranosyl)-2-O-(3,4,6-tri-O-benzyl-α-D-mannopyranosyl)-2-O-(3,4,6-tri-O-benzyl-α-D-mannopyranosyl)-3,4,6-tri-O-benzyl α-D-mannopyranoside (Man$_5$-A)

Man$_5$-A was prepared from Man$_4$-B using procedure A and purified by silica gel eluting with hexanes:ethyl acetate 85:15.

(2R)-2,3-Bis[(3R,7R,11R)-3,7,11,15-tetramethylhexadecyloxy]propan-1-yl-2-O-(3,4,6-tri-O-benzyl-α-D-mannopyranosyl)-2-O-(3,4,6-tri-O-benzyl-α-D-mannopyranosyl)-2-O-(3,4,6-tri-O-benzyl-α-D-mannopyranosyl)-2-O-(3,4,6-tri-O-benzyl-α-D-mannopyranosyl)-3,4,6-tri-O-benzyl-α-D-mannopyranoside (Man$_5$-B)

Man$_5$-B was prepared from Man$_5$-A using procedure B and purified by silica gel eluting with hexanes:ethyl acetate 75:25.

Procedure C

2R)-2,3-Bis[(3R,7R,11R)-3,7,11,15-tetramethylhexadecyloxy]propan-1-yl α-D-mannopyranoside (Man$_1$-C Man$_1$-B (100 mg; 0.051 mmol) was dissolved in ethyl acetate (10 mL) and after purging with argon Pd(OH)$_2$/C (Pearlman's catalyst) (150 mg) was added and the mixture hydrogenated using a Parr apparatus at 50 p.s.i. of H$_2$ with shaking for 64 h. The catalyst was removed by filtration through a bed of celite and was well washed with ethyl acetate and methanol. The combined filtrates were evaporated and then purified by silica gel chromatography eluting with ethyl actetate:methanol:water 7:1:1 to yield a waxy solid (62 mg, 83%).

2R)-2,3-Bis[(3R,7R,11R)-3,7,11,15-tetramethylhexadecyloxy]propan-1-yl 2-O-(α-D-mannopyranosyl) α-D-mannopyranoside (Man$_2$-C Man$_2$-C was prepared from Man$_2$-B using procedure C.

(2R)-2,3-Bis[(3R,7R,11R)-3,7,11,15-tetramethylhexadecyloxy]propan-1-yl 2-O-(α-D-mannopyranosyl)-2-O-(α-D-mannopyranosyl)-α-D-mannopyranoside (Man$_3$-C)

Man$_3$-C was prepared from Man$_3$-B using procedure C.

(2R)-2,3-Bis[(3R,7R,11R)-3,7,11,15-tetramethylhexadecyloxy]propan-1-yl 2-O-(α-D-mannopyranosyl)-2-O-(α-D-mannopyranosyl)-2-O-(α-D-mannopyranosyl)-α-D-mannopyranoside (Man$_4$-C)

Man$_4$-C was prepared from Man$_4$-B using procedure C.

(2R)-2,3-Bis[(3R,7R,11R)-3,7,11,15-tetramethylhexadecyloxy]propan-1-yl 2-O-(α-D-mannopyranosyl)-2-O-(α-D-mannopyranosyl)-2-O-(α-D-mannopyranosyl)-α-D-mannopyranoside (Man$_5$-C)

Man$_5$-C was prepared from Man$_5$-B using procedure C.

Ethyl 6-O-(4,6-di-O-acetyl-2,3-di-O-benzoyl-β-D-glucopyranosyl)-4-O-acetyl-2,3-di-O-benzoyl-β-D-gluco-1-thiopyranoside (Glc$_2$ donor)

To ethyl 2,3-di-O-benzoyl-β-D-gluco-1-thiopyranoside (3.0 g; 6.93 mmol) [prepared by deboronylation with IRA743 resin see Glc$_1$-A' $^1$H NMR CDCl$_3$ 7.93 d 4 (J$_{11,11}$ 6.8) Bz$_o$, 7.49 m 2 Bz$_p$, 7.35 m 4 Bz$_m$, 5.42 m (2, H-2, H-3), 4.73 d (1, J$_{1,2}$ 9.8, H-1), 4.00 dd (1, J$_{5,6}$ 3.4, J$_{66}$12.1, H-6), 3.96 brt (1, J$_{3,4}$=J$_{4,5}$ 9.4, H-4), 3.87 dd (1, J$_{5,6}$4.9, H-6'), 3.60 ddd (1, H-5), 3.17 brs (OH), 2.73 m (2, SCH$_2$), 1.25 t (3, J$_{HH}$ 7.2, SCH$_2$CH$_3$)] and molecular sieves 4A° (3 g) was added CH$_2$Cl$_2$ (30 mL) and the mixture cooled in a dry ice acetone bath (bath T about −78° C.) under an atmosphere of argon. To this mixture was added p-toluenesulfenylchloride (667 µL; 4.6 mmol) and silver triflluoromethanesulfonate (1.188 g; 4.6 mmol) and the mixture stirred at this T for 1 h. The mixture was then transferred to a dry ice acetonitrile bath (bath T about −45° C.) and the mixture stirred for 1.75 h. The reaction was quenched with diisopropylethylamine (1 mL), filtered, followed by rinsing with CH$_2$Cl$_2$ and CH$_2$Cl$_2$:ethyl acetate 50:50, followed by concentration of the combined filtrates. The residue was purified by chromatography on silica gel eluting with ethyl acetate:hexanes:CH$_2$Cl$_2$ 6:3:1 to yield a viscous oil (1.55 g). The product is the lowest R$_f$ spot of the two most prevalent products. This oil was dissolved in pyridine (15 mL) and cooled in an ice bath under an atmosphere of argon, and acetic anhydride (7.5 mL) was added. The mixture was left to stir and warm to R.T. overnight. After evaporation the residue was purified by medium pressure liquid chromatography on silica gel eluting with hexanes:ethyl acetate:CH$_2$Cl$_2$ 6:3:1 to yield an amorphous white solid (1.2 g; 37%); $^1$H NMR CDCl$_3$ 7.93 m (8 Bz$_o$, 7.49), m (4 Bz$_p$), 7.35 m (8 Bz$_m$), 5.65 t (1, J$_{3,4}$ 9.4, H-3$^I$), 5.59 t (1, J$_{3,4}$ 9.5, H-3$^{II}$), 5.44 dd (1, J$_{2,3}$ 10.0, H-2$^{II}$), 5.37 t (1, J$_{4,5}$ 9.7, H-4$^{II}$), 5.33 dd (1, J$_{2,3}$ 10.0, H-2$^I$), 5.08 t (1, J$_{4,5}$ 9.7, H-4$^I$), 4.89 d (1, J$_{1,2}$ 7.9, H-1$^{II}$), 4.57 d (1, J$_{1,2}$ 10.0, H-1$^I$), 4.37 dd (1, J$_{5,6}$ 5.0, J$_{66}$12.3, H-6$^{II}$), 4.21 dd (1, J$_{5,6}$2.1, H-6$^{II}$), 3.95 brd (1, H-6$^I$), 3.88 ddd (1, H-5$^{II}$), 3.82 m (1, H-5$^I$), 3.75 dd (1, J$_{5,6}$7.3, J$_{6,6}$11.1, H-6$^I$), 2.51 m (2, SCH$_2$), 2.14, 1.94, 1.92 3×s (3, Ac CH$_3$), 1.05 t (3, J$_{HH}$ 7.2, SCH$_2$CH$_3$); $^{13}$C NMR CDCl$_3$ 170.7, 169.7, 169.4 (3×Ac C=O), 165.8, 165.6, 165.1 (2) (4×Bz C=O), 133.4, 133.35, 133.28, 133.2 (4×Bz$_p$), 129.8 (Bz$_m$), 129.2, 129.1, 128.80, 128.76 (4×Bz$_{ip}$), 128.4 (Bz$_o$), 101.0 (C-1$^{II}$), 83.3 (C-1$^I$), 77.7 (C-5$^I$), 74.1 (C-3$^I$), 73.0 (C-3$^{II}$), 72.2 (C-5$^{II}$), 71.6 (C-2$^{II}$), 70.4 (C-4$^I$), 69.1 (C-4$^{II}$), 68.41 (C-6$^I$), 68.36 (C-4$^I$), 61.9 (C-6$^{II}$), 24.0 (SCH$_2$), 20.8, 20.54, 20.52 (3, Ac CH$_3$), 14.7 (SCH$_2$CH$_3$); MALDI MS (M+Na)$^+$951.4, 967.3 (M+K)$^+$.

(2R)-2,3-Bis[(3R,7R,11R)-3,7,11,15-tetramethylhexadecyloxy]propan-1-yl 6-O-(4,6-di-O-acetyl-2,3-di-O-benzoyl-β-D-glucopyranosyl)-4-O-acetyl-2,3-di-O-benzoyl-β-D-glucopyranoside (Glc$_2$-A)

To Glc$_2$ donor (236 mg, 0.255 mmol) and molecular sieves 4A° was added CH$_2$Cl$_2$ (2 mL) and the mixture cooled in a dry ice methanol bath (bath T about −60° C.) under an atmosphere of argon. To this mixture was added p-toluenesulfenylchloride (37 µL; 0.255 mmol) and silver trifluoromethanesulfonate (65 mg; 0.255 mmol) and the mixture stirred at this T for 1 h. To this mixture was added archaeol (111 mg; 0.17 mmol) in CH$_2$Cl$_2$ (1.5 mL). After 10 min the bath was removed and the temperature allowed to rise. After 40 min the reaction was quenched with diisopropylethylamine (0.1 mL), filtered, followed by rinsing with CH$_2$Cl$_2$ and CH$_2$Cl$_2$:ethyl acetate 50:50, followed by concentration of the combined filtrates. The residue was purified by chromatography on silica gel eluting with hexanes:ethyl acetate:CH$_2$Cl$_2$ 7:2:1 to yield pure Glc$_2$-A as a viscous oil (161 mg; 64%).

Modified Procedure B

2R)-2,3-Bis[(3R,7R,11R)-3,7,11,15-tetramethylharadecyloxy]propan-1-yl 6-O-(β-D-glucopyranosyl)-β-D-glucopyranoside (Glc$_2$-A Glc$_2$-A (150 mg; 0.099 mmol) was dissolved in dry methanol (10 mL) and CH$_2$Cl$_2$ (5 mL). To this solution was added 1M NaOCH$_3$ (0.75 mL) and stirring continued for 16 h at R.T. The mixture was cooled in an ice bath and neutralized with RexynH$^+$ that had been washed with water and methanol. The solids were removed by filtration and washed with methanol. The combined filtrates were evaporated to yield pure Glc$_2$-B (95 mg; 98%) (23).

2R)-2,3-Bis[(3R,7R,11R)-3,7,11,15-tetramethyl-hexadecyloxy]propan-1-yl 2,3-di-O-benzoyl-β-D-glucopyranoside (Glc$_1$-A'

Ethyl 2,3-di-O-benzoyl-4,6-phenylboranyl-β-D-gluco-1-thiopyranoside (5) (125 mg; 0.24 mmol) was activated and reacted with archaeal (105 mg; 0.16 mmol) as described above for Glc$_2$A. The crude product was treated with IRA-743 resin (about 10 g) that had been soaked and rinsed extensively with acetonitrile in acetonitrile (about 25 mL) by shaking overnight. The resin was removed by filtration, rinsed with CH$_2$Cl$_2$ and acetonitrile, and the combined filtrates evaporated to dryness. The residue was purified by silica gel chromatography eluting with hexanes:ethyl acetate:CH$_2$Cl$_2$ 7:2:1 to yield pure Glc$_1$-A' as a viscous oil (67 mg; 41%).

(2R)-2,3-Bis[(3R,7R,11R)-3,7,11,15-tetramethyl-hexadecyloxy]propan-1-yl 6-O-(4,6-di-O-acetyl-2,3-di-O-benzoyl-β-D-glucopyranosyl)-6O-(4-O-acetyl-2,3-di-O-benzoyl-β-D-glucopyranosyl)-2,3-di-O-benzoyl-β-D-glucopyranoside (Glc$_3$-A)

Glc$_2$ donor (92 mg, 0.099 mmol) was activated as for Glc$_2$-A above and reacted with Glc$_1$-A' (67 mg; 0.066 mmol) for 2 h in a dry ice acetonitrile bath (bath T about −45° C.). The residue was purified by silica gel chromatography eluting with hexanes:ethyl acetate:CH$_2$Cl$_2$ 7:2:1 to yield pure Glc$_3$-A as a waxy solid (90 mg; 72%).

2R)-2,3-Bis[(3R,7R,11R)-3,7,11,15-tetramethyl-hexadecyloxy]propan-1-yl 6-O-(β-D-glucopyrano-syl)-6O-(β-D-glucopyranosyl)-β-D-glucopyranoside (Glc$_3$-B The acyl groups were removed from Glc$_3$-A (80 mg; 0.042 mmol) using modified procedure B. TLC analysis of the product indicated an unidentified impurity so the product was purified by preparative TLC eluting with CHCl$_3$:CH$_3$OH:CH$_3$COOH:H$_2$O 85:22.5:10:4 to yield pure Glc$_3$-B as a waxy solid (40 mg; 83%).

(2R)-2,3-Bis[(3R,7R,11R)-3,7,11,15-tetramethyl-hexadecyloxy]propan-1-yl 4-O-(2,3,4,6-tetra-O-α-D-glucopyranosyl)-4O-(2,3,6-tri-O-acetyl-α-D-glucopyranosyl)-2,3,6-tri-O-acetyl-β-D-glucopyranoside (Glc$_3$M-A)

To known (17, 18) 4-O-(2,3,4,6-tetra-O-α-D-glucopyranosyl)-4-O-(2,3,6-tri-O-acetyl-α-D-glucopyranosyl)-2,3,6-tri-O-acetyl-β-D-glucopyranosyl trichloroacetimidate (280 mg; 0.29 mmol), 4 molecular sieves (300 mg) and archaeol (78 mg; 0.12 mmol) was added CH$_2$Cl$_2$ (3 mL) and the mixture stirred for 1 h at R.T. under an atmosphere of argon. To this was added triethylsilyltrifluoromethanesulfonate (3 μL; 0.013 mmol) and the mixture stirred for 40 min when TLC in hexanes:ethyl acetate 1:1 R$_f$=0.5 indicated the reaction was complete. The reaction was quenched with diisopropylethylamine (10 μL), filtered with rinsing with CH$_2$Cl$_2$. The combined filtrates were concentrated and the residue purified by silica gel chromatography eluting with hexanes:ethyl acetate 2:1 to yield pure Glc$_2$M-A as a waxy solid (99 mg; 53%).

2R)-2,3-Bis[(3R,7R,11R)-3,7,11,15-tetramethyl-hexadecyloxy]propan-1-yl 4-O-(α-D-glucopyrano-syl)-4O-(α-D-glucopyranosyl)-β-D-glucopyranoside (Glc$_3$M-B Glc$_3$M-A was deacetylated following modified procedure B and purifed by silica gel chromatography eluting with CHCl$_3$:CH$_3$OH:H$_2$O 10:3:0.3 to yield pure Glc$_3$M-B.

Ethyl2,3,4-tri-O-benzyl-6-O-(t-butyldiphenylsilyl)-α/β-D-gluco-1-thiopyranoside (1)

Ethyl 2,3,4-tri-O-benzyl-α/β-D-gluco-1-thiopyranoside (7) (1.13 g, 2.21 mmol) was dissolved in CH$_2$Cl$_2$ (15 mL) and cooled in an ice bath under an argon atmosphere. To this was added imidazole (468 mg, 4.5 eq.) followed by t-butyldiphenylchlorosilane (0.894 mL, 1.5 eq) and the mixture allowed to stir and to warm to room temperature over 16 h. The reaction mixture was concentrated and the residue purified by silica gel chromatography eluting with CH$_2$Cl$_2$ followed by 1% t-butylmethylether in CH$_2$Cl$_2$ to yield 1 as a α/β (1:0.46) mixture: $^1$H NMR CDCl$_3$ 7.76-7.65 m (ArH), 7.41-7.24 m (ArH), 7.15 m (ArH), 5.45 d (J$_{1,2}$ 5.3, H-1$^α$), 4.94-4.58 m (BnCH$_2$), 4.48 d (J$_{1,2}$ 9.7, H-1$^β$), 4.13 m (H-5$^α$), 3.92-3.80 m (H-2$^α$, H-3$^α$, H-6$^α$, H-6'$^α$, H-6$^β$, H-6'$^β$), 3.75 t (J$_{4,5}$ 9.1, H-4$^β$), 3.67 t (J$_{3,4}$ 8.7, H-3$^β$), 3.57 t (J$_{3,4}$ 9.8, J$_{4,5}$ 9.9, H-4$^α$), 3.47 dd (J$_{2,3}$ 9.4, H-2$^β$), 3.37 m (H-5$^β$), 2.74 m (CH$_2$S$^α$), 2.52 (CH$_2$S$^β$), 1.32 t (J 7.6, CH$_3$CH$_2$S$^α$), 1.25 (J 7.6, CH$_3$CH$_2$S$^β$), 1.04, 1.02 2×s (CH$_3$ t-butyl); $^{13}$C NMR CDCl$_3$ 138.7, 138.3, 138.0 (3×Bn$_{ip}$$^α$), 138.4, 138.14, 138.10 (3×Bn$_{ip}$$^β$), 135.9, 135.8, 135.6 (Ph$_p$), 133.6, 133.2 (Ph$_{ip}$$^α$), 134.8, 133.1 (Ph$_{ip}$$^β$), 129.5 (m ArC), 128.5-127.5 (ArC), 86.7 (C-3$^β$), 84.4 (C-1$^β$), 82.7 (C-3$^α$), 82.2 (C-1$^α$), 81.9 (C-2$^β$), 80.0 (C-2$^α$), 79.9 (C-5$^β$), 77.72 (C-4$^β$), 77.69 (C-4$^α$), 75.91, 75.86, 75.5, 75.15, 75.1, 72.3 (BnCH$_2$), 71.9 (C-5$^α$), 63.0 (C-6$^α$), 62.8 (C-6$^β$), 34.7, 31.6 (CCH$_3$ t-butyl), 26.8 (CH$_3$ t-butyl), 24.3 (CH$_2$S$^β$), 23.2 (CH$_2$S$^α$), 15.1 (CH$_2$CH$_3$S$^β$), 14.6 (CH$_2$CH$_3$S$^α$); MALDI MS (M+H)$^+$733.5, (M+Na)$^+$755.5.

(2R)-2,3-Bis[(3R,7R,11R)-3,7,11,15-tetramethyl-hexadecyloxy]propan-1-yl 2,3,4-tri-O-benzyl-6-O-(t-butyldiphenylsilyl)-α-D-glucopyranoside (2) and (2R)-2,3-Bis[(3R,7R,11R)-3,7,11,15-tetramethyl-hexadecyloxy]propan-1-yl 2,3,4-tri-O-benzyl-α-D-glucopyranoside (3)

Archaeol (140 mg; 0.21 mmol) and (1, 236 mg, 1.5 eq.) were dissolved in CH$_2$Cl$_2$ (2.6 mL) and cooled in an ice bath under an argon atmosphere along with powdered 4 Å molecular sieves (300 mg). To this was added N-selenophenyl phthalimide (116 mg, 1.8 eq.) followed by trifluoromethanesulfonic acid (32 μL, 1.6 eq.) and the stirring continued for 3 h. The reaction was quenched with diisopropylethylamine (excess) and the mixture filtered and rinsed with CH$_2$Cl$_2$. The organic layers were concentrated and the residue purified by silica gel chromatography eluting with CH$_2$Cl$_2$:cycloC$_6$H$_{12}$:t-butylmethylether 49:49:2 to yield a mixture of 2 and the α-anomer of 1. This mixture was dissolved in tetrahydrofuran (4 mL) and a 1M solution of tetrabutylammonium fluoride in THF (400 μL) was added and the resulting mixture heated at 50° C. for 16 h under an atmosphere of argon. The reaction mixture was concentrated and the residue purified by silica gel chromatography eluting with CH$_2$Cl$_2$:cycloC$_6$H$_{12}$:t-butylmethylether 48:48:4 to yield 3 (108 mg; 48%). A small amount of 2 was repurified by preparative TLC CH$_2$Cl$_2$:cycloC$_6$H$_{12}$:t-butylmethylether 48:48:4 for an analytical sample. $^1$H NMR CDCl$_3$ 7.69 brd (2 Ph$_o$), 7.62 brd (2 Ph$_o$), 7.41-7.24 m (16 ArH), 7.16 m (4 Ph$_m$), 4.97-4.62 m (6, BnCH$_2$), 4.88 d (1, J$_{1,2}$ 4.8, H-1), 4.00 brt (1, H-3), 3.88 m (2, H-6, H-6'), 3.76 m (1, H-5), 3.67-3.49 m (9, H-2, H-4, CH$_2$O, CH$_2$O, CHO, OCH$_2$), 3.43 brt (2, OCH$_2$) 1.62-1.48 m (6, CH, CH$_2$), 1.38-1.22 m (42, CH, CH$_2$), 0.88-0.78 m (30, CH$_3$); MALDI MS (M+Na)$^+$ 1346.0, (M+K)$^+$ 1361.9. 3 $^1$H NMR CDCl$_3$ 7.40-7.24 m (15 ArH), 4.97 d (1, J$_{H,H}$ 11.8, BnCH$_2$), 4.89 d (1, J$_{H,H}$ 11.1, BnCH$_2$), 4.81 d (1, J$_{H,H}$ 11.8, BnCH$_2$), 4.80 d (1, J$_{1,2}$ 3.8, H-1), 4.71 q (2, BnCH$_2$), 4.65 d (1, J$_{H,H}$ 11.1, BnCH$_2$), 4.00 brt (1, J$_{3,4}$ 9.1, H-3), 3.81 dd (1, J$_{5,6}$ 2.3, J$_{6,6'}$ 12.3, H-6), 3.76 m (1, H-5), 3.69 m (1, H-6'), 3.67-3.45 m (9, CH$_2$O, CH$_2$O, CHO, OCH$_2$, H-4, H-2), 1.62-1.48 m (6, CH, CH$_2$), 1.38-1.22 m (42, CH, CH$_2$), 0.88-0.78 m (30, CH$_3$); $^{13}$C NMR CDCl$_3$ 138.8, 138.34, 138.31 (3×Bn$_{ip}$), 128.4-127.6 (ArC), 97.2 (C-1), 81.9 (C-3), 80.2 (C-2), 77.8 (CHO), 77.2 (C-4), 76.7, 75.6, 72.9 (3×BnCH$_2$), 70.8 (C-5, OCH$_2$), 70.6 (OCH$_2$), 69.0 (CH$_2$O), 67.9 (CH$_2$O), 61.9 (C-6), 39.4, 37.6, 37.52, 37.47, 37.44, 37.29, 37.2, 36.7 (CH$_2$), 32.8, 30.0, 29.8, 28.0 (CH), 24.8, 24.5, 24.4 (CH$_2$), 19.75, 19.68 (CH$_3$); MALDI MS (M+Na)$^+$ 1084.87.

(2R)-2,3-Bis[(3R,7R,11R)-3,7,11,15-tetramethyl-hexadecyloxy]propan-1-yl 6-O-[2,3,4,6-tetra-O-ben-zoyl-β-D-glucopyranosyl]-2,3,4-tri-O-benzyl-α-D-glucopyranoside (4)

Alcohol (3, 51 mg; 0.047 mmol) and 2,3,4,6-tetra-O-benzoyl-α-D-glucopyranosyl trichloroacetimidate (52 mg; 1.5 eq) were dissolved in CH$_2$Cl$_2$ (2.5 mL) along with powdered 4 Å molecular sieves (100 mg) and the mixture cooled in an ice bath under an atmosphere of argon. To this mixture BF$_3$ etherate (6 µL, 1 eq.) was added and the stirring continued for 2 h. The reaction was quenched with excess diisopropylethylamine, filtered and concentrated. The residue was purified by silica gel chromatography eluting with 2.5% acetone in toluene to yield 4 (17 mg; 22%). $^1$H NMR CDCl$_3$ 7.92 brd (2, J$_{H,H}$ 7.2, Bz$_o$), 7.89 in (4, Bz$_o$), 7.81 brd (2, J$_{H,H}$ 7.2, Bz$_o$), 7.53-7.16 in (25 ArH), 7.00 m (2, ArH), 5.87 brt (1, J$_{3,4}$ 9.7, H-3$^{II}$), 5.66 brt (1, J$_{4,5}$ 10.2, H-4$^{II}$), 5.60 brt (1, J$_{2,3}$ 9.7, H-2$^{II}$), 4.86 d (1, J$_{H,H}$ 10.8, BnCH$_2$), 4.78 d (1, J$_{1,2}$ 3.5, H-1$^I$), 4.76 d (1, J$_{1,2}$ 7.9, H-1$^{II}$), 4.63 m (4, BnCH$_2$, H-6$^{II}$), 4.51 dd (1, J$_{5,6'}$ 5.0, J$_{66'}$ 12.0, H-6$^{III}$), 4.42 d (1, J$_{H,H}$ 11.3, BnCH$_2$), 4.25 d (1, J$_{H,H}$ 11.3, BnCH$_2$), 4.17 brd (1, H-6$^I$), 4.06 m (1, H-5$^{II}$), 3.88 br (1, J$_{2,3}$ 9.4, J$_{3,4}$ 9.0, H-3$^I$), 3.79 m (2, H-5$^I$, H6$^I$), 3.57 m (5, CH$_2$O, CHO, OCH$_2$), 3.44 m (6, CH$_2$O, OCH$_2$, H-4$^I$, H-2$^I$), 1.61-1.48 m (6, CH, CH$_2$), 1.38-1.01 m (42, CH, CH$_2$), 0.88-0.81 m (30, CH$_3$); $^{13}$C NMR CDCl$_3$ 166.1, 165.8, 165.1, 164.9 (4×C=O Bz), 138.9, 138.5, 138.4 (3×Bn$_{ip}$), 133.4, 133.2, 133.1, 133.0 (4×Bz$_p$), 129.8-127.2 (ArC), 101.3 (C-1$^{II}$), 97.1 (C-1$^I$), 81.7 (C-3$^I$), 79.9 (C-2$^I$), 77.8 (CHO), 77.2 (C-4$^I$), 75.3, 74.4 (2×BnCH$_2$), 72.9 (C-3$^{II}$), 72.7 (BnCH$_2$), 72.2 (C-5$^{II}$), 71.8 (C-2$^{II}$), 70.7 (CH$_2$O), 70.0 (OCH$_2$), 69.8 (C-4$^{II}$), 69.3 (C-5$^I$), 69.0 (OCH$_2$), 68.1 (C-6$^I$), 67.7 (CH$_2$O), 63.3 (C-6$^{II}$), 39.4, 37.6, 37.45, 37.42, 37.3, 37.2, 36.7 (CH$_2$), 32.8, 30.0, 29.8, 28.0 (CH), 24.8, 24.5, 24.4 (CH$_2$), 22.7, 22.6, 19.73, 19.71, 19.67 (CH$_3$); MALDI MS (M+Na)$^+$ 1686.0.

2R)-2,3-Bis[(3R,7R,11R)-3,7,11,15-tetramethyl-hexadecyloxy]propan-1-yl 6-O-β-D-glucopyranosyl-α-D-glucopyranoside (Gentα

Disaccharide (4, 17 mg; 0.010 mmol) was first treated using modified procedure B to yield (2R)-2,3-Bis[(3R,7R,11R)-3,7,11,15-tetramethylhexadecyloxy]propan-1-yl 6-O-β-D-glucopyranosyl-2,3,4-tri-O-benzyl-α-D-glucopyranoside (5) partial $^1$H NMR CDCl$_3$ 4.70 d (1, J$_{1,2}$ 3.5, H-1$^I$) and 4.28 d (1, J$_{1,2}$ 7.6, H-1$^{II}$) which was then treated with procedure C to yield Gentα (8 mg; 82%).

Procedure D-1

(2R)-2,3-Bis[(3R,7R,11R)-3,7,11,15-tetramethyl-hexadecyloxy]propan-1-yl 6-O-[2,3,4,6-tetra-O-acetyl-α-D-glucopyranosyl]-2,3,4-tri-O-acetyl-β-D-glucopyranoside (iMalt-A)

Archaeol (85 mg; 0.13 mmol) and phenyl 6-O-[2,3,4,6-tetra-O-acetyl-α-D-glucopyranosyl]-2,3,4-tri-O-acetyl-β-D-gluco-1-thiopyranoside (153 mg, 1.5 eq.) (1, 31) were dissolved in CH$_2$Cl$_2$ (3.0 mL) and cooled in an ice bath under an argon atmosphere along with powdered 4 Å molecular sieves (200 mg). To this mixture was added N-iodosucinimide (74 mg, 2.5 eq.) followed by silver trifluoromethanesulfonate (33 mg, 1.0 eq.) and the stirring continued for 0.5 h. The reaction was quenched with diisopropylethylamine (excess) and the mixture filtered and rinsed with CH$_2$Cl$_2$. The organic layers were concentrated and the residue purified by silica gel chromatography eluting with hexanes:ethyl acetate:CH$_2$Cl$_2$ 6:3:1 to yield the peracetylated disaccharide β-linked to archaeol, iMalt-A, (19 mg, 15%).

Procedure D-2

Archaeol (51 mg; 0.078 mmol) and (SPh donor, 79 mg, 1.5 eq.) were dissolved in CH$_2$Cl$_2$ (1.5 mL) and cooled in an ice bath under an argon atmosphere. To this solution was added N-iodosucinimide (74 mg, 2.5 eq.) followed by a 0.25 M solution of BF$_3$ etherate and trifluoroethanol (20) (128 µL, 0.5 eq.; made from trifluoroethanol (386 µL) in CH$_2$Cl$_2$ (5.0 mL) which was cooled in a dry ice acetonitrile bath to which was added BF$_3$ etherate (316 µL) followed by treatment under vacuum about 5 torr for 20 minutes) and the stirring continued for 1 h. The reaction was quenched with aqueous NaHCO$_3$ followed by aqueous Na$_2$S$_2$O$_3$ and the mixture filtered and rinsed with CH$_2$Cl$_2$. The organic layers were concentrated and the residue purified by silica gel chromatography eluting with hexanes:ethyl acetate:CH$_2$Cl$_2$ 6.5:2.5:1 to yield iMalt (41 mg, 42%).

(2R)-2,3-Bis[(3R,7R,11R)-3,7,11,15-tetramethyl-hexadecyloxy]propan-1-yl 4-O-[2,3,4,6-tetra-O-acetyl-α-D-glucopyranosyl]-2,3,4-tri-O-acetyl-β-D-glucopyranoside (Malt-A)

Malt-A was prepared using either procedure D-1 or D-2

(2R)-2,3-Bis[(3R,7R,11R)-3,7,11,15-tetramethyl-hexadecyloxy]propan-1-yl 4-O-[2,3,4,6-tetra-O-acetyl-β-D-glucopyranosyl]-2,3,4-tri-O-acetyl-β-D-glucopyranoside (Cello-A)

Cello-A was prepared using either procedure D-1 or D-2

(2R)-2,3-Bis[(3R,7R,11R)-3,7,11,15-tetramethyl-hexadecyloxy]propan-1-yl 4-O-[2,3,4,6-tetra-O-acetyl-β-D-galactopyranosyl]-2,3,4-tri-O-acetyl-β-D-glucopyranoside (Lac-A)

Cello-A was prepared using either procedure D-1 or D-2

(2R)-2,3-Bis[(3R,7R,11R)-3,7,11,15-tetramethyl-hexadecyloxy]propan-1-yl 6-O-[2,3,4,6-tetra-O-acetyl-α-D-galactopyranosyl]-2,3,4-tri-O-acetyl-β-D-glucopyranoside (Melo-A)

Melo-A was prepared using either procedure D-1 or D-2

2R)-2,3-Bis[(3R,7R,11R)-3,7,11,15-tetramethyl-hexadecyloxy]propan-1-yl 6-O [-α-D-glucopyranosyl]-β-D-glucopyranoside (iMalt-B iMalt-B was prepared from iMalt-A using modified Procedure B.

2R)-2,3-Bis[(3R,7R,11R)-3,7,11,15-tetramethyl-hexadecyloxy]propan-1-yl 4-O-α-D-glucopyranosyl-β-D-glucopyranoside (Malt-A Malt-B was prepared using from Malt-A using modified Procedure B.

2R)-2,3-Bis[(3R,7R,11R)-3,7,11,15-tetramethyl-hexadecyloxy]propan-1-yl 4-O-[2,3,4,6-tetra-O-acetyl]-β-D-glucopyranosyl-β-D-glucopyranoside (Cello-A Cello-B was prepared from Cello-A using modified procedure B.

2R)-2,3-Bis[(3R,7R,11R)-3,7,11,15-tetramethyl-hexadecyloxy]propan-1-yl 4-O-β-D-galactopyranosyl-β-D-glucopyranoside (Lac-B Lac-B was prepared from Lac-A using modified Procedure B.

2R)-2,3-Bis[(3R,7R,11R)-3,7,11,15-tetramethyl-hexadecyloxy]propan-1-yl 6-O-α-D-galactopyranosyl-β-D-glucopyranoside (Melo-B Melo-B was prepared from Melo-A using modified Procedure B.

cald 6-O-β-D-glucopyranosyl-β-D-glucopyranoside (Gent2cald-A)

This was made using Glc$_2$ donor and caldarchaeol using procedure D-2 with double the amount of all reagents except the lipid to account for the extra hydroxyl.

cald 6-O-β-D-glucopyranosyl-β-D-glucopyranoside (Gent2cald-A)

Gent2cald-B was prepared from Gent2cald-A using modified Procedure B.

Synthetic Anionic Archaeal Lipid Synthesis

Archaeol was obtained as before from *Halobacterium* polar lipids and combined with a phospho-L-serine head group protected as its benzyl ester and carbobenzoxy carbamate, according to the procedure in (33) to form archaetidylserine (AS).

NMR and MS Tables $^1$H and $^{13}$C NMR of 1-5, Man$_{1-5}$-A, Man$_{1-5}$-B, Glc$_1$', Glc$_2$-A, Glc$_3$-A, Glc$_3$M-A, iMalt-A, Malt-A, Lac-A, Melo-A, Cello-A and Gent2Cald-A were obtained in CDCl$_3$ solution (referenced to residual CHCl$_3$ at 7.26 ppm $^1$H and 77.0 ppm central resonance $^{13}$C) whereas those of Man$_{1-5}$-C, Glc$_2$-B, Glc$_3$-B, Glc$_3$M-B, iMalt-B, Malt-B, Lac-B, Melo-B, Cello-B and Gentα were obtained in 1:1 (v:v) solutions of CD$_3$OD:CDCl$_3$ (referenced to residual CHD$_2$OD at 3.31 ppm $^1$H and 49.15 ppm central resonance $^{13}$C). Gent2Cald-B spectra were obtained in 1:4 (v:v) solutions of CD$_3$OD:CDCl$_3$ with the same reference as 1:1. Chemical shifts are in ppm and coupling constants in Hz. NMR was performed on either a Varian 400 MHz or 200 MHz spectrometers. The NMR data are compiled in Tables 1-8. Table 9 contains the MALDI MS data.

Source of Other Lipids

The following lipids were purified in biologically pure form by thin-layer chromatography of total polar lipid extracts. Sulfonoquinovosyl diacylglycerol was from *Marinococcus halophilus* (22), archaetidylinositol and archaetidylglycerol from *Methanosarcina mazei*, and archaetidylglycerophosphate-methyl (AGP-CH$_3$) from *Halobacterium salinarum*.

Archaeosome/Liposome Formulation

Archaeosomes/liposomes were prepared by hydrating 20-30 mg lipids at 40° C. in 2 ml of PBS buffer (10 mM sodium phosphate, 160 mM NaCl, pH 7.1) or water with (Ag-loaded) or without (Ag-free) the test antigen OVA dissolved at 10 mg/ml. In some cases, cholesterol (Sigma), DPPS, DPPE, or DPPG (Avanti Polar Lipids) polar lipids were mixed in chloroform/methanol with the synthetic glycoarchaeols. These were dried to remove all traces of solvent and hydrated in PBS or water, as above. The size of the vesicles in the preparations was decreased by sonication in a sonic water bath (Fisher Scientific) at 40° C. Antigen not entrapped was removed by centrifugation and washing. Quantification of antigen loading was done by SDS polyacrylamide gel electrophoresis as described and based on salt corrected dry weights (27). Average diameters were determined by particle size analysis using a 5 mW He/Ne laser (Nicomp 370).

Mice

To determine adjuvant activity, various synthetic archaeosomes with OVA entrapped (OVA-archaeosomes) were used to immunize female C57BL/6 mice on days 0 and 21 (6-8 weeks old on first injection). Injections were subcutaneous at the tail base with 0.1 ml PBS containing 15 μg OVA entrapped in 0.2-0.63 mg lipids. Blood samples were collected from the tail vein for anti-OVA IgG/IgM antibody titration done by ELISA (13). In some cases faecal extracts were assayed for IgA (and IgG) to assess mucosal responses following systemic immunizations. Fresh faeces (about 30 mg dry weight) were collected from 4 mice/group, and extracted by adding 0.5 ml of phosphate buffered saline (pH 7.0) containing 10% fetal calf serum and 0.1% sodium azide. Homogenized samples were centrifuged and Elisa measured anti OVA antibody in supernatants. Spleens were collected to determine CTL activity using the Cr$^{51}$-assay with specific and non-specific targets EG.7 and EL-4, respectively (14). In Elispot assays antigen-specific CD8$^+$ T cell activity was measured in splenic cells from immunized mice by determining the number of SIINFEKL stimulated IFN-γ-secreting cells per 5×10$^5$ splenic cells (15).

A skin melanoma solid tumor model was used in mice to evaluate protection achieved upon vaccination with synthetic archaeosomes. Mice were vaccinated subcutaneously with 15 μg OVA or synthetic archaeosome compositions containing 15 μg OVA at 0 and 3 weeks. Archaeosome lipid compositions were synthetic archaeal lipid/DPPG/cholesterol (25/55/20 mol %). At week 7 post first injection 5×106 B16OVA cells were injected subcutaneously in the shaved lower dorsal area. The time was recorded when solid tumours became evident.

TABLE 1

$^1$H NMR data of Man$_{1-5}$-archacol compounds - Sugar and protecting groups (n.d. not determined).

| Compound residue | H-1 (J$_{1,2}$) | H-2 (J$_{2,3}$) | H-3 J$_{(3,4)}$ | H-4 (J$_{4,5}$) | H-5 J$_{(5,6)}$ | H-6 (J$_{5,6}$) | H-6' (J$_{6,6'}$) | BnAr | BnCH$_2$ J$_{(H,H)}$ | AcCH$_3$ | OH (J$_{2,OH}$) |
|---|---|---|---|---|---|---|---|---|---|---|---|
| Man$_1$-A | 4.82 brs | 5.36 (2.9) | 3.93 (9.2) | 3.87 (9.4) | 3.79 brt | 3.78 brd | 3.78 brd | 7.3-7.1 m (15) | 4.82 (12.0) 4.66 (12.0) 4.65 brs (2) 4.48 (12.0) 4.45 (12.0) | 2.11 | |
| Man$_1$-B | 4.92 (1.2) | 4.06 bs | 3.87 m | 3.87 m | 3.80 brt | 3.77 brd | 3.69 brd (11.2) | 7.3-7.1 m (15) | 4.82 (12.0) 4.68 abq (2) 4.66 (12.0) 4.52 d (2) (12.0) | | 2.4 brs |
| Man$_1$-C | 4.76 brs | 3.83 brs | 3.70 m | 3.68 m | 3.51 m | 3.76 brd | 3.76 brd | — | — | — | |
| Man$_2$-A Man I | 4.86 brs | 3.99 brs | 3.89 m | 3.85 m | 3.90 m | 3.7-3.8 m | 3.7-3.8 m | 7.3-7.1 m (30) | 4.83 d 4.80 d 4.64 m (5) 4.54 (11.2) 4.46 (3) 4.35 (10.8) | 2.09 | |
| Man II | 5.08 brs | 5.53 brs | 3.96 m | 3.85 m | 3.79 m | 3.7-3.8 m | 3.7-3.8 m | | | | |
| Man$_2$-B Man I | 4.92 brs | 3.99 brs | 3.87 m | 3.79 m | 3.88 m | 3.7-3.8 m | 3.7-3.8 m | 7.3-7.1 m (30) | 4.78 (10.4) 4.75 (11.2) 4.61 m (4) 4.47 m (6) | | — |
| Man II | 5.10 brs | 4.07 brs | 3.81 m | 3.79 m | 3.72 m | 3.7-3.8 m | 3.7-3.8 m | | | | |
| Man$_2$-C Man I | 4.99 brs | 3.81 brs | 3.70 m | 3.67 m | 3.48 m | 3.76 m | 3.76 m | | | | |
| Man II | 4.91 brs | 3.92 brs | 3.69 m | 3.66 m | 3.58 m | 3.78 m | 3.75 m | | | | |
| Man$_3$-A Man I | 4.89 brs | 3.98 brs | 3.83 m | 3.83 m | 3.79 m | 3.8-3.7 m | 3.8-3.7 m | 7.3-7.1 m (45) | 4.81 (2) 4.7-4.38 (15) 4.28 (12.0) | 2.10 s (3) | |
| Man II | 5.18 brs | 4.08 brs | 3.80 m | 3.83 m | 3.79 m | 3.8-3.7 m | 3.8-3.7 m | | | | |
| Man III | 5.03 brs | 5.52 brs | 3.96 m | 3.70 m | 3.83 m | 3.8-3.7 m | 3.8-3.7 m | | | | |
| Man$_3$-B Man I | 4.89 brs | 3.97 m | 3.75 m | 3.67 m | 3.74 m | 3.7 m | 3.64 m | 7.3-7.1 m (45) | 4.78 m (3) 4.65 m (2) 4.59-4.42 m (12) 4.30 (12.2) | | 2.35 brs |
| Man II | 5.19 brs | 4.09 m | 3.81 m | 3.82 | 3.8 m | 3.7 m | 3.64 m | | | | |
| Man III | 5.10 brs | 4.09 m | 3.81 m | 3.82 | 3.8 m | 3.7 m | 3.64 m | | | | |
| Man$_3$-C Man I | 4.94 brs | 3.78 m | 3.60 m | 3.60 m | 3.44 m | 3.8-3.6 m | 3.8-3.6 m | | | | |
| Man II | 4.96 brs | 3.99 brs | 3.63 m | 3.63 m | 3.48 m | 3.8-3.6 m | 3.8-3.6 m | | | | |
| Man III | 5.22 brs | 3.93 brs | 3.73 m | 3.58 m | 3.53 m | 3.8-3.6 m | 3.8-3.6 m | | | | |
| Man$_4$-A Man I | 4.86 brs | 4.00 m | 3.82 m | 3.66 m | 3.67 m | 3.7-3.4 m | 3.7-3.4 m | 7.3-7.1 m | 4.83-4.30 m, 4.16 d (12.0) | 2.12 s (3) | |
| Man II | 5.19 brs | 4.10 m | 3.77 m | 3.75 m | 3.76 m | 3.7-3.4 m | 3.7-3.4 m | | | | |
| Man III | 5.22 brs | 4.10 m | 3.77 m | 3.75 m | 3.76 m | 3.7-3.4 m | 3.7-3.4 m | | | | |
| Man IV | 5.04 brs | 5.55 brdd | 3.75 m | 3.75 m | 3.76 m | 3.7-3.4 m | 3.7-3.4 m | | | | |
| Man$_4$-B Man I | 4.92 brs | 3.98 m | 3.92-3.78 m | 3.74 m | 3.90-3.75 m | 3.74-3.48 m | 3.74-3.48 m | 7.3-7.1 m (60) | 4.82-4.26 m (23) 4.13 d (12.4) | | 2.3 br |
| Man II | 5.20 m | 4.11 m | 3.92-3.78 m | 3.90 m | 3.90-3.75 m | 3.74-3.48 m | 3.74-3.48 m | | | | |
| Man III | 5.20 m | 4.11 m | 3.92-3.78 m | 3.90 m | 3.90-3.75 m | 3.74-3.48 m | 3.74-3.48 m | | | | |
| Man IV | 5.11 brs | 4.08 m | 3.92-3.78 m | 3.90 m | 3.90-3.75 m | 3.74-3.48 m | 3.74-3.48 m | | | | |
| Man$_4$-C Man I | 4.97 brs | 3.85 m | 3.80 m | 3.48 m | n.d. | n.d. | n.d. | | | | |
| Man II | 5.24 brs | 3.99 m | 3.80 m | 3.62 m | n.d. | n.d. | n.d. | | | | |
| Man III | 5.27 brs | 3.99 m | 3.80 m | 3.65 m | n.d. | n.d. | n.d. | | | | |
| Man IV | 4.99 brs | 3.95 m | 3.70 m | 3.70 m | n.d. | n.d. | n.d. | | | | |
| Man$_5$-A Man I | 4.93 brs | 3.97 m | n.d. | n.d. | n.d. | n.d. | n.d. | 7.3-7.1 m (75) | 4.84 m (3) 4.77 (11.6) 4.66-4.30 m (23) 4.25 (11.0) 4.17 m (2) | 2.03 | |
| Man II | 5.17 brs | 4.07 m | n.d. | n.d. | n.d. | n.d. | n.d. | | | | |
| Man III | 5.21 brs | 4.07 m | n.d. | n.d. | n.d. | n.d. | n.d. | | | | |
| Man IV | 5.22 brs | 4.07 m | n.d. | n.d. | n.d. | n.d. | n.d. | | | | |

TABLE 1-continued $^1$H NMR data of Man$_{1-5}$-archaeol compounds - Sugar and protecting groups (n.d. not determined).

| Compound residue | H-1 ($J_{1,2}$) | H-2 ($J_{2,3}$) | H-3 $J_{(3,4)}$ | H-4 ($J_{4,5}$) | H-5 $J_{(5,6)}$ | H-6 ($J_{5,6'}$) | H-6' ($J_{6,6'}$) | BnAr | BnCH$_2$ $J_{(H,H)}$ | AcCH$_3$ | OH ($J_{2,OH}$) |
|---|---|---|---|---|---|---|---|---|---|---|---|
| Man V | 5.01 brs | 5.51 brs | n.d. | n.d. | n.d. | n.d. | n.d. | | | | |
| Man$_5$-B Man I | 4.93 brs | 3.91 m | n.d. | n.d. | n.d. | n.d. | n.d. | 7.3 7.0 m (75) | 4.83-4.28 m (28) 4.20 (11.2) 4.08 m (1) | | n.d. |
| Man II | 5.18 brs | 4.08 m | n.d. | n.d. | n.d. | n.d. | n.d. | | | | |
| Man III | 5.21 m | 4.08 m | n.d. | n.d. | n.d. | n.d. | n.d. | | | | |
| Man IV | 5.21 m | 4.08 m | n.d. | n.d. | n.d. | n.d. | n.d. | | | | |
| Man V | 5.10 brs | 4.08 m | n.d. | n.d. | n.d. | n.d. | n.d. | | | | |
| Man$_5$-C Man I | 4.92 brs | 3.80 m | 3.74 m | 3.46 m | n.d. | n.d. | n.d. | | | | |
| Man II | 5.20 brs | 3.94 m | 3.76 m | 3.58 m | n.d. | n.d. | n.d. | | | | |
| Man III | 5.24 brs | 3.94 m | 3.76 m | 3.62 m | n.d. | n.d. | n.d. | | | | |
| Man IV | 5.24 brs | 3.94 m | 3.76 m | 3.49 m | n.d. | n.d. | n.d. | | | | |
| Man V | 4.95 brs | 3.92 m | 3.65 m | 3.52 m | n.d. | n.d. | n.d. | | | | |

TABLE 2

$^{13}$C NMR data of Man$_{1-5}$-archaeol compounds - Sugars and protecting groups

| Compound residue | C1 | C2 | C3 | C4 | C5 | C6 | AcC=O | AcCH$_3$ | Bn$_{ip}$ | BnCH | BnCH$_2$ |
|---|---|---|---|---|---|---|---|---|---|---|---|
| Man$_1$-A | 97.9 | 68.7 | 78.2 | 74.2 | 71.3 | 68.8 | 170.5 | 21.1 | 138.5, 138.2, 137.9 | 128.4-127.5 | 75.1, 73.4, 71.8 |
| 2Man$_1$-B | 99.4 | 68.3 | 80.2 | 74.2 | 71.0 | 68.8 | — | — | 138.4, 138.2, 137.9 | 128.5-127.5 | 75.0, 73.4, 72.0 |
| Man$_1$-C | 101.1 | 67.7 | 72.1 | 72.1 | 73.5 | 62.2 | | | | | |
| Man$_2$-A Man I | 98.7 | 74.9 | 78.2 | 74.5 | 71.8 | 69.2 | 170.1 | 21.1 | 138.56, 138.52, 138.50, 138.4, 138.2, 138.0 | 128.3-127.3 | 75.0 (2), 73.4, 73.2, 72.1, 71.9 |
| Man II | 99.6 | 68.7 | 79.7 | 74.3 | 71.8 | 69.0 | | | | | |
| Man$_2$-B Man I | 98.8 | 74.6 | 79.7 | 74.3 | 71.5 | 69.2 | — | — | 138.6 (2), 138.4, 138.24, 123.2, 138.0 | 128.4-127.3 | 75.0 (2), 73.3, 73.2, 72.3, 72.1 |
| Man II | 101.1 | 68.5 | 80.0 | 74.3 | 71.8 | 69.0 | | | | | |
| Man$_2$-C Man I | 99.5 | 80.1 | 71.9 | 68.2 | 71.6 | 62.6 | — | — | — | — | — |
| Man II | 103.4 | 71.3 | 74.0 | 68.2 | 73.7 | 62.3 | | | | | |
| Man$_3$-A Man I | 98.8 | 74.7 | 79.4 | 71.9 | 74.7 | 69.2 | 170.2 | 21.2 | 138.6 (3), 138.4 (3), 138.3, 138.2, 138.1 | 128.3-127.5 | 75.0, 73.3, 72.1 |
| Man II | 100.6 | 74.7 | 79.5 | 71.9 | 74.7 | 69.2 | | | | | |
| Man III | 99.4 | 68.7 | 78.2 | 71.9 | 74.2 | 69.3 | | | | | |
| Man$_3$-B Man I | 98.8 | 74.6 | 79.9 | 74.2 | 71.9 | 68.9 | — | — | 138.5, 138.3, 138.1, 138.0 | 128.4-127.4 | 75.0, 73.3, 73.2, 72.3, 72.0 |
| Man II | 100.7 | 74.9 | 79.4 | 74.2 | 71.9 | 68.9 | | | | | |
| Man III | 100.9 | 68.3 | 80.1 | 74.2 | 71.5 | 69.1 | | | | | |
| Man$_3$-C Man I | 99.6 | 79.6 | 71.6 | 68.3 | 74.13 | 62.6 | — | — | — | — | — |
| Man II | 101.6 | 79.4 | 71.7 | 68.5 | 74.05 | 62.7 | | | | | |
| Man III | 103.1 | 71.2 | 71.9 | 67.9 | 73.6 | 62.2 | | | | | |
| Man$_4$-A Man I | 98.8 | 75.2 | 78.3 | 71.8 | 74.7 | 69.2 | 170.1 | 21.2 | 138.62 (2), 138.58, 138.55, 138.5 (2), 138.4 (3), 138.3, 138.2, 138.1 | 128.4-127.4 | 75.0, 73.3, 73.2, 71.92, 71.86, 71.8 |
| Man II | 100.7 | 75.4 | 79.3 | 71.8 | 74.7 | 69.35 | | | | | |
| Man III | 101.1 | 75.5 | 79.3 | 71.7 | 74.6 | 69.35 | | | | | |
| Man IV | 99.4 | 68.8 | 79.3 | 72.3 | 74.3 | 69.41 | | | | | |
| Man$_4$-B Man I | 98.8 | 75.5 | 79.2 | 71.7 | 74.8 | 69.2 | — | — | 138.62 (3), 138.56 (2), 138.5 (2), 138.4, 138.35, 138.31, 138.2, 138.1 | 128.4-127.4 | 74.9, 73.3, 73.2, 72.1, 71.8 |

TABLE 2-continued $^{13}$C NMR data of Man$_{1-5}$-archaeol compounds - Sugars and protecting groups

| Compound residue | C1 | C2 | C3 | C4 | C5 | C6 | AcC=O | AcCH$_3$ | Bn$_{ip}$ | BnCH | BnCH$_2$ |
|---|---|---|---|---|---|---|---|---|---|---|---|
| Man II | 100.9 | 75.1 | 79.3 | 71.6 | 74.8 | 68.8 | | | | | |
| Man III | 100.9 | 75.1 | 79.4 | 71.6 | 74.7 | 68.8 | | | | | |
| Man IV | 101.1 | 68.5 | 80.1 | 72.4 | 74.3 | 69.4 | | | | | |
| Man$_4$-C Man I | 99.9 | 80.1 | 71.6 | 69.0 | 74.6 | 62.9 | | | | | |
| Man II | 102.0 | 79.93 | 72.0 | 68.8 | 74.6 | 63.1 | | | | | |
| Man III | 101.9 | 79.87 | 72.0 | 68.6 | 74.5 | 63.0 | | | | | |
| Man IV | 103.7 | 71.2 | 72.2 | 68.2 | 74.1 | 62.6 | | | | | |
| Man$_5$-A Man I | 98.8 | 76.1 | 78.2 | 71.72 | 74.3 | 69.6 | 170.1 | 21.2 | 138.7, 138.5, 138.4, 138.3, 138.2, 138.1 | 128.4-127.2 | 75.2, 74.9, 73.3, 73.23, 73.19 |
| Man II | 101.2 | 75.7 | 79.0 | 71.78 | 74.7 | 69.5 | | | | | |
| Man III | 101.3 | 75.7 | 79.1 | 71.85 | 74.7 | 69.3 | | | | | |
| Man IV | 101.3 | 75.5 | 79.2 | 71.9 | 74.7 | 69.2 | | | | | |
| Man V | 99.4 | 75.0 | 79.3 | 71.9 | 74.3 | 67.3 | | | | | |
| Man$_5$-B Man I | 98.8 | 75.7 | 79.1 | 71.8 | 75.1 | 69.5 | | | 138.7, 138.6, 138.42, 138.36, 138.2, 138.1 | 128.4-127.2 | 75.1, 75.0, 74.3, 73.2, 72.4, 72.1 |
| Man II | 101.3 | 75.7 | 79.1 | 71.8 | 75.1 | 69.5 | | | | | |
| Man II$_1$ | 101.3 | 75.7 | 79.3 | 71.8 | 75.0 | 69.4 | | | | | |
| Man IV | 100.9 | 75.7 | 79.7 | 71.8 | 75.0 | 69.3 | | | | | |
| Man V | 100.9 | 68.8 | 80.1 | 71.8 | 75.0 | 67.3 | | | | | |
| Man$_5$-C Man I | 99.6 | 79.5 | 71.4 | 68.4 | 74.3 | 62.8 | | | | | |
| Man II | 101.6 | 79.6 | 71.5 | 68.4 | 74.3 | 62.8 | | | | | |
| Man III | 101.6 | 79.6 | 71.5 | 68.4 | 74.3 | 62.8 | | | | | |
| Man IV | 101.6 | 79.6 | 71.5 | 68.4 | 74.3 | 62.8 | | | | | |
| Man V | 103.3 | 72.0 | 71.6 | 68.4 | 74.3 | 62.8 | | | | | |

TABLE 3

$^1$H NMR data of glucose compounds - Sugar and protecting groups

| Compound residue | H-1 (J$_{1,2}$) | H-2 (J$_{2,3}$) | H-3 J$_{(3,4)}$ | H-4 (J$_{4,5}$) | H-5 J$_{(5,6)}$ | H-6 (J$_{5,6'}$) | H-6' (J$_{6,6'}$) | Bz$_o$ | Bz$_{m,p}$ | AcCH$_3$ | OH (J$_{4,OH}$) |
|---|---|---|---|---|---|---|---|---|---|---|---|
| Glc$_1$-A' | 4.81 d (7.3) | 5.44 t (9.7) | 5.41 t (9.7) | 3.95 m | 3.60 m | 4.00 brd | 3.89 brd | 7.96 brd (4) | 7.50 m, 7.36 m | | n.d. |
| Glc$_2$-A Glc I | 4.63 d (7.8) | 5.32 dd (10.0) | 5.56 t (9.8) | 5.08 t (9.6) | 3.79 m | 3.97 brd | 3.79 m | 7.95 d2 (7.3) 7.90 d4 (8.1) 7.86 d2 (8.1) | 7.48 m, 7.35 m | 2.15, 1.94, 1.92 | |
| Glc II | 4.88 d (7.8) | 5.43 dd (9.8) | 5.65 t (9.5) | 5.34 t (9.7) | 3.87 ddd (4.9) | 4.37 dd (2.5) | 4.22 dd (12.5) | | | | |
| Glc$_2$-B Glc I | 4.26 d (7.8) | 3.26 m | 3.47 m | 3.47 m | 3.47 m (1.8) | 4.12 dd (4.5) | 3.78 dd (11.4) | | | | |
| Glc II | 4.31 d (7.6) | 3.26 m | 3.36 m | 3.47 m | 3.36 m (2.5) | 3.85 dd (5.3) | 3.68 dd (12.1) | | | | |
| Glc$_3$-A Glc I | 5.03 d (8.0) | 5.42-5.24 m | 5.42-5.24 m | 3.74-3.62 m | 3.57 m | 4.19 m | 3.90-3.74 m | 7.95 d2 (7.4), 7.85 d4 (7.0), 7.84 d2 (6.8), 7.68 d2 (7.4), | 7.6-7.4 m8, 7.3 m8, 7.23 m4 | 2.12, 1.89, 1.85 | 3.2 m |
| Glc II | 4.61 d (7.6) | 5.42-5.24 m | 5.54 brt | 5.04 brt | 3.90-3.74 m | 3.90-3.74 m | 3.90-3.74 m | | | | |
| Glc III | 4.63 d (7.4) | 5.42-5.24 m | 5.63 brt | 5.42-5.24 m | 3.90-3.74 m | 4.33 dd (4.7) | 4.19 m (12.5) | | | | |
| Glc$_3$-B Glc I | 4.27 d (7.8) | 3.26 m | 3.5-3.34 m | 3.5-3.34 m | 3.5-3.34 m | 4.11 brdd | 3.77 m | | | | |
| Glc II | 4.32 d (7.7) | 3.26 m | 3.5-3.34 m | 3.5-3.34 m | 3.5-3.34 m | 4.14 brdd | 3.77 m | | | | |
| Glc III | 4.33 d (7.6) | 3.26 m | 3.5-3.34 m | 3.5-3.34 m | 3.26 m | 3.85 dd (2.0) | 3.69 m (11.9) | | | | |

TABLE 3-continued

1H NMR data of glucose compounds - Sugar and protecting groups

| Compound residue | H-1 (J_{1,2}) | H-2 (J_{2,3}) | H-3 J_{(3,4)} | H-4 (J_{4,5}) | H-5 J_{(5,6)} | H-6 (J_{5,6'}) | H-6' (J_{6,6'}) | Bz_o | Bz_{m,p} | AcCH_3 | OH (J_{4,OH}) |
|---|---|---|---|---|---|---|---|---|---|---|---|
| Glc_3M-A Glc I | 4.57 d (8.0) | 4.81 dd (9.4) | 5.22 t (9.0) | 3.93 m | 3.68 ddd (3.7) | 4.43 brd (4.1) | 4.29 dd (12.1) | | | 2.15, 2.13, 2.07, 2.04, 2.01, 2.00, 1.98, (3) 1.96 | |
| Glc II | 5.25 d (4.1) | 4.72 dd (10.3) | 5.375 t (9.0) | 3.93 m | 3.93 m | 4.43 brd (3.6) | 4.16 dd (12.3) | | | | |
| Glc III | 5.380 d (4.1) | 4.83 dd (9.9) | 5.33 t (9.5) | 5.04 t (9.0) | 3.93 m (3.6) | 4.23 dd | 4.03 brd (12.0) | | | | |
| Glc_3M-B Glc I | 4.27 d (7.8) | 3.30 dd (10.0) | 3.61 t (9.0) | 3.53 t (9.3) | 3.32 ddd (2.1) | 3.84 dd (3.9) | 3.77 dd (12.0) | | | | |
| Glc II | 5.09 d (3.7) | 3.51-3.42 m | 3.85 t (9.2) | 3.51-3.42 m | 3.7-3.58 m | 3.81-3.75 m | 3.7-3.58 m | | | | |
| Glc III | 5.09 d (3.7) | 3.51-3.42 m | 3.73 m | 3.26 t (9.8) | 3.7-3.58 m | 3.81-3.75 m | 3.81-3.75 m | | | | |

TABLE 4

13C NMR Data of Glucose Compounds - Sugars and Protecting Groups

| Compound residue | C1 | C2 | C3 | C4 | C5 | C6 | Ac C=O | AcCH_3 | BzC=O | Bz_p | Bz_{ip,o,m} |
|---|---|---|---|---|---|---|---|---|---|---|---|
| Glc_1-A' | 101.2 | 71.4 | 77.3 | 70.1 | 75.8 | 62.3 | — | — | 167.6, 165.1 | 133.6, 133.2 | 130.0, 129.7, 129.4, 128.8, 128.5, 128.3 |
| Glc_2-A Glc I | 101.1 | 71.6 | 72.9 | 69.4 | 73.5 | 68.3 | 170.7, 169.7, 169.4 | 20.8, 20.6, 20.5 | 165.7 (2), 165.0, 164.9 | 133.4, 133.3, 133.2, 133.1 | 129.8-128.3 |
| Glc II | 101.1 | 71.5 | 73.0 | 68.3 | 72.2 | 61.9 | | | | | |
| Glc_2-B Glc I | 104.4 | 74.3 | 70.6 | 77.1 | 76.1 | 69.4 | | | | | |
| Glc II | 104.2 | 74.3 | 70.9 | 77.1 | 77.0 | 62.4 | | | | | |
| Glc_3 A Glc I | 101.1 | 71.4 | 76.8 | 69.9 | 74.9 | 69.0 | 170.7, 169.6, 169.4 | 20.8, 20.5, 20.4 | 166.8, 166.2, 165.6, 165.15, 165.06, 164.9 | 133.56, 133.5, 133.4, 133.2, 133.1, 133.0 | 129.9-128.3 |
| Glc II | 101.10 | 71.4 | 72.7 | 69.0 | 74.7 | 67.7 | | | | | |
| Glc III | 101.14 | 71.4 | 73.0 | 68.9 | 72.2 | 61.8 | | | | | |
| Glc_3 B Glc I | 103.9 | 73.5 | 75.2 | 69.7 | 76.2 | 69.0 | | | | | |
| Glc II | 103.9 | 73.5 | 75.2 | 69.7 | 76.2 | 68.9 | | | | | |
| Glc III | 103.6 | 73.5 | 75.6 | 69.7 | 76.2 | 61.0 | | | | | |
| Glc_3M-A Glc I | 100.5 | 72.2 | 75.4 | 72.4 | 71.7 | 63.0 | 170.59, 170.56, 170.51, 170.46, 170.3, 170.1, 169.8, 169.7, 169.5, 169.4 | 20.9, 20.8, 20.64, 20.61, 20.5 | | | |
| Glc II | 95.7 | 70.5 | 71.9 | 73.8 | 68.4 | 62.3 | | | | | |
| Glc III | 95.6 | 70.4 | 70.1 | 67.8 | 68.8 | 61.3 | | | | | |
| Glc_3M-B Glc I | 104.2 | 73.9 | 76.9 | 83.4 | 76.0 | 61.6 | | | | | |
| Glc II | 102.6 | 73.6 | 74.4 | 83.2 | 74.2 | 62.5 | | | | | |
| Glc III | 102.5 | 73.1 | 72.8 | 71.0 | 74.6 | 61.6 | | | | | |

TABLE 5

$^1$H NMR data of Dissacharides - Sugar and protecting groups

| Compound residue | H-1 ($J_{1,2}$) | H-2 ($J_{2,3}$) | H-3 $J_{(3,4)}$ | H-4 ($J_{4,5}$) | H-5 $J_{(5,6)}$ | H-6 ($J_{5,6'}$) | H-6' ($J_{6,6'}$) | Ac(CH$_3$) |
|---|---|---|---|---|---|---|---|---|
| Malt-A Glc$^I$ | 4.58 d (8.0) | 4.83 brt (9.5) | 5.26 brt (9.0) | 3.99 brt (9.0) | 3.66 m | 4.46 dd (2.4) | 4.23 m (11.9) | 2.13, 2.09, 2.04 2.01, 2.00, 1.99 (6) |
| Glc$^{II}$ | 5.40 d (4.2) | 4.86 dd (9.3) | 5.35 brt (9.8) | 5.04 brt (9.7) | 3.95 m | 4.23 m (3.0) | 4.03 dd (12.5) | |
| Malt-B Glc$^I$ | 4.26 d (7.9) | 3.28 m (9.7) | 3.61 brt (9.1) | 3.54 brt (8.9) | 3.31 m | 3.83 m | 3.83 m | |
| Glc$^{II}$ | 5.10 d (3.8) | 3.46 dd (9.9) | 3.62 brt (9.6) | 3.26 brt (9.1) | 3.66 m | 3.69 m | 3.82 m | |
| iMalt-A Glc$^I$ | 4.59 d (7.0) | 4.94 dd (9.7) | 5.20 brt (9.3) | 5.07 brt (9.4) | 3.65 m (4.6) | 3.75 dd | 3.65 (10.9) | 2.12, 2.09, 2.05, 2.03, 2.02, 2.00 (6) |
| Glc$^{II}$ | 5.12 d (3.8) | 4.86 dd (10.3) | 5.44 brt (9.6) | 5.05 brt (9.7) | 4.07 m (4.4) | 4.26 dd | 4.07 m (12.6) | |
| iMalt-B Glc$^I$ | 4.30 d (7.9) | 3.24 brt (9.1) | 3.38 brt (9.1) | 3.50 m | 3.41 m (3.5) | 4.03 dd | 3.64 m (10.8) | |
| Glc$^{II}$ | 4.82 d (3.4) | 3.37 dd (10.0) | 3.62 brt (9.9) | 3.32 m | 3.64 m (2.3) | 3.78 dd (5.3) | 3.69 dd (11.4) | |
| Cello-A Glc$^I$ | 4.52 d (8.3) | 4.92 m (9.5) | 5.15 brt (9.3) | 3.76 brt | 3.55 m | 4.48 (4.9) | 4.08 dd (12.0) | 2.11, 2.07, 2.015, 2.011, 2.0 (6), 1.97 |
| Glc$^{II}$ | 4.49 d (8.1) | 4.92 m (9.9) | 5.13 brt (9.5) | 5.05 brt | 3.64 m (3.9) | 4.36 dd | 4.03 brd (12.2) | |
| Cello-B Glc$^I$ | 4.29 d (7.8) | 3.29 dd (8.8) | 3.53 brt (9.1) | 3.57 m | 3.37 m | 3.85 m | 3.85 m | |
| Glc$^{II}$ | 4.39 d (7.9) | 3.26 dd (8.5) | 3.36 brt (9.1) | 3.38 brt (9.4) | 3.34 m | 3.87 brd | 3.67 brd (10.8) | |
| Lac-A Glc$^I$ | 4.54 d (8.0) | 4.90 dd (9.6) | 5.18 brt (9.2) | 3.79 brt (9.6) | 3.54 m | 4.47 brd | 4.09 m | 2.15, 2.11, 2.06, 2.04 (6), 2.03, 1.96 |
| Gal$^{II}$ | 4.47 d (8.0) | 5.10 dd (10.5) | 4.95 dd (3.4) | 5.35 brd | 3.86 m | 4.09 m | 4.09 m | |
| Lac-B Glc$^I$ | 4.29 d (7.8) | 3.29 m | 3.57 m | 3.57 m | 3.38 m | 3.85 m | 3.85 m | |
| Gal$^{II}$ | 4.34 d (7.8) | 3.57 m | 3.48 m (3.5) | 3.83 brd | 3.63 m (7.2) | 3.79 dd (4.4) | 3.70 (11.9) | |
| Melo-A Glc$^I$ | 4.58 d (8.0) | 4.94 brt (8.9) | 5.19 brt (10.0) | 5.12 m | 3.58 m (4.0) | 3.74 dd | 3.58 m (10.8) | 2.132, 2.128, 2.05, 2.04, 2.03, 2.00, 1.98 |
| Gal$^{II}$ | 5.17 d (4.1) | 5.10 dd (10.4) | 5.33 dd (3.2) | 5.45 brt (2.6) | 4.22 m | 4.08 brd | 4.08 brd | |
| Melo-B Glc$^I$ | 4.30 d (7.9) | 3.24 dd (9.1) | 3.38 brt (8.6) | 3.47 m | 3.47 m (2.9) | 4.05 dd | 3.63 m (10.6) | |
| Gal$^{II}$ | 4.87 d (3.0) | 3.73 m | 3.91 m | 3.73 m | 3.85 brt | 3.73 m | 3.73 m | |
| Gentα Glc$^I$ | 4.78 d (3.5) | 3.40 dd (10.0) | 3.63 brt (9.5) | 3.47 brt (9.8) | 3.70 m | 4.08 brd | 3.79 dd (10.3) | |
| Glc$^{II}$ | 4.31 d (7.8) | 3.26 m | 3.38 m | 3.32 m | 3.26 m (2.3) | 3.85 dd (4.9) | 3.69 m (11.8) | |

TABLE 6

$^{13}$C NMR Data of Dissacharides - Sugars and Protecting Groups

| Compound residue | C1 | C2 | C3 | C4 | C5 | C6 | AcC=O | AcCH$_3$ |
|---|---|---|---|---|---|---|---|---|
| Malt-A Glc$^I$ | 100.5 | 72.2 | 75.5 | 72.8 | 72.0 | 62.9 | 170.51, 170.50, 170.4, 170.2, 169.9, 169.5, 169.4 | 20.9, 20.8, 20.7 |
| Glc$^{II}$ | 95.5 | 70.0 | 69.1 | 68.0 | 68.5 | 61.5 | | |
| Malt-B Glc$^I$ | 104.2 | 73.9 | 74.0 | 81.0 | 76.0 | 61.5 | | |
| Glc$^{II}$ | 102.6 | 73.5 | 76.9 | 70.97 | 74.5 | 62.5 | | |
| iMalt-A Glc$^I$ | 100.8 | 71.3 | 72.9 | 69.2 | 72.5 | 66.5 | 170.6, 170.29, 170.27, 170.0, 169.6, 169.4, 169.2 | 20.7, 20.6 |
| Glc$^{II}$ | 96.0 | 70.6 | 69.9 | 68.4 | 67.4 | 61.8 | | |
| iMalt-B Glc$^I$ | 104.7 | 74.4 | 73.2 | 70.4 | 75.6 | 66.4 | | |
| Glc$^{II}$ | 99.3 | 77.2 | 74.9 | 71.2 | 72.8 | 62.3 | | |
| Cello-A Glc$^I$ | 100.86 | 71.57 | 72.58 | 76.5 | 72.54 | 61.9 | 170.4, 170.2, 170.17, 169.7, 169.4, 169.2, 169.0 | 20.8, 20.64, 20.61, 20.5 |
| Glc$^{II}$ | 100.76 | 71.57 | 72.9 | 67.8 | 71.9 | 61.5 | | |
| Cello-B Glc$^I$ | 104.05 | 74.1 | 75.6 | 80.6 | 70.6 | 61.7 | | |
| Glc$^{II}$ | 104.13 | 74.1 | 75.8 | 77.2 | 77.4 | 61.9 | | |
| Lac-A Glc$^I$ | 100.8 | 71.6 | 72.9 | 76.3 | 72.5 | 62.0 | 170.3 (2), 170.1, 170.0, 169.7, 169.4, 169.0 | 20.81, 20.76, 20.65, 20.58, 20.46 |
| Gal$^{II}$ | 101.1 | 69.0 | 71.0 | 66.5 | 70.6 | 60.7 | | |
| Lac-B Glc$^I$ | 104.1 | 74.1 | 75.6 | 80.7 | 75.8 | 61.8 | | |
| Gal$^{II}$ | 104.6 | 76.5 | 74.3 | 69.8 | 72.0 | 62.2 | | |
| Melo-A Glc$^I$ | 108.8 | 71.3 | 73.0 | 68.9 | 72.6 | 66.2 | 170.6, 170.4, 170.3, 170.2, 169.8, 169.3, 169.2 | 20.8, 20.71, 20.66, 20.6 |

TABLE 6-continued $^{13}$C NMR Data of Dissacharides - Sugars and Protecting Groups

| Compound residue | C1 | C2 | C3 | C4 | C5 | C6 | AcC=O | AcCH$_3$ |
|---|---|---|---|---|---|---|---|---|
| Gal$^{II}$ | 96.6 | 67.97 | 67.4 | 68.04 | 66.4 | 61.7 | | |
| Melo-B Glc$^{I}$ | 104.7 | 74.5 | 77.3 | 70.5 | 75.7 | 66.4 | | |
| Gal$^{II}$ | 99.6 | 70.1 | 70.5 | 71.3 | 71.6 | 62.4 | | |
| Gentα Glc$^{I}$ | 99.8 | 73.0 | 74.5 | 70.7 | 71.9 | 69.0 | | |
| Glc$^{II}$ | 103.9 | 74.3 | 77.3 | 70.9 | 77.0 | 62.4 | | |

TABLE 7

$^1$H NMR data of the core lipid (archaeol) in synthetic archaeol-compounds (Glyc1-3 is H on glycerol carbons sn-1-3; Phy1-2 is H on C1 C1', C2 or C2'; CH, CH$_2$, CH$_3$ represent combined H signals from these groups of isopranoid chains).

| Compound | Glyc1 | Glyc2 | Glyc3 | Phy 1 | Phy 1' | Phy 2, 2' | CH | CH$_2$ | CH$_3$ |
|---|---|---|---|---|---|---|---|---|---|
| Man$_1$-A | 3.67 m, 3.50 m | 3.53 m | 3.55 m | 3.55 m | 3.42 m | 1.52 m, 1.31 m | 1.47 m 1.30 m | 1.4-1.0 | 0.8 m |
| Man$_1$-B | 3.74 m, 3.53 m | 3.53 m | 3.57 m | 3.55 m | 3.45 m | 1.52 m, 1.35 m | 1.54 m, 1.36 m | 1.4-1.0 | 0.85 m |
| Man$_1$-C | 3.68 m, 3.47 m | 3.54 m | 3.56 m | 3.45 m | 3.44 m | 1.50 m, 1.32 m | 1.56 m, 1.33 m | 1.4-1.0 | 0.8 m |
| Man$_2$-A | 3.62 m, 3.37 m | 3.47 m | 3.50 m | 3.40 m | 3.38 m | 1.54 m, 1.29 m | 1.48 m, 1.44 m 1.31 m | 1.4-1.0 | 0.8 m |
| Man$_2$-B | 3.65 m, 3.40 m | 3.51 m | 3.54 m | 3.44 m | 3.40 m | 1.57 m, 1.32 m | 1.52 m, 1.50 m, 1.26 m | 1.4-1.0 | 0.85 m |
| Man$_2$-C | 3.69 m, 3.43 m | 3.55 m | 3.57 m | 3.46 m | 3.46 m | 1.55 m, 1.33 m | 1.49 m, 1.47 m, 1.33 m | 1.4-1.0 | 0.81 m |
| Man$_3$-A | 3.63 m, 3.33 m | 3.48 m | 3.50 m | 3.40 m | 3.36 m | 1.56 m, 1.31 m | 1.52 m, 1.48 m, 1.36 m | 1.4-1.0 | 0.85 m |
| Man$_3$-B | 3.64 m, 3.35 m | 3.53 m | 3.52 m | 3.43 m | 3.39 m | 1.53 m, 1.30 m | 1.51 m. 1.46 m, 1.33 m | 1.4-1.0 | 0.81 m |
| Man$_3$-C | 3.65 m, 3.38 m | 3.51 m | 3.53 m | 3.41 m | 3.40 m | 1.51 m, 1.29 m | 1.44 m, 1.42 m, 1.30 m | 1.4-1.0 | 0.79 m |
| Man$_4$-A | 3.60 m, 3.40 m | 3.50 m | 3.51 m | 3.40 m | 3.38 m | 1.55 m, 1.30 m | 1.50 m, 1.45 m, 1.33 m | 1.4-1.0 | 0.85 m |
| Man$_4$-B | 3.60 m, 3.40 m | 3.50 m | 3.51 m | 3.40 m | 3.38 m | 1.55 m, 1.30 m | 1.50 m, 1.45 m, 1.33 m | 1.4-1.0 | 0.85 m |
| Man$_4$-C | 3.68 m, 3.42 m | 3.56 m | 3.54 m | 3.46 m | 3.45 m | 1.57 m, 1.34 m | 1.50 m 1.49 m 1.35 m | 1.4-1.0 | 0.84 m |
| Man$_5$-A | 3.59 m, 3.45 m | 3.54 m | 3.57 m, 3.50 m | 3.50 m | 3.49 m | 1.60 m, 1.40 m | 1.50 m, 1.40 m | 1.4-1.0 | 0.85 m |
| Man$_5$-B | 3.59 m, 3.38 m | 3.46 m | 3.71 m | 3.38 m | 3.34 m | 1.54 m, 1.39 m | 1.50 m, 1.40 m | 1.4-1.0 | 0.9 m |
| Man$_5$-C | 3.48 brm | 3.57 m | 3.58 m | 3.47 m | 3.43 m | 1.54 m, 1.39 m | 1.53 m | 1.4-1.0 | 0.9 m |
| Glc$_1$-A' | 3.95 m, 3.60 m | 3.49 m | 3.40 m | 3.37 m | 3.35 m | 1.51 m, 1.25 m | 1.50 m, 1.34 m | 1.4-1.0 | 0.85 m, 0.75 d (6.4) |
| Glc$_2$-A | 3.79 m, 3.37 m | 3.37 m | 3.37 m | 3.28 m | 3.26 m | 1.48 m, 1.23 m | 1.50 m, 1.33 m | 1.4-1.0 | 0.85 m, 0.74 d (6.4) |
| Glc$_2$-B | 3.90 dd (3.7), (10.3) 3.56 m | 3.61 m | 3.58 m | 3.50 m | 3.44 m | 1.47 m, 1.31 m | 1.54 m, 1.2 m | 1.4-1.0 | 0.85 m |
| Glc$_3$-A | 3.74 m 3.66 m | 3.37 m | 3.34 m | 3.2 m | 3.2 m | 1.48 m, 1.32 m | 1.50 m, 1.36 m | 1.4-1.0 | 0.85 m, 0.71 d (6.8) |
| Glc$_3$-B | 3.72 m, 3.45 m | 3.49 m | 3.50 m | 3.39 m | 3.32 m | 1.42 m, 1.22 m | 1.34 m, 1.20 m | 1.4-1.0 | 0.8 m |
| Glc$_3$M-A | 3.86 m 3.54 m | 3.54 m | 3.54 m | 3.42 m | 3.40 m | 1.56 m, 1.32 m | 1.48 m, 1.34 m | 1.4-1.0 | 0.8 m |
| Glc$_3$M-B | 3.92 brdd (10.0), (2.7) 3.59 m | 3.63 m | 3.62 m | 3.53 m | 3.48 m | 1.59 m, 1.35 m | 1.52 m, 1.36 m | 1.4-1.0 | 0.85 m |
| Malt-A | 3.89 m, 3.53 m | 3.53 m | 3.42 m | 3.53 m | 3.42 m | 1.60 m, 1.37 m | 1.55 m, 1.40 m | 1.41-1.01 | 0.85 m |
| Malt-B | 3.92 m, 3.61 m | 3.61 m | 3.51 m | 3.61 m | 3.48 m | 1.61 m, 1.31 m | 1.55 m, 1.38 m | 1.40-1.01 | 0.85 m |

TABLE 7-continued $^1$H NMR data of the core lipid (archaeol) in synthetic archaeol-compounds (Glyc1-3 is H on glycerol carbons sn-1-3; Phy1-2 is H on C1 C1', C2 or C2'; CH, CH$_2$, CH$_3$ represent combined H signals from these groups of isopranoid chains).

| Compound | Glyc1 | Glyc2 | Glyc3 | Phy 1 | Phy 1' | Phy 2, 2' | CH | CH$_2$ | CH$_3$ |
|---|---|---|---|---|---|---|---|---|---|
| iMalt-A | 3.85 m, 3.56 m | 3.56 m | 3.43 m | 3.56 m | 3.43 m | 1.56 m, 1.40 m | 1.52 m, 1.28 m | 1.37-1.03 | 0.85 m |
| iMalt-B | 3.92 m, 3.58 m | 3.63 m | 3.52 m, 3.44 m | 3.60 m | 3.44 m | 1.51 m, 1.38 m | 1.58 m, 1.32 m | 1.40-1.01 | 0.86 m |
| Cello-A | 3.87 m, 3.55 m | 3.55 m | 3.40 m | 3.55 m | 3.40 m | 1.58 m, 1.37 m | 1.61 m, 1.31 m | 1.40-1.06 | 0.78 m |
| Cello-B | 3.88 m, 3.60 m | 3.60 m | 3.55 m, 3.49 m | 3.60 m | 3.49 m | 1.56 m, 1.38 m | 1.59 m, 1.31 m | 1.37-1.01 | 0.82 m |
| Lac-A | 3.86 m, 3.54 m | 3.54 m | 3.54 m | 3.54 m | 3.41 m | 1.52 m, 1.30 m | 1.60 m, 1.30 m | 1.39-1.03 | 0.85 m |
| Lac-B | 3.92 m, 3.63 m | 3.63 m | 3.63 m, 3.57 m | 3.63 m | 3.57 m | 1.57 m, 1.38 m | 1.59 m, 1.31 m | 1.40-1.02 | 0.85 m |
| Melo-A | 3.86 m, 3.58 m | 3.58 m | 3.43 m | 3.58 m | 3.43 m | 1.55 m, 1.32 m | 1.60 m, 1.30 m | 1.37-1.01 | 0.86 m |
| Melo-B | 3.91 m, 3.63 m | 3.63 m | 3.55 brd (10.3), 3.47 m | 3.63 m | 3.47 m | 1.52 m, 1.33 m | 1.55 m, 1.30 m | 1.40-1.02 | 0.85 m |
| Gentα | 3.73 m, 3.46 m | 3.63 m | 3.52 m | 3.62 m | 3.52 m | 1.58 m, 1.32 m | 1.58 m, 1.31 m | 1.40-1.00 | 0.84 m |

TABLE 8

$^{13}$C NMR Data of Lipids in Archaeol Compounds

| Compound | Glyc1 | Glyc2 | Glyc3 | Phy 1 | Phy 1' | CH | CH$_2$ | CH$_3$ |
|---|---|---|---|---|---|---|---|---|
| Man$_1$-A | 67.4 | 77.4 | 69.0 | 70.5 | 70.1 | 32.8, 29.9, 29.8, 28.0 | 39.4, 37.54, 37.47, 37.4, 37.3, 37.0, 36.7, 24.8, 24.5, 24.4 | 22.7, 22.6, 19.74, 19.70, 19.6 |
| Man$_1$-B | 67.1 | 77.5 | 68.9 | 70.6 | 70.1 | 32.8, 29.9, 29.8, 28.0 | 39.4, 37.53, 37.46, 37.4, 37.3, 37.0, 36.7, 24.8, 24.5, 24.4 | 22.7, 22.6, 19.74, 19.70, 19.6 |
| Man$_1$-C | 67.5 | 78.5 | 69.6 | 71.3 | 70.7 | 33.5, 30.6, 30.4, 30.3 | 40.1, 38.1, 38.0, 37.7, 37.3, 25.5, 25.13, 25.08 | 23.1, 23.0, 20.2 |
| Man$_2$-A | 67.2 | 77.5 | 68.9 | 70.8 | 70.1 | 32.8, 29.9, 29.8, 28.0 | 39.4, 37.53, 37.46, 37.4, 37.3, 37.0, 36.7, 24.8, 24.5, 24.4 | 22.7, 22.6, 19.75, 19.71, 19.6 |
| Man$_2$-B | 67.2 | 77.5 | 69.0 | 70.8 | 70.1 | 32.8, 29.9, 29.8, 28.0 | 39.3, 37.5, 37.4, 37.3, 37.0, 36.6, 24.8, 24.5, 24.4 | 22.7, 22.6, 19.7, 19.6 |
| Man$_2$-C | 67.9 | 77.5 | 69.7 | 71.6 | 70.8 | 33.5, 30.6, 30.5, 28.7 | 40.1, 38.1, 38.0 37.7, 37.4, 25.5, 25.2, 25.1 | 23.14, 23.06, 20.2 |
| Man$_3$-A | 67.2 | 77.4 | 69.0 | 70.9 | 70.0 | 32.8, 30.0, 29.8, 28.0 | 39.4, 37.5, 37.3, 37.1, 36.7, 24.8, 24.5, 24.4 | 22.7, 22.6, 19.8 |
| Man$_3$-B | 67.1 | 77.6 | 69.3 | 71.2 | 70.3 | 33.1, 30.2, 30.0, 28.2 | 39.6, 37.7, 37.5, 37.3, 36.9, 25.1, 24.7, 24.6 | 23.0, 22.9, 20.0 |
| Man$_3$-C | 67.9 | 77.7 | 68.5 | 71.2 | 69.7 | 33.5, 30.6, 30.4, 28.6 | 40.1, 38.1, 37.9, 37.6, 37.3, 25.5, 25.12, 25.07 | 23.1, 23.0, 20.2, 20.1 |
| Man$_4$-A | 67.3 | 78.3 | 69.2 | 71.0 | 70.1 | 32.8, 30.0, 29.8, 28.0 | 39.4, 375, 37.3, 37.1, 36.7, 24.8, 24.5, 24.4 | 22.7, 22.6, 19.74, 19.68, 19.6 |

TABLE 8-continued $^{13}$C NMR Data of Lipids in Archaeol Compounds

| Compound | Glyc1 | Glyc2 | Glyc3 | Phy 1 | Phy 1' | CH | CH$_2$ | CH$_3$ |
|---|---|---|---|---|---|---|---|---|
| Man$_4$-B | 67.3 | 77.6 | 69.0 | 71.6 | 71.0 | 32.8, 30.0, 29.8, 28.0 | 39.4, 37.5, 37.3, 37.1, 36.7, 24.8, 24.5, 24.4 | 22.7, 22.6, 19.7, 19.6 |
| Man$_4$-C | 68.4 | 78.9 | 69.8 | 71.7 | 70.9 | 33.8, 30.8, 30.7, 28.9 | 40.3, 38.43, 38.36, 38.3, 38.2, 38.0, 37.7, 25.7, 25.3 | 23.2, 23.1, 20.4, 20.3 |
| Man$_5$-A | 68.7 | 77.6 | 70.1 | 71.9 | 71.0 | 32.8, 30.0, 29.8, 29.7 | 39.4, 37.6, 37.5, 37.3, 27.1, 36.7, 24.8, 24.5, 24.4 | 22.7, 22.6, 19.8, 19.7 |
| Man$_5$-B | 68.5 | 77.6 | 69.0 | 71.0 | 70.1 | 32.83, 32.81, 31.9, 30.0, 29.8, 29.7, 29.4 | 39.3, 37.5, 37.3, 37.1, 36.7, 24.8, 24.5, 24.4 | 22.7, 22.6, 19.8, 19.7, 19.6 |
| Man$_5$-C | 68.0 | 78.7 | 69.7 | 71.2 | 70.8 | 33.5, 30.6, 30.5, 30.3, 28.7 | 40.1, 39.6, 38.13, 38.09, 38.0, 37.7, 37.4, 25.5, 25.15, 25.10 | 23.1, 23.0, 20.23, 20.15 |
| Glc$_1$-A' | 70.6 | 77.9 | 69.1 | 70.2 | 70.07 | 32.8, 29.9, 29.7, 28.0 | 39.4, 37.5, 37.42, 37.39, 37.3, 36.9, 36.5, 24.8, 24.5, 24.4, 24.3 | 22.7, 22.6, 19.8, 19.7, 19.5 |
| Glc$_2$-A | 70.3 | 77.7 | 69.1 | 70.5 | 69.9 | 32.8, 29.9, 29.7, 28.0 | 39.4, 37.6, 37.5, 37.4, 37.0, 36.6, 24.8, 24.5, 24.4, 24.3 | 22.7, 22.6, 19.7, 19.6, 19.5 |
| Glc$_2$-B | 70.0 | 77.2 | 69.4 | 71.2 | 70.7 | 33.5, 30.6, 30.5, 28.7 | 40.1, 38.13, 38.09, 38.0, 37.7, 37.3, 25.5, 25.14, 25.08 | 23.1, 23.0, 20.3, 20.23, 20.16 |
| Glc$_3$-A | 70.1 | 77.6 | 69.6 | 70.8 | 69.9 | 32.8, 29.9, 29.7, 28.0 | 39.3, 37.55, 37.45, 37.4, 37.3, 37.0, 36.6, 24.8, 24.5, 24.4 | 22.7, 22.6, 19.7, 19.6, 19.5 |
| Glc$_3$-B | 70.5 | 78.1 | 69.7 | 70.5 | 70.5 | 33.1, 30.3, 30.2, 30.0 | 39.7, 37.7, 37.6, 37.2, 36.9, 25.1, 24.8, 24.4 | 22.9, 22.8, 20.0 |
| Glc$_3$M-A | 70.4 | 77.7 | 69.3 | 70.4 | 70.1 | 32.8, 29.9, 29.8, 27.9 | 39.3, 37.41, 37.37, 37.2, 37.1, 36.5, 24.8, 24.4, 24.3 | 22.7, 22.6, 19.71, 19.67 |
| Glc$_3$M-B | 69.8 | 78.4 | 69.4 | 71.2 | 70.8 | 33.5, 30.6, 30.5, 28.7 | 40.01, 38.13, 38.09, 38.0, 37.7, 37.3, 25.5, 25.15, 25.09 | 23.1, 23.0, 20.3, 20.2 |
| Malt-A | 70.47 | 77.8 | 70.51 | 70.1 | 69.3 | 32.8, 29.9, 29.8, 27.9 | 39.3, 37.44, 37.40, 37.36, 37.3, 37.1, 36.6, 24.8, 24.5, 24.3 | 22.7, 22.6, 19.73, 19.69 |
| Malt-B | 69.8 | 78.6 | 71.1 | 71.00 | 69.4 | 33.5, 30.6, 30.5, 28.7 | 40.1, 38.1, 38.0, 37.6, 37.3 | 23.1, 23.0, 20.2 |
| iMalt-A | 70.1 | 78.0 | 70.6 | 70.1 | 69.2 | 32.8, 30.0, 29.0, 28.0 | 39.4, 37.5, 37.4, 37.3, 37.2, 36.6, 24.8, 24.5, 24.4 | 22.7, 22.6, 19.74, 19.70 |
| iMalt-B | 70.2 | 78.6 | 71.0 | 70.7 | 69.4 | 33.5, 30.6, 30.5, 28.7 | 40.1, 38.2, 38.1, 38.0, 37.7, 37.3, 25.5, 25.13, 25.09 | 23.1, 23.0, 20.2 |

TABLE 8-continued

13C NMR Data of Lipids in Archaeol Compounds

| Compound | Glyc1 | Glyc2 | Glyc3 | Phy 1 | Phy 1' | CH | CH₂ | CH₃ |
|---|---|---|---|---|---|---|---|---|
| Cello-A | 70.4 | 77.8 | 70.5 | 70.1 | 69.1 | 32.8, 29.9, 29.8, 27.9 | 39.3, 37.51, 37.45, 37.42, 37.37, 37.3, 37.2, 37.1, 36.6, 24.8, 24.4, 24.3 | 22.7, 22.6, 19.71, 19.66 |
| Cello-B | 69.8 | 78.6 | 71.1 | 70.8 | 69.4 | 33.5, 30.6, 30.5, 28.7 | 40.0, 38.1, 38.0, 37.7, 37.4, 25.5, 25.2 | 23.2, 23.1, 20.2 |
| Lac-A | 70.4 | 77.8 | 70.5 | 70.0 | 69.1 | 32.7, 29.9, 29.8, 27.9 | 39.3, 37.40, 37.36, 37.2, 37.1, 36.5, 24.7, 24.4, 24.3 | 22.7, 22.6, 19.70, 19.65 |
| Lac-B | 70.0 | 77.8 | 71.1 | 70.8 | 69.4 | 33.5, 30.6, 30.5, 28.7 | 40.1, 38.2, 38.1, 38.0, 37.7, 37.4, 25.5, 25.2, 25.1 | 23.15, 23.05, 20.28, 20.24, 20.20 |
| Melo-A | 70.2 | 78.1 | 70.1 | 71.3 | 69.2 | 32.8, 30.0, 29.9, 28.0 | 39.6, 37.5, 37.4, 37.3, 37.2, 36.6, 24.8, 24.5, 24.4 | 19.74, 19.69 |
| Melo-B | 69.5 | 78.8 | 71.1 | 70.8 | 70.3 | 33.6, 30.7, 30.6, 30.4, 28.7 | 40.2, 38.19, 38.17, 38.15, 38.0, 37.8, 37.4, 25.6, 25.22, 25.17 | 23.2, 23.1, 20.30, 20.27, 20.2 |
| Gentα | 71.1 | 78.4 | 68.1 | 70.2 | 69.8 | 33.4, 30.6, 30.4, 30.3, 28.6 | 40.0, 38.08, 38.03, 37.9, 37.6, 37.3, 25.4, 25.1, 25.0 | 23.1, 23.0, 20.2, 20.15, 20.14 |

TABLE 9

M.S. data for archaeol compounds.

| Compound | Formula | M.W. calcd. | MS MALDI | $[\alpha]_D$ | c (solvent) |
|---|---|---|---|---|---|
| Man1-A | $C_{72}H_{118}O_9$ | 1127.23 | 1149.69 (M + Na)⁺<br>1165.65 (M + K)⁺ | +22.0 | 0.3 CHCl₃ |
| Man1-B | $C_{70}H_{116}O_8$ | 1085.70 | 1107.78 (M + Na)⁺<br>1123.71 (M + K)⁺ | +21.0 | 1.1 CHCl₃ |
| Man1-C | $C_{49}H_{98}O_8$ | 814.73 | 837.52 (M + Na)⁺<br>853.38 (M + K)⁺ | +19.5 | 0.8 CHCl₃ |
| Man2-A | $C_{99}H_{146}O_{14}$ | 1559.07 | 1583.17 (M + Na)⁺<br>1599.13 (M + K)⁺ | +18.7 | 0.4 CHCl₃ |
| Man2-B | $C_{97}H_{144}O_{13}$ | 1518.21 | 1540.75 (M + Na)⁺<br>1556.71 (M + K)⁺ | +23.3 | 0.3 CHCl₃ |
| Man2-C | $C_{55}H_{108}O_{13}$ | 976.78 | 999.83 (M + Na)⁺<br>1015.79 (M + K)⁺ | +28.3 | 0.6 CHCl₃ |
| Man3-A | $C_{126}H_{174}O_{19}$ | 1991.27 | 2015.16 (M + Na)⁺<br>2031.12 (M + K)⁺ | +33.5 | 0.2 CHCl₃ |
| Man3-B | $C_{124}H_{172}O_{18}$ | 1949.25 | 1972.89 (M + Na)⁺<br>1988.84 (M + K)⁺ | +29.8 | 0.7 CHCl₃ |
| Man3-C | $C_{61}H_{118}O_{18}$ | 1139.61 | 1161.90 (M + Na)⁺<br>1173.83 (M + K)⁺ | +42.3 | 0.6 CHCl₃ |
| Man4-A | $C_{153}H_{202}O_{24}$ | 2423.46 | 2447.60 (M + Na)⁺<br>2463.59 (M + K)⁺ | +19.1 | 0.9 CHCl₃ |
| Man4-B | $C_{151}H_{200}O_{23}$ | 2383.26 | 2405.74 (M + Na)⁺<br>2421.71 (M + K)⁺ | +20.5 | 1.4 CHCl₃ |
| Man4-C | $C_{67}H_{128}O_{23}$ | 1300.88 | 1324.11 (M + Na)⁺<br>1327.13 (M + K)⁺ | +32.5 | 1.2 CHCl₃ |
| Man5-A | $C_{180}H_{230}O_{29}$ | 2855.65 | 2880.77 (M + Na)⁺<br>2896.70 (M + K)⁺ | +20.5 | 1.2 CHCl₃ |
| Man5-B | $C_{178}H_{228}O_{28}$ | 2813.64 | 2838.57 (M + Na)⁺<br>2854.55 (M + K)⁺ | +39.3 | 2.2 CHCl₃ |

TABLE 9-continued

M.S. data for archaeol compounds.

| Compound | Formula | M.W. calcd. | MS MALD1 | $[\alpha]_D$ c (solvent) |
|---|---|---|---|---|
| Man5-C | $C_{73}H_{138}O_{28}$ | 1462.94 | 1485.99 (M + Na)$^+$<br>1501.86 (M + K)$^+$ | +20.8 0.4 $CH_2Cl_2$:$CH_3OH$ 1:1 v:v |
| Glc$_3$M-A | $C_{109}H_{148}O_{27}$ | 1889.02 | 1912.01 (M + Na)$^+$ | |
| Glc$_3$M-B | $C_{61}H_{118}O_{18}$ | 1139.61 | 1161.7 (M + Na)$^+$ | |
| Gentα | $C_{55}H_{108}O_{13}$ | 976.78 | 999.8 (M + Na)$^+$ | |
| iMalt-A | $C_{69}H_{123}O_{20}$ | 1271.86 | 1294.1 (M + Na)$^+$<br>1310.0 (M + K)$^+$ | |
| Malt-A | $C_{69}H_{123}O_{20}$ | 1271.86 | 1294.1 (M + Na)$^+$<br>1310.0 (M + K)$^+$ | |
| Cello-A | $C_{69}H_{123}O_{20}$ | 1271.86 | 1294.1 (M + Na)$^+$<br>1310.0 (M + K)$^+$ | |
| Lac-A | $C_{69}H_{123}O_{20}$ | 1271.86 | 1294.1 (M + Na)$^+$<br>1310.0 (M + K)$^+$ | |
| Melo-A | $C_{69}H_{123}O_{20}$ | 1271.86 | 1294.1 (M + Na)$^+$<br>1310.0 (M + K)$^+$ | |
| iMalt-B | $C_{55}H_{108}O_{13}$ | 976.78 | 999.83 (M + Na)$^+$<br>1015.79 (M + K)$^+$ | |
| Malt-B | $C_{55}H_{108}O_{13}$ | 976.78 | 999.8 (M + Na)$^+$ | |
| Cello-B | $C_{55}H_{108}O_{13}$ | 976.78 | 999.9 (M + Na)$^+$ | |
| Lac-B | $C_{55}H_{108}O_{13}$ | 976.78 | 999.7 (M + Na)$^+$ | |
| Melo-B | $C_{55}H_{108}O_{13}$ | 976.78 | 999.9 (M + Na)$^+$ | |
| Gent2Cald-A | $C_{178}H_{258}O_{40}$ | 3035.82 | 3054.5 (M + Na)$^+$ | |
| Gent2Cald-B | $C_{110}H_{212}O_{20}$ | 1949.53 | 1971.2 (M + Na)$^+$ | |

TABLE 10

Retention of antigen (OVA) in liposomes*

| Liposome/archaeosome (mol % composition) | Retention (%) | Average diameter (nm) | OVA loading (μg OVA/mg) |
|---|---|---|---|
| DPPG/chol (80/20) | 84.5 ± 1.7 | 88 ± 49 | 72.7 |
| DPPG/DPPS/chol (70/10/20) | 93.5 ± 3.7 | 88 ± 53 | 33.3 |
| DPPG/DPPS/chol (60/20/20) | 92.6 ± 1.7 | 109 ± 64 | 50.0 |
| DPPG/DPPS/chol (50/30/20) | 86.6 ± 2.6 | 94 ± 60 | 37.5 |
| DPPG/DPPS/chol (30/30/40) | 50.9 ± 9.1 | 114 ± 70 | 61.5 |

*Leakage of OVA from duplicate 0.1-ml aliquots of liposomes was determined following storage for 6 months at 4° C.. Samples were centrifuged at 202,400 × g ($R_{ave}$) for 1 h. OVA present in supernatant and pellet fractions were quantified by density of the Coomassie stained OVA band following SDS PAGE. Chol = cholesterol.

TABLE 11

Preparation of OVA-liposomes and OVA-archaeosomes containing synthetic glyco-archaeol lipids

| Liposome/archaeosome (mol % composition) | Average diameter (nm) | OVA loading (μg OVA/mg) |
|---|---|---|
| DPPG/chol (80/20) | 123 ± 73 | 58.1 |
| DPPG/chol/Glc$_2$-A (75/20/5) | 87 ± 50 | 57.9 |
| DPPG/chol/Glc$_2$-A (65/20/15) | 118 ± 63 | 39.4 |
| DPPG/chol/Glc$_2$-A (55/20/25) | 117 ± 56 | 35.3 |
| DPPG/chol/Glc$_2$-A (45/20/35) | 134 ± 64 | 41.0 |
| DPPG/chol/Glc$_2$-A (35/20/45) | 213 ± 98 | 43.2 |
| DPPG/chol/Glc$_2$-A (20/20/60) | 364 ± 123 | 24.0 |
| DPPG/Glc$_2$-A (65/35) | unstable | — |
| DPPG/chol/Glc$_2$-A (55/10/35) | 123 ± 60 | 14.8 |
| DPPG/chol/Glc$_2$-A (45/20/35) | 108 ± 53 | 21.1 |
| DPPG/chol/Glc$_2$-A (35/30/35) | 162 ± 82 | 30.8 |
| DPPG/chol/Glc$_2$-A (20/45/35) | 245 ± 124 | 36.5 |
| DPPG/DPPS/chol/Glc$_2$-A (45/20/20/15) | 150 ± 92 | 46.0 |
| Man$_4$-A/DPPG/chol (45/35/20) | 94 ± 55 | 30.0 |
| Glc$_3$-A/DPPG/chol (35/45/20) | 98 ± 53 | 45.8 |
| Glc$_3$-A/AS/chol (35/35/30) | 208 ± 48 | 36.4 |
| Glc$_3$-A/DPPS/chol (35/35/30) | 157 ± 52 | 120.0 |
| Glc$_3$-A/DPPE/chol (35/35/30) | 160 ± 53 | 95.8 |
| Glc$_3$-A/SQDG/chol (35/35/30) | 235 ± 53 | 38.2 |
| Glc$_3$-A/AI/chol (35/35/30) | 169 ± 59 | 23.0 |
| Glc$_3$-A/AG/chol (35/35/30) | 93 ± 56 | 40.7 |
| Glc$_3$-A/AGP-CH$_3$/chol (35/35/30) | 107 ± 39 | 39.2 |
| Glc$_2$-C-PS (100) | 245 ± 81 | 28.8 |
| Glc$_2$-C-PI (100) | 254 ± 77 | 42.0 |
| Glc$_2$-C-Glc$_2$/AS/DPPG (16/30/54) | 137 ± 66 | 101.1 |

*Glc$_2$-A is β-D-Glc-(1,6)-β-D-Glc-archaeol;
Glc$_2$-C-PS is gentiobiose caldarchaetidylserine;
Glc$_2$-C-PI is gentiobiose caldarchaetidylinositol;
Man$_4$-A is α-D-Man-(1,2)-α-D-Man-(1,2)-α-D-Man-(1,2)-α-D-Man-(1,1)-archaeol;
Glc$_3$-A is β-D-Glc-(1,6)-β-D-Glc-(1,6)-β-D-Glc-(1,1)-archaeol;
AS, archaetidylserine;
Glc$_2$-C-Glc$_2$, gentiobiose-caldarchaeol-gentiobiose (see FIGS. 6 and 11).

TABLE 12

Mucosal responses in mice immunized with various adjuvant compositions containing entrapped antigen (OVA).*

| Archaeosome-OVA | IgA | IgA (times blank) | IgG | IgG (times blank) |
|---|---|---|---|---|
| Non-immunized | 0.139 | 1.0 | 0.134 | 1.0 |
| Glc$_2$-C-PI | 1.05 | 7.6 | 1.07 | 8.0 |
| Glc$_2$-C-PS | 0.62 | 4.5 | 0.443 | 3.3 |
| TPL | 0.231 | 1.7 | 0.484 | 3.6 |
| Glc$_3$-A/DPPE/chol | 1.13 | 8.1 | 0.156 | 1.2 |
| Glc$_3$-A/AG/chol | 0.434 | 3.1 | 0.380 | 2.8 |
| Glc$_3$-A/AS/chol | 0.416 | 3.0 | 0.220 | 1.6 |

TABLE 12-continued

Mucosal responses in mice immunized with various adjuvant compositions containing entrapped antigen (OVA).*

| Archaeosome-OVA | IgA | IgA (times blank) | IgG | IgG (times blank) |
|---|---|---|---|---|
| Glc$_3$-A/DPPG/chol | 0.284 | 2.0 | 0.195 | 1.6 |
| Glc$_3$-A/AI/chol | 0.098 | 0.71 | 0.141 | 1.1 |
| Glc$_3$-A/SQDG/chol | 0.152 | 1.1 | 0.138 | 1.0 |

*C57BL/6 mice were immunized subcutaneously at 0 and 3 weeks. Faecal extracts from faeces collected 6 weeks post first injection were assayed for anti OVA antibodies (IgA diluted 1:1; IgG diluted 1:5). Relative amounts of antibody are shown by Elisa absorbance, and normalized based on 100 mg dry weight of faeces. Negative control values (blank values) for faecal extracts from non-immunized mice are shown. Vaccine compositions were the same as in FIGS. 10 and 12. TPL archaeosomes from *Methanobrevibacter smithii* show relatively low IgA response.

TABLE 13

Up-regulation of co-stimulatory molecules on APCs exposed to synthetic glyco-archaeol archaeosomes.*

| Lipid (mol %) | Mean fluorescence Intensity CD80 |
|---|---|
| Lipopolysaccharide | 33.2 |
| Naive | 15.8 |
| DPPG/chol liposomes (80/20) | 14.4 |
| Glc$_2$-archaeol/DPPG/chol (35/45/20) | 32 |
| Man$_4$-archaeol/DPPG/chol (45/35/20) | 29.9 |

*Macrophages J774A.1 cultures were incubated in RPMI + 8% faetal bovine serum medium containing no addition (naive), 10 μg lipopolysaccharide (LPS) from *E. coli* as a positive activator, 25 μg liposomes or 25 μg archaeosomes. Cultures were incubated for 48 h, except for LPS that was incubated 24 h, prior to staining for presence of the co-stimulatory molecule CD80 using anti-CD80-PE (Phycoerythrin). Fluorescence intensity was measured using flow cytometry. Data are acquired from 30,000 events for each sample and the fluorescence intensity of each sample is indicated.

TABLE 14

Protection against skin melanoma in C57BL/6 mice vaccinated with synthetic archaeosomes containing an antigen expressed by the melanoma cells.*

| Vaccine | 6 days | 9 days | 16 days | 20 days | 24 days |
|---|---|---|---|---|---|
| No vaccine | 5 | 5 | 5 | euthanized | |
| OVA** | 2 | 3 | 4 | euthanized | |
| Gentiobiose-A | 0 | 0 | 0 | 0 | 0 |
| Cellobiose-A | 0 | 0 | 1 | 1 | 1 |
| Isomaltose-A | 0 | 0 | 1 | 1 | 1 |

*The numbers of mice that developed a solid tumor (5 mice/group) are shown at various times (days) from subcutaneous injection of tumor cells.
**OVA represents the antigen with no adjuvant as a control.

REFERENCE LIST

1. Agnihotri, G., P. Tiwari, and A. K. Misra. 2005. One-pot synthesis of per-O-acetylated thioglycosides from unprotected reducing sugars. Carbohydr. Res. 340:1393-1396.
2. Benvegnu, T., G. Rethore, M. Brard, W. Richter, and D. Plusquellec. 2005. Archaeosomes based on novel synthetic tetraether-type lipids for the development of oral delivery systems. Chem. Commun. (Camb.) 5536-5538.
3. Berkowitz, W. F. and Y. Wu. 1997. Synthesis of archaebacterial lipid C20 chirons. Tetrahedron Letters 38:8141-8144.
4. Blocher, D., R. Gutermann, B. Henkel, and K. Ring. 1990. Physicochemical characterization of tetraether lipids from *Thermoplasma acidophilum*. V. Evidence for the existence of a metastable state in lipids with acyclic hydrocarbon chains. Biochim. Biophys. Acta 1024:54-60.
5. Cross, G. G. and D. M. Whitfield. 1998. Simplifying Oligosaccharide Synthesis: Boronate Diesters as Cleavable Protecting Groups. SYNLETT. 487-488.
6. Douglas, S. P., D. M. Whitfield, and J. J. Krepinsky. 1995. Polymer-supported solution synthesis of oligosaccharides using a novel versatile linker for the synthesis of D-mannopentaose, a structural unit of D-mannans of pathogenic yeasts. J. Am. Chem. Soc. 117:2116-2117.
7. Eichler, E., F. Yan, J. Sealy, and D. M. Whitfield. 2001. 1-Methyl 1'-cyclopropylmethyl—an acid labile O-protecting group for polymer-supported oligosaccharide synthesis. Tetrahedron 57:6679-6693.
8. Freisleben, H. J., Antonopoulos, E., Balakirev, M., Balakirev, L., Hartmann, K., and Gropp, F. Tetraether lipid derivatives and liposomes and lipid agglomerates containing tetraether lipid derivatives, and use thereof. [U.S. Pat. No. 6,316,260]. 1999.
Ref Type: Patent
9. Gophna, U., R. L. Charlebois, and W. F. Doolittle. 2004. Have archaeal genes contributed to bacterial virulence? Trends Microbiol. 12:213-219.
10. Gumani, K., J. Kennedy, S. Sad, G. D. Sprott, and L. Krishnan. 2004. Phosphatidylserine receptor-mediated recognition of archaeosome adjuvant promotes endocytosis and MHC class I cross-presentation of the entrapped antigen by phagosome-to-cytosol transport and classical processing. J. Immunol. 173:566-578.
11. Huang, X., L. Huang, H. Wang, and X.-S. Ye. 2004. Iterative One-Pot Oligosaccharide Synthesis. Angew Chem. Int. Ed. 43:5221-5224.
12. Kates, M. 1992. Archaebacterial lipids: structure, biosynthesis and function. Biochem. Soc. Symp. 58:51-72.
13. Krishnan, L., C. J. Dicaire, G. B. Patel, and G. D. Sprott. 2000. Archaeosome vaccine adjuvants induce strong humoral, cell-mediated, and memory responses: comparison to conventional liposomes and alum. Infect. Immun. 68:54-63.
14. Krishnan, L., S. Sad, G. B. Patel, and G. D. Sprott. 2000. Archaeosomes induce long-term CD8$^+$ cytotoxic T cell response to entrapped soluble protein by the exogenous cytosolic pathway, in the absence of CD4$^+$ T cell help. J. Immunol. 165:5177-5185.
15. Krishnan, L., S. Sad, G. B. Patel, and G. D. Sprott. 2003. Archaeosomes induce enhanced cytotoxic T lymphocyte responses to entrapped soluble protein in the absence of interleukin 12 and protect against tumor challenge. Cancer Res. 63:2526-2534.
16. Krishnan, L. and G. D. Sprott. 2003. Archaeosomes as self-adjuvanting delivery systems for cancer vaccines. Journal of Drug Targeting 11:515-524.
17. Minamikawa, H. and H. Masakatsu. 1997. Phase behavior of synthetic Phytanyl-Chained Glycolipid/water systems. Langmuir 13:2564-2571.
18. Minamikawa, H., T. Murakami, and H. Masakatsu. 1994. Synthesis of 1,3-di-O-alkyl-2-O-(β-glycosyl)glycerols bearing oligosaccharides as hydrophilic groups. Chem. Phys. Lipids 72:111-118.
19. Palma, A. S., T. Feizi, Y. Zhang, M. S. Stoll, A. M. Lawson, E. Diaz-Rodriguez, M. A. Campanero-Rhodes, J. Costa, S. Gordon, G. D. Brown, and W. Chai. 2006. Ligands for the beta-Glucan Receptor, Dectin-1, Assigned Using "Designer" Microarrays of Oligosaccharide Probes (Neoglycolipids) Generated from Glucan Polysaccharides. J. Biol. Chem. 281:5771-5779.
20. Prakash, G. K. S., T. Matthew, E. R. Marinez, P. M. Esteves, G. Rasul, and G. O. Olah. 2006. BF$_3$2CF$_3$CH$_2$OH (BF$_3$2TFE), an efficient superacidic catalyst for some organic synthetic transformations. J. Org. Chem. 71:3952-3958.

21. Raguse, B., P. N. Culshaw, J. K. Prashar, and K. Raval. 2000. The synthesis of archaebacterial lipid analogues. Tetrahedron Letters 41:2971-2974.
22. Sprott, G. D., L. Bakouche, and K. Rajagopal. 2006. Identification of sulfoquinovosyl diacylglycerol as a major polar lipid in *Marinococcus halophilus* and *Salinicoccus hispanicus* and substitution with phosphatidylglycerol. Can. J. Microbiol. 52:209-219.
23. Sprott, G. D., J. Brisson, C. J. Dicaire, A. K. Pelletier, L. A. Deschatelets, L. Krishnan, and G. B. Patel. 1999. A structural comparison of the total polar lipids from the human archaea *Methanobrevibacter smithii* and *Methanosphaera stadtmanae* and its relevance to the adjuvant activities of their liposomes. Biochim. Biophys. Acta 1440:275-288.
24. Sprott, G. D., I. Ekiel, and C. Dicaire. 1990. Novel, acid-labile, hydroxydiether lipid cores in methanogenic bacteria. J. Biol. Chem. 265:13735-13740.
25. Sprott, G. D., Krishnan, L., Conlan, J. W., Omri, A., and Patel, G. B. Archaeosomes as adjuvants and carriers for acellular vaccines to induce cytotoxic T lymphocyte (CTL) responses. [WO 01/26683 A3]. 2001.
Ref Type: Patent
26. Sprott, G. D., S. Larocque, N. Cadotte, C. J. Dicaire, M. McGee, and J. R. Brisson. 2003. Novel polar lipids of halophilic eubacterium *Planococcus* H8 and archaeon *Haloferax volcanii*. Biochim. Biophys. Acta 1633:179-188.
27. Sprott, G. D., G. B. Patel, and L. Krishnan. 2003. Archaeobacterial ether lipid liposomes as vaccine adjuvants. Methods Enzymol. 373:155-172.
28. Sprott, G. D., Patel, G. B., Makabi-Panzu, B., and Tolson, D. L. Archaeosomes, archaeosomes containing coenzyme Q10, and other types of liposomes containing coenzyme Q10 as adjuvants and as delivery vehicles. PCT/CA 96/00835 [WO 97/22333], 1-57. 1997.
Ref Type: Patent
29. Sprott, G. D., S. Sad, L. P. Fleming, C. J. Dicaire, G. B. Patel, and L. Krishnan. 2003. Archaeosomes varying in lipid composition differ in receptor-mediated endocytosis and differentially adjuvant immune responses to entrapped protein. Archaea 1:151-164.
30. Swain, M., J. R. Brisson, G. D. Sprott, F. P. Cooper, and G. B. Patel. 1997. Identification of beta-L-gulose as the sugar moiety of the main polar lipid *Thermoplasma acidophilum*. Biochim. Biophys. Acta 1345:56-64.
31. Tropper, F. D., F. O. Andersson, C. Grande-Maitre, and R. Roy. 1991. Stereospecific synthesis of 1,2-trans-phenylthio-β-D-disaccharides under phase transfer catalysis. Synthesis 734-736.
32. van Boeckel, C. A. A., P. Westerduin, and J. H. van Boom. 1984. Synthesis of two purple-membrane glycolipids and the glycolipid sulfate O-(β-D-glucopyranosyl-3-sulfate)-(1-6)-O-α-D-mannopyranosyl-(1-2)-O-α-D-glucopyranosyl-(1-1)-2,3-di-O-phytanyl-sn-glycerol. Carbohydrate Research 133:219-234.
33. Yan, H. and H. J. Jennings. 2006. Synthesis of mono- and di-sialophospholipids via the H-phosphonate approach. Can. J. Chem. 84:540-545.

We claim:

1. A synthetic lipid consisting of an archaeal core lipid and at least one polar carbohydrate head group wherein said archaeal core lipid is archaeol (2,3-di-O-diphytanyl-sn-glycerol) or caldarchaeol (2,2',3,3'-tetra-O-dibiphytanyl-sn-diglycerol) and said polar carbohydrate head group is selected from the group consisting of:

β-D-Glc-(1,6)-α-D-Glc-;
α-D-Glc-(1,6)-β-D-Glc-;
β-D-Glc-(1,4)-β-D-Glc-;
α-D-Glc-(1,4)-β-D-Glc-;
β-D-Gal-(1,4)-β-D-Glc-;
α-D-Gal-(1,6)-β-D-Glc-;
β-D-Glc-(1,6)-β-D-Glc-(1,6)-β-D-Glc-;
α-D-Glc-(1,4)-α-D-Glc-(1,4)-β-D-Glc-;
α-D-Man-(1,2)-α-D-Man-(1,2)-α-D-Man-; and
α-D-Man-(1,2)-α-D-Man-(1,2)-α-D-Man-(1,2)-α-D-Man-, and wherein said polar carbohydrate head group is linked to the archaeal core lipid by covalent bonding to at least one free hydroxyl group on the archaeal core lipid.

2. A synthetic lipid according to claim 1, wherein the at least one polar carbohydrate head group is β-D-Gal-(1,4)-β-D-Glc- or β-D-Glc-(1,6)-β-D-Glc-(1,6)-β-D-Glc.

3. An archaeosome comprising at least one synthetic lipid as claimed in claim 1.

4. An archaeosome as claimed in claim 3, further comprising at least one conventional lipid.

5. An archaeosome according to claim 4, wherein the at least one conventional lipid is selected from a group consisting of phosphatidylglycerol, phosphatidylserine, SQDG, and cholesterol.

6. An archaeosome according to claim 5, wherein the at least one conventional lipid comprises cholesterol, and wherein cholesterol is present in an amount of between 10 and 45 mol % of the total lipid composition.

7. An archaeosome according to claim 5, wherein phosphatidylglycerol is present in an amount of between 20 and 80 mol % of the lipid composition.

8. An archaeosome according to claim 5, wherein phosphatidylserine is present in an amount of between 10 and 30 mol % of the lipid composition.

9. An archaeosome as claimed in claim 3 wherein the archaeosome further comprises at least one stabilizing lipid.

10. An archaeosome as claimed in claim 9, wherein the at least one stabilizing lipid comprises cholesterol and at least one of phosphatidylethanolamine, archaetidylglycerol, archaetidylserine or archaetidylglycerolphosphate-methyl.

11. A vaccine comprising an adjuvant and an antigen, the adjuvant comprising the archaeosome of claim 3, wherein the antigen is an amino acid sequence or protein.

12. A method of promoting a protective CD8+ T cell response and/or a protective CD4+ T cell response, comprising administering the vaccine of claim 11 to a subject in need thereof.

13. A method for producing the synthetic lipid of claim 1, comprising the steps of isolating said archaeal lipid core from archaeal cells, and processing the archaeal lipid core to add said at least one polar carbohydrate head group.

14. A method for producing the archaeosome of claim 3 comprising the steps of isolating said archaeal lipid core from archaeal cells, processing the archaeal lipid core to add said at least one polar carbohydrate head group, adding at least one stabilizing lipid, and providing conditions for the formation of the archaeosome.

15. A vaccine comprising an adjuvant and an antigen, the adjuvant comprising the archaeosome of claim 3, wherein the antigen is an amino acid sequence or protein.

16. The archaeosome of claim 10 wherein the archaeosome comprises at least 15-60% of the synthetic lipid as recited in claim 1.

* * * * *